(12) United States Patent
Niitsu et al.

(10) Patent No.: US 9,771,582 B2
(45) Date of Patent: Sep. 26, 2017

(54) RNA INTERFERENCE COMPOSITIONS AND METHODS FOR MALIGNANT TUMORS

(71) Applicant: Nitto Denko Corporation, Osaka (JP)

(72) Inventors: Yoshiro Niitsu, Hokkaido (JP); Kenjirou Minomi, Osaka (JP); Bharat Majeti, San Diego, CA (US); Li Wang, San Diego, CA (US); Jihua Liu, San Marcos, CA (US); Roger Adami, Carlsbad, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/979,566

(22) Filed: Dec. 28, 2015

(65) Prior Publication Data

US 2016/0186182 A1    Jun. 30, 2016

Related U.S. Application Data

(60) Provisional application No. 62/266,661, filed on Dec. 13, 2015, provisional application No. 62/184,241, filed on Jun. 24, 2015.

(30) Foreign Application Priority Data

Dec. 26, 2014   (JP) .................. 2014-266198

(51) Int. Cl.
| | | |
|---|---|---|
| *C07H 21/04* | (2006.01) | |
| *C12N 15/113* | (2010.01) | |
| *C07F 9/6533* | (2006.01) | |
| *C12Q 1/02* | (2006.01) | |
| *G01N 33/58* | (2006.01) | |

(52) U.S. Cl.
CPC .......... *C12N 15/113* (2013.01); *C07F 9/6533* (2013.01); *C12N 15/1137* (2013.01); *C12Q 1/02* (2013.01); *G01N 33/582* (2013.01); *C12N 2310/14* (2013.01); *C12N 2310/322* (2013.01); *C12N 2310/344* (2013.01); *C12N 2310/3515* (2013.01); *C12N 2310/531* (2013.01); *C12N 2320/30* (2013.01)

(58) Field of Classification Search
CPC .................................................. C07H 21/04
See application file for complete search history.

(56) References Cited

U.S. PATENT DOCUMENTS

| | | | |
|---|---|---|---|
| 5,204,241 A | 4/1993 | Pero | |
| 5,968,737 A | 10/1999 | Ali-Osman | |
| 8,067,390 B2 | 11/2011 | Merritt | |
| 8,367,628 B2 | 2/2013 | Goodwin | |
| 8,664,376 B2 | 3/2014 | Niitsu | |
| 8,686,052 B2 | 4/2014 | Niitsu | |
| 8,710,209 B2 | 4/2014 | Jin | |
| 8,741,867 B2 | 6/2014 | Niitsu | |
| 8,895,717 B2 | 11/2014 | Sood | |
| 9,151,758 B2 | 10/2015 | Zetter | |
| 9,206,424 B2 | 12/2015 | Jin | |
| 2003/0144236 A1 | 7/2003 | Weiss | |
| 2003/0165843 A1 | 9/2003 | Shoshan | |
| 2004/0029275 A1* | 2/2004 | Brown .................. | C12N 15/111 435/375 |
| 2004/0219600 A1 | 11/2004 | Williams | |
| 2005/0142596 A1 | 6/2005 | Krolewski | |
| 2005/0233998 A1* | 10/2005 | Jadhav .................. | C12N 15/113 514/44 A |
| 2005/0255487 A1 | 11/2005 | Khvorova | |
| 2007/0083334 A1 | 4/2007 | Mintz | |
| 2007/0083945 A1 | 4/2007 | Byrum | |
| 2009/0181379 A1 | 7/2009 | Corrales Izquierdo | |
| 2009/0220956 A1 | 9/2009 | Nuyten | |
| 2010/0196482 A1 | 8/2010 | Radovic-Moreno | |
| 2011/0269819 A1 | 11/2011 | Jones | |
| 2012/0142754 A1 | 6/2012 | Niitsu | |
| 2012/0276209 A1* | 11/2012 | Cullis .................. | A61K 9/1272 424/490 |
| 2013/0004494 A1 | 1/2013 | Heber-Katz | |
| 2013/0028885 A1 | 1/2013 | Zetter | |
| 2013/0052160 A1 | 2/2013 | Zitvogel | |
| 2013/0053270 A1 | 2/2013 | Gill | |
| 2013/0196434 A1 | 8/2013 | Maier et al. | |

(Continued)

FOREIGN PATENT DOCUMENTS

| | | |
|---|---|---|
| CN | 103695421 A | 4/2014 |
| WO | 9821359 A1 | 5/1998 |

(Continued)

OTHER PUBLICATIONS

Zhang et al. (Gynecologic Oncology 2005: 97; 501-507).*
Xia et al. (BMC 2011, 11:1-9).*
Shi et al. (Cancer Gene Therapy 2009: 227-236).*
Love, Lipid-like materials for low-dose, in vivo gene silencing, Proc Natl Acad Sci U S A., 2010, vol. 107(5), pp. 1864-1869.
Xue, Small RNA combination therapy for lung cancer, Proc Natl Acad Sci U S A, 2014, vol. 111(34), pp. E3553-E3561.
Xu, Enhancing tumor cell response to chemotherapy through nanoparticle-mediated codelivery of siRNA and cisplatin prodrug, Proc Natl Acad Sci U S A, 2013, vol. 110, No. 46, pp. 18638-18643.
Ui-Tei, Functional dissection of siRNA sequence by systematic DNA substitution: modified siRNA with a DNA seed arm is a powerful tool for mammalian gene silencing with significantly reduced off-target effect, Nucleic Acids Res., 2008, vol. 36(7), pp. 2136-2151.

(Continued)

*Primary Examiner* — Kimberly Chong
(74) *Attorney, Agent, or Firm* — Eckman Law Group

(57) ABSTRACT

This invention provides compositions for use in distributing active agents for treating a malignant tumor in a subject. The compositions contain RNAi molecules targeted to a human GST-π, along with RNAi molecules targeted to a human p21, and a pharmaceutically acceptable carrier. The carrier can include nanoparticles composed of an ionizable lipid, a structural lipid, one or more stabilizer lipids, and a lipid for reducing immunogenicity of the nanoparticles. This invention further provides methods for preventing or treating a malignant tumor by administering a therapeutically effective amount of an RNAi composition.

35 Claims, 7 Drawing Sheets

(56) References Cited

U.S. PATENT DOCUMENTS

| | | |
|---|---|---|
| 2013/0330401 A1 | 12/2013 | Payne et al. |
| 2013/0345286 A1 | 12/2013 | Gollob |
| 2014/0017780 A1 | 1/2014 | Bentwich et al. |
| 2014/0134158 A1 | 5/2014 | Bardelli |
| 2014/0303237 A1 | 10/2014 | Shapiro et al. |
| 2014/0315975 A1 | 10/2014 | Niitsu |
| 2014/0315976 A1 | 10/2014 | Brahmbhatt et al. |
| 2014/0356413 A1 | 12/2014 | Niitsu et al. |

FOREIGN PATENT DOCUMENTS

| | | |
|---|---|---|
| WO | 2004094636 A1 | 11/2004 |
| WO | 2009033284 A1 | 3/2009 |
| WO | 2012170952 A2 | 12/2012 |
| WO | 2012176282 A1 | 12/2012 |
| WO | 2013192364 A1 | 12/2013 |
| WO | 2014022739 A2 | 2/2014 |
| WO | 2014098210 A1 | 6/2014 |
| WO | 2014136086 A1 | 9/2014 |

OTHER PUBLICATIONS

Niitsu, Serum Glutathione-S-Transferase-rr as a Tumor Marker for Gastrointestinal Malignancies, Cancer, Jan. 15, 1989, vol. 63, pp. 317-323.

Hirata, Significance of Glutathione S-Transferase-Pi as a Tumor Marker in Patients with Oral Cancer, Cancer, govember 15,1992, vol. 70, No. 10, pp. 2381-2387.

Hida, Serum Glutathione S-Transferase-Pi Level as a Tumor Marker for Non-Small Cell Lung Cancer, Cancer, Mar. 1, 1994, vol. 73, No. 5, pp. 1377-1382.

Ban, Transfection of Glutathione S-Transferase (GST)-Pi Antisense Complementary DNA Increases the Sensitivity of a Colon Cancer Cell Line to Adriamycin, Cisplatin, Melphalan, and Etoposide, Cancer Research, Aug. 1, 1996, vol. 56, 3577-3582.

Morgan, Tumor Efficacy and Bone Marrow-sparing Properties of TER286, a Cytotoxin Activated by Glutathione S-Transferase, Cancer Research, Jun. 15. 1998, vol. 58, pp. 2568-2575.

Niitsu, A proof of glutathione S-transferase-pi-related multidrug resistance by transfer of antisense gene to cancer cells and sense gene to bone marrow stem cell, Chemico-Biological Interactions, 1998, vol. 111-112, pp. 325-332.

Miyanishi, Glutathione S-Transferase-pi Overexpression Is Closely Associated With K-ras Mutation During Human Colon Carcinogenesis, Gastroenterology, 2001, vol. 121, pp. 865-874.

Matsunaga, C(H)OP refractory chronic lymphocytic leukemia patients in whom salvage chemotherapy chosen by evaluating multiple chemotherapeutic drug-resistant factors was remarkably effective, Int J Clin Oncol, 2003, vol. 8, pp. 326-331.

Hayashi, Suppressive effect of sulindac on branch duct-intraductal papillary mucinous neoplasms, J Gastroenterol, 2009, vol. 44, pp. 964-975.

Morse, The role of glutathione S-transferase P1-1 in colorectal cancer: friend or foe?, Gastroenterology, 2001, vol. 121(4), pp. 1010-1013.

Steckel, Determination of synthetic lethal interactions in KRAS oncogene-dependent cancer cells reveals novel therapeutic targeting strategies, Cell Res., 2012, vol. 22(8), pp. 1227-1245.

Collins, KRAS as a key oncogene and therapeutic target in pancreatic cancer, Front Physiol., 2013, vol. 4, Article 407, pp. 1-8.

Ruan, Analysis of EGFR signaling pathway in nasopharyngeal carcinoma cells by quantitative phosphoproteomics, Proteome Science, Jun. 28, 2011, vol. 9, pp. 1-11.

Singhal, 1,3-Bis(3,5-dichlorophenyl) urea compound 'COH-SR4' inhibits proliferation and activates apoptosis in melanoma, Biochemical Pharmacology, Dec. 1, 2012, vol. 84, Iss. 11, pp. 1419-1427.

Hokaiwado, Glutathione S-transferase Pi mediates proliferation of androgen-independent prostate cancer cells, carcinogenesis, Apr. 15, 2008, vol. 29, pp. 1134-1138.

Ashley, Delivery of Small Interfering RNA by Peptide-Targeted Mesoporous Silica Nanoparticle-Supported Lipid Bilayers, ACS Nano. Author Manuscript. Mar. 27, 2012, vol. 6, pp. 1-28.

Yoshimoto, Obesity-Induced Gut Microbial Metabolite Promotes Liver Cancer Through Senescence Secretome, Nature, 2013, pp. 1-7.

Krizhanovsky, Senescence of Activated Stellate Cells Limits Liver Fibrosis, Cell, 22 Aug. 2008, vol. 134, pp. 657-667.

Gupta, Synergistic Tumor Suppression by Combined Inhibition of Telomerase and CDKN1A6, PNAS, Jul. 14, 2014, E3062-E3071.

Sato, Resolution of Liver Cirrhosis Using Vitamin A-Coupled Liposomes to Deliver siRNA Against A Collagen-Specific Chaperone, Nature Biotechnology, Apr. 2008, vol. 26, pp. 431-442.

Cho, Pirfenidone: An Anti-Fibrotic and Cytoprotective Agent as Therapy for Progressive Kidney Disease, Expert Opin Investig Drugs, Author Manuscript, Mar. 16, 2011, vol. 19, pp. 1-13.

Futreal, A Census of Human Cancer Genes, Nature Reviews Cancer 2004, vol. 4, pp. 177-183.

Takahashi et al., Gan To Kagaku Ryoho. 1994; 21 (7): 945-51, English summary p. 951.

Ban et al., Cancer Res. 1996; 56 (15): 3577-82, Transfection of Glutathione S-Transferase (GST)-n' Antisense complementary DNA Increases the Sensitivity of a Colon Cancer Cell Line to Adriamycin, Cisplatin, Melphalan, and Etoposide.

Nakajima et al., J Pharmacol Exp Ther. 2003; 306 (3): 861-9, Reversal of Multiple Drug Resistance in aholangiocarcinoma by the Glutathione S-Transferase-Pi-Specific Inhibitor O1-Hexadecyl-gamma-glutamyl-S-benzylcysteinyl-D-phenylglycine Ethylester.

Hokaiwado et al., Carcinogenesis. 2008; 29 (6): 1134-8, Glutathione S-transferase Pi mediates proliferation of androgen-independent prostate cancer cells.

Adler et.al, EMBO J. 1999, 18, 1321-1334, Regulation of JNK signaling by GSTp.

Townsend, et. al, J. Biol. Chem. 2009, 284, 436-445, Novel Role for Glutathione S-Transferase Pi Regulator of Protein S-Glutathionylation Following Oxidative and Nitrosative Stress.

Yin et.al, Cancer Res. 2000 60, 4053-4057, Glutathione S-Transferase p. Elicits Protection against H2O2-induced Cell Death via Coordinated Regulation of Stress Kinases.

Nishita et al., AACR 102nd Annual Meeting, Abstract No. 1065, 2011, Regulation of autophagy and MAPK signaling by glutathione S-transferase Pi in KRAS mutated cancer cells.

AC114115, GenBank Accession No. AC114115, Rattus norvegicus clone CH230-2808, Working Draft Sequence, 6 unordered pieces, May 13, 2003 [online]. [Retrieved on Apr. 30, 2016). Retrieved from the Internet <URL: http://www.ncbi.nlm.nih.gov/nuccore/AC114115>.

JU528663, GenBank Accession No. JU528663, TSA: Ctenomys sociabilis 330326.Ctso mRNA sequence, Oct. 10, 2012 [online]. [Retrieved on Apr. 30, 2016). Retrieved from the Internet <URL: http://www.ncbi.nlm.nih.gov/nuccore/JU528663>.

GO761423, GenBank Accession No. G0761423, 0010260TNA004657HT OTNA Ovis aries cDNA 5-, mRNA sequence, May 8, 2009 [online]. [Retrieved on Apr. 30, 2016]. Retrieved from the Internet <URL: http://www.ncbi.nlm.nih.gov/nucest/G0761423>.

GO786145, GenBank Accession No. G0786145, 0009200TNA002813HT OTNA Ovis aries cDNA 5-,.mRNA sequence, May 8, 2009 [online). [Retrieved on Apr. 30, 2016]. Retrieved from the internet <URL: http://www.ncbi.nlm.nih.gov/nucest/G0786145>.

AC230665, GenBank Accession No. AC230665, Bos taurus clone CH240-502B15, Jul. 10, 2008 [online]. [Retrieved on May 1, 2016]. Retrieved from the internet <URL:http://www.ncbi.nlm.nih.gov/nuccore/AC230665>.

AC230574, GenBank Accession No. AC230574, Bos taurus clone CH240-504M17, Jul. 10, 2008 [online]. [Retrieved on May 1, 2016]. Retrieved from the internet <URL:http://www.ncbi.nlm.nih.gov/nuccore/AC230574>.

BV207757, GenBank Accession No. BV207757, sqnm2244B3 Human DNA (Sequenom) *Homo sapiens* STS genomic, Oct. 17, 2009 [online]. [Retrieved on May 1, 2016]. Retrieved from the internet <URL: http://www.ncbi.nlm.nih.gov/nuccore/BV207757>.

AW374759, GenBank Accession No. AW374759, MR1-CT005B-291199-003-a05 CT0058 *Homo sapiens* cDNA. mRNA sequence,

(56) References Cited

OTHER PUBLICATIONS

Jan. 9, 2011 [online]. (Retrieved on May 1, 2016). Retrieved from the internet <URL: http://www.ncbi.nlm.nih.gov/nucest/6B79413/>.
Vaishnaw, Review A status report on RNAi therapeutics, Silence, Dec. 31, 2010, vol. 1, pp. 14-26.
Hokaiwado, Glutathione S-transferase Pi mediates proliferation of androgen-independent prostate cancer cells, Carcinogenesis, Jun. 1, 2008, vol. 29, pp. 1134-1138.
Sawers, Glutathione S-transferase P1 (GSTP1) directly influences platinum drug Themosensitivity in ovarian tumour cell lines, British Journal of Cancer, Sep. 9, 2014, vol. 111, pp. 1150-1158.
Tsao et al., Adenovirus-mediated p21 (WAF1 /SDI I/CIP1) gene transfer induces apoptosis of human cervical cancer cell lines, 1999, Journal of Virology, vol. 73, pp. 4983-4990.
Wu et al., Transcriptional regulation during p21 WAF1/CIP-induced apoptosis in human ovarian cancer cells, 2002, JBC, vol. 277, pp. 36329-36337.
Fan et al., An antisense oligodeoxynucleotide to p21 Waf1 /Cip1 causes apoptosis in human breast cancer cells, 2003, Molecular Cancer Therapeutics, vol. 2, pp. 773-782.
Zhang et al., Up-regulation of p21WAF1/CIP1 by small activating RNA inhibits the in vitro and in vivo growth of pancreatic cancer cells, 2012, Tumori, vol. 98, pp. 804-811.
Wagner, In Situ Evidence of KRAS Amplification and Association With Increased p21 Levels in Non-Small Cell Lung Carcinoma, 2009, Am J Clin Pathol, vol. 132, pp. 500-505.
https://cansar.icr.ac.uk/cansar/cell-lines/A549/mutations/ retrieved from the web on Jun. 20, 2016.
Valtorta, KRAS gene amplification in colorectal cancer and impact on response to EGFR-targeted therapy, 2013, Int. J. Cancer, vol. 133, pp. 1259-1266.
Birkeland, KRAS gene amplification and overexpression but not mutation associates with aggressive and metastatic endometrial cancer, 2012, British Journal of Cancer, vol. 107, pp. 1997-2004.

\* cited by examiner

RNA INTERFERENCE COMPOSITIONS AND METHODS FOR MALIGNANT TUMORS

SEQUENCE LISTING

This application includes a Sequence Listing submitted electronically as an ASCII file created on Jan. 2, 2016, named ND5123179US_SL.txt, which is 141,105 bytes in size, and is hereby incorporated by reference in its entirety.

BACKGROUND OF THE INVENTION

Mutation of a KRAS gene can be related to malignant tumors, such as lung adenocarcinoma, mucinous adenoma, ductal carcinoma of the pancreas, and colorectal carcinoma. Recent observations indicate that elevated levels of the protein Glutathione S-transferase-π (GST-π) is associated with such KRAS mutations.

Without wishing to be bound by any one particular theory, it has been found that upon suppression of GST-π in cells, the level of the cell cycle-regulating protein p21 can be surprisingly elevated.

One of the functions of the cell cycle-regulating protein p21 is to inhibit apoptosis. For example, p21 may have the effect of protecting a cell from apoptosis induced by a chemotherapeutic agent, both in vitro and in vivo. See, e.g., Gartel and Tyner, 2002, Mol Cancer Ther., 2002, 1(8):639-49; Abbas and Dutta, 2009, Nat Rev Cancer., 2009, 9(6):400-14. p21 is encoded by CDKN1A gene and belongs to the CIP/KIP family. p21 can function to inhibit cell cycle progression at the G1 phase and the G2/M phase by binding a cyclin-CDK complex. For example, the p21 gene undergoes activation by p53, a tumor suppressor gene. Upon activation of p53 due to DNA damage, p53 activates p21 so that the cell cycle is arrested at the G1 phase and the G2/M phase.

GST-π is a member of the Glutathione S-transferase (IUBMB EC 2.5.1.18) family of six isoenzymes that play a role in detoxification by catalyzing the conjugation of hydrophobic and electrophilic compounds with reduced glutathione. The GST-π gene (GSTP1) is a polymorphic gene encoding active, functionally different GSTP1 variant proteins that are thought to function in xenobiotic metabolism. GSTP1 may play a role in susceptibility to cancer and is expressed abundantly in tumor cells. See, e.g., Aliya S. et al. Mol Cell Biochem., 2003 November; 253(1-2):319-327. Glutathione S-transferase-π is an enzyme that in humans is encoded by the GSTP1 gene. See, e.g., Bora P S, et al. (October 1991) J. Biol. Chem., 266 (25): 16774-16777. The GST-π isoenzyme has been shown to catalyze the conjugation of GSH with some alkylating anti-cancer agents, suggesting that over-expression of GST-π would result in tumor cell resistance.

Elevated serum GST-π levels were observed in patients with various gastrointestinal malignancies including gastric, esophageal, colonic, pancreatic, hepatocellular, and biliary tract cancers. Over 80% of patients with Stage III or IV gastric cancer and even about 50% of those with Stage I and II had elevated levels of serum GST-π. See, e.g., Niitsu Y, et al. Cancer, 1989 Jan. 15; 63(2):317-23. GST-π was found to be a useful marker for predicting the recurrence of tumors in patients with oral cancer after chemotherapy. See, e.g., Hirata S. et al. Cancer, 1992 Nov. 15:70(10):2381-7.

In human colorectal cancer, KRAS mutation appears to induce overexpression of GST-π via activation of AP-1. See, e.g., Miyanishi et al., Gastroenterology, 2001; 121 (4):865-74.

Expression of GST-π increases in various cancer cells, which may be related to resistance to some anticancer agents. See, e.g. Ban et al., Cancer Res., 1996, 56(15):3577-82; Nakajima et al., J Pharmacol Exp Ther., 2003, 306(3): 861-9.

Agents for suppressing GST-π have been disclosed for inducing apoptosis in cells. However, such compositions and techniques also caused autophagy and required the combined action of various agents. See, e.g., US 2014/0315975 A1. Moreover, suppressing GST-π has not been found to shrink or reduce tumors. For example, in a cancer that was overexpressing GST-π, the weights of tumors were not affected by suppressing GST-π, although other effects were observed. See, e.g., Hokaiwado et al., Carcinogenesis, 2008, 29(6):1134-1138.

There is an urgent need for methods and compositions to develop therapies for patients with malignancies, such as siRNA sequences, compounds and structures for inhibition of expression of GST-π and p21.

What is needed are methods and compositions for preventing or treating malignant tumors. There is a continuing need for RNAi molecules, and other structures and compositions for preventing, treating, or reducing malignant tumors.

BRIEF SUMMARY

This invention relates to the fields of biopharmaceuticals and therapeutics composed of nucleic acid based molecules. More particularly, this invention relates to methods and compositions for delivering RNA interference agents for preventing, treating or ameliorating the effects of conditions and diseases involving malignant tumors.

This invention provides compositions and methods for RNAi molecules that are targeted to human GST-π, in combination with RNAi molecules targeted to human p21. The compositions include a pharmaceutically acceptable carrier.

This invention relates to molecules and compositions thereof for use in biopharmaceuticals and therapeutics for malignant tumors. More particularly, this invention relates to compounds, compositions and methods for providing nanoparticles to deliver and distribute active agents or drug compounds to cells, tissues, organs, and subjects having malignant tumors.

Included are methods for preventing, treating or ameliorating one or more symptoms of a malignant tumor in a subject in need. The method can involve administering to the subject an effective amount of a composition of RNAi molecules targeted to GST-π and p21.

Embodiments of this invention include the following:

A composition comprising RNAi molecules targeted to a human GST-π, RNAi molecules targeted to a human p21, and a pharmaceutically acceptable carrier. The RNAi molecules can contain a 2'-deoxynucleotide in one or more of positions 2 to 8 from the 3' end of the antisense strand.

The carrier can include liposome nanoparticles that encapsulate the RNAi molecules. The liposome nanoparticles can encapsulate the RNAi molecules and retain at least 80% of the encapsulated RNAi molecules after 1 hour exposure to human serum. The liposome nanoparticles can have a size of 10 to 1000 nm, or 10 to 150 nm.

The composition can be active for treating malignant tumor, which may be located in any organ or tissue, including lung, colon, kidney, pancreas, liver, bone, skin, or intestine.

The liposome nanoparticles can be composed of an ionizable lipid, a structural lipid, one or more stabilizer lipids, and a lipid for reducing immunogenicity of the nanoparticles. The ionizable lipid can be selected from the group of compound 81, compound 71, compound 57, compound 84, compound 49, compound 76, compound 78, and compound 102.

This invention further contemplates methods for preventing, treating or ameliorating one or more symptoms of a malignant tumor in a subject in need. The method can involve administering to the subject an effective amount of a composition above.

In some embodiments, the malignant tumor may be associated with KRAS mutation, the method further comprising identifying a tumor cell in the subject, the tumor cell comprising at least one of: (i) a mutation of the KRAS gene, and (ii) an aberrant expression level of KRAS protein.

In certain embodiments, the malignant tumor can overexpress GST-π.

The RNAi molecules can decrease expression of GST-π and p21 in the subject. In some embodiments, the administration can decrease expression of GST-π and p21 in the subject by at least 5% for at least 5 days. The administration can decrease the volume of the malignant tumor in the subject by at least 5%, or at least 10%, or at least 20%, or at least 30%, or at least 40%, or at least 50%. The method may reduce one or more symptoms of the malignant tumor, or delays or terminates the progression of the malignant tumor.

In certain embodiments, the administration may reduce growth of malignant tumor cells in the subject. The administration can reduce growth for at least 2%, or at least 5%, or at least 10%, or at least 15%, or at least 20% of the malignant tumor cells in the subject.

In some aspects, the malignant tumor can be colon cancer, pancreatic cancer, kidney cancer, lung cancer, breast cancer, fibrosarcoma, lung adenocarcinoma, mucinous adenoma, ductal carcinoma of the pancreas, or colorectal carcinoma.

Embodiments of this invention can provide methods where administration is performed from 1 to 12 times per day. The administration may be performed for a duration of 1, 2, 3, 4, 5, 6 or 7 days, or for a duration of 1, 2, 3, 4, 5, 6, 8, 10 or 12 weeks.

In some embodiments, the administration can be a dose of from 0.01 to 2 mg/kg of the RNAi molecules at least once per day for a period up to twelve weeks. In further embodiments, the administration can provide a mean AUC(0-last) of from 1 to 1000 ug*min/mL and a mean $C_{max}$ of from 0.1 to 50 ug/mL for the GST-π RNAi molecule. In certain embodiments, the administration may provide a mean AUC (0-last) of from 1 to 1000 ug*min/mL and a mean $C_{max}$ of from 0.1 to 50 ug/mL for the p21 RNAi molecule.

Methods of administration can be intravenous injection, intradermal injection, subcutaneous injection, intramuscular injection, intraperitoneal injection, oral, topical, infusion, or inhalation.

BRIEF DESCRIPTION OF THE DRAWINGS

As shown in FIG. 3, the level of expression of PUMA for a formulation of GST-π and p21 siRNAs was greatly increased from about 2-4 days after transfection of the GST-π and p21 siRNAs.

As shown in FIG. 4, after 43 days, the GST-π siRNA showed markedly advantageous tumor inhibition, with final primary tumor average weights significantly reduced by 2.8-fold, as compared to control.

In FIG. 6, the expression of PUMA was greatly increased from 2-6 days after transfection of the GST-π siRNA.

FIG. 7 shows that a GST-π siRNA of this invention provided knockdown efficacy for A549 xenograft tumors in vivo. Dose dependent knockdown of GST-π mRNA was observed in athymic nude (nu/nu) female mice (Charles River) with the siRNA targeted to GST-π. As shown in FIG. 7, at a dose of 4 mg/kg, significant reduction of about 40% in GST-π mRNA was detected 24 hours after injection.

DETAILED DESCRIPTION OF THE INVENTION

Figure 1:
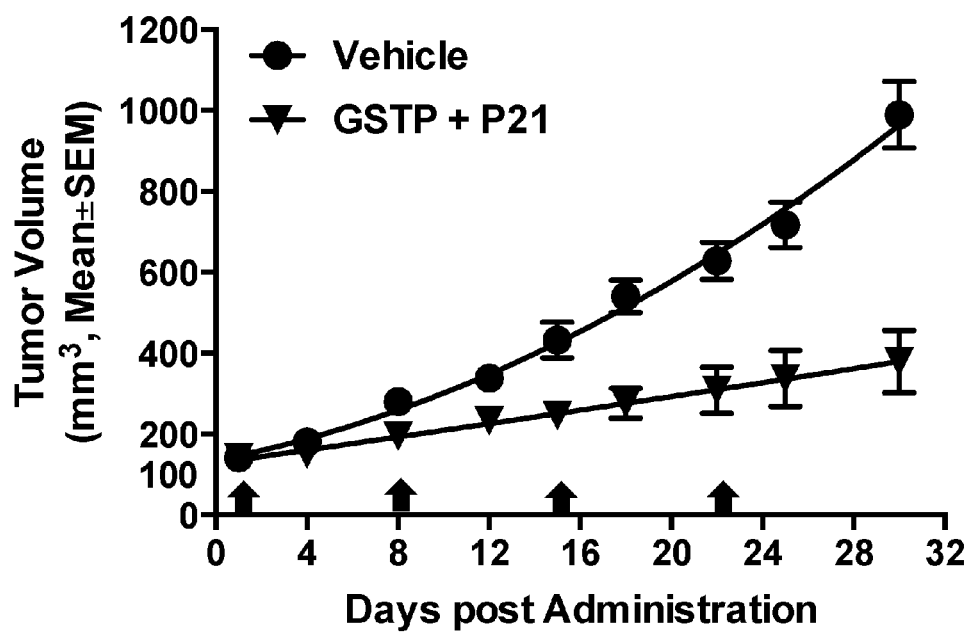
FIG. 1 shows profound reduction of cancer xenograft tumors in vivo using a formulation of GST-π and p21 siRNAs of this invention. The GST-π and p21 siRNAs provided gene knockdown potency in vivo when administered in a liposomal formulation to the cancer xenograft tumors. A cancer xenograft model was utilized with a relatively low dose at 1.15 mg/kg for the GST-π siRNA and 0.74 mg/kg for the p21 siRNA. The formulation of GST-π and p21 siRNAs showed significant tumor inhibition efficacy within a few days after administration. After 30 days, the GST-π and p21 siRNAs showed markedly advantageous tumor inhibition efficacy, with tumor volume reduced by greater than 2-fold as compared to control.

This invention provides compounds and compositions for use in therapeutic combinations for delivery to malignant tumors. In some aspects, this invention relates to compounds, compositions and methods for providing nanoparticles to deliver and distribute active agents or drug compounds to malignant tumor cells, as well as tissues, organs, and subjects having malignant tumors.

This invention provides a range of ionizable compounds for delivering the active agents to cells of malignant tumors. Among other uses, the ionizable compounds of this invention can be used to form nanoparticles to deliver and distribute active agents for ameliorating malignant tumors.

Embodiments of this invention include a broad range of compounds having lipid-like properties, and such compounds can be used to deliver active agents for uptake to malignant tumor cells.

The compositions and methods of this invention can be used to distribute agents for suppressing gene expression. Examples of an agent for suppressing gene expression include inhibitory nucleic acid molecules, including ribozymes, anti-sense nucleic acids, and RNA interference molecules (RNAi molecules).

In another aspect, this invention provides methods for utilizing therapeutic compositions that decrease the expression of a GST-π nucleic acid molecule or polypeptide and a p21 nucleic acid molecule or polypeptide for the treatment of a neoplasia in a subject, wherein the neoplasia is associated with cells containing a KRAS mutation or displaying aberrant KRAS expression levels.

The therapeutic compositions of this invention can include inhibitory nucleic acid molecules such as siRNAs, shRNAs, and antisense RNAs, as well as DNA-directed RNAs (ddRNA), Piwi-interacting RNAs (piRNA), and repeat associated siRNAs (rasiRNA).

A KRAS-associated malignant tumor or KRAS-associated cancer is defined herein as (a) a cancer cell or tumor cell containing a somatic KRAS mutation, or (b) a cancer cell or tumor cell with an abnormal expression level of KRAS including, but not limited to, amplification of the KRAS encoding DNA, or over-expression of the KRAS gene, or under-expression of the KRAS gene when compared to level found in normal, non-cancer cells.

GST-π denotes an enzyme, which is encoded by the GSTP1 gene, and catalyzes glutathione conjugation. GST-π is present in various animals, including humans, and its sequence information is known and given in NCBI database accession numbers (e.g., human: NP_000843 (NM_000852), rat: NP_036709 (NM_012577), mouse: NP_038569 (NM_013541), etc.

This invention encompasses RNAi molecules for suppressing DNA encoding GST-π, ribozymes, antisense nucleic acids, DNA/RNA chimeric polynucleotides, and vectors for expressing them, and dominant negative variants of GST-π.

p21 is present in various animals including humans, and its sequence information is also publicly known (e.g., human: NM_000389.4, NM_078467.2, NM_001291549.1, NM_001220778.1, NM_001220777.1 (NP_001207707.1, NP_001278478.1, NP_001207706.1, NP_510867.1, NP_000380.1), etc.; the numbers represent accession numbers of the NCBI database, and the nucleotide sequence and the amino acid sequence are indicated outside and inside the parentheses, respectively). As one example, the nucleotide sequence of the human CDKN1A gene is registered in the database as NM_000389.4. As for p21, sequence information has been registered with a plurality of accession numbers as mentioned above, and a plurality of transcript variants are present.

This invention encompasses RNAi molecules for suppressing DNA encoding p21, ribozymes, antisense nucleic acids, DNA/RNA chimeric polynucleotides, and vectors for expressing them, and dominant negative variants of p21.

In general, after a subject is diagnosed as having a neoplasia, e.g., a lung cancer, kidney cancer or a pancreatic cancer, associated with a KRAS mutation or a KRAS amplification, a method of treatment involving suppression of GST-π and p21 is selected.

Examples of an agent that suppresses GST-π as used herein include a drug that suppresses GST-π production and/or activity, and a drug that promotes GST-π degradation and/or inactivation. Examples of the drug that suppresses GST-π production include an RNAi molecule, a ribozyme, an antisense nucleic acid, a DNA/RNA chimera polynucleotide for DNA encoding GST-π, or a vector expressing same.

Examples of an agent that suppresses p21 as used herein include a drug that suppresses p21 production and/or activity, and a drug that promotes p21 degradation and/or inactivation. Examples of the drug that suppresses p21 production include an RNAi molecule, a ribozyme, an antisense nucleic acid, a DNA/RNA chimera polynucleotide for DNA encoding p21, or a vector expressing same.

RNAi Molecules

One of ordinary skill in the art would understand that a reported sequence may change over time and to incorporate any changes needed in the nucleic acid molecules herein accordingly.

Embodiments of this invention can provide compositions and methods for gene silencing of GST-π expression using nucleic acid molecules.

Embodiments of this invention can provide compositions and methods for gene silencing of p21 expression using nucleic acid molecules.

Embodiments of this invention can provide compositions and methods for gene silencing of a combination of GST-π and p21 expression using nucleic acid molecules.

Examples of nucleic acid molecules capable of mediating RNA interference include molecules active in RNA interference (RNAi molecules), including a duplex RNA such as an siRNA (small interfering RNA), miRNA (micro RNA), shRNA (short hairpin RNA), ddRNA (DNA-directed RNA), piRNA (Piwi-interacting RNA), or rasiRNA (repeat associated siRNA), and modified forms thereof.

The composition and methods disclosed herein can also be used in treating various kinds of malignant tumors in a subject.

The nucleic acid molecules and methods of this invention may be pooled, or used in combination to down regulate the expression of genes that encode GST-π, and to down regulate the expression of genes that encode p21.

The compositions and methods of this invention can include one or more nucleic acid molecules, which in combination can modulate or regulate the expression of GST-π and p21 proteins and/or genes encoding the proteins, proteins and/or genes encoding the proteins that are associated with the maintenance and/or development of diseases, as well as conditions or disorders associated with GST-π and p21, such as malignant tumor.

The compositions and methods of this invention are described with reference to exemplary sequences of GST-π and p21. A person of ordinary skill in the art would understand that various aspects and embodiments of the invention are directed to any related GST-π or p21 genes, sequences, or variants, such as homolog genes and transcript variants, and polymorphisms, including single nucleotide polymorphism (SNP) associated with any GST-π or p21 genes.

In some embodiments, the compositions and methods of this invention can provide a double-stranded short interfering nucleic acid (siRNA) molecule that downregulates the expression of a GST-π gene, for example human GST-π. The compositions and methods of this invention further contemplate providing a double-stranded short interfering nucleic acid (siRNA) molecule that downregulates the expression of a p21 gene, for example human p21.

A RNAi molecule of this invention can be targeted to GST-π or p21, and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of this invention include RNAi molecules that are active against any portion of GST-π mRNA. The RNAi molecule can include a sequence complementary to any mRNA encoding a GST-π sequence. This invention further contemplates compositions and methods including RNAi molecules that are active against any portion of p21 mRNA. The RNAi molecule can include a sequence complementary to any mRNA encoding a p21 sequence.

In some embodiments, a RNAi molecule of this disclosure can have activity against GST-π RNA, where the RNAi molecule includes a sequence complementary to an RNA having a variant GST-π encoding sequence, for example, a mutant GST-π gene known in the art to be associated with malignant tumor. In some embodiments, a RNAi molecule of this disclosure can have activity against p21 RNA, where the RNAi molecule includes a sequence complementary to an RNA having a variant p21 encoding sequence, for example, a mutant p21 gene known in the art to be associated with malignant tumor.

In further embodiments, a RNAi molecule of this invention can include a nucleotide sequence that can mediate silencing of GST-π gene expression. In further embodiments, a RNAi molecule of this invention can include a nucleotide sequence that can mediate silencing of p21 gene expression.

Examples of RNAi molecules of this invention targeted to GST-π mRNA are shown in Table 1.

TABLE 1

RNAi molecule sequences for GST-π

| ID | Ref Pos | SEQ ID NO | SENSE STRAND (5'-->3') SEQ ID NOS: 1 to 65 | SEQ ID NO | ANTISENSE STRAND (5'-->3') SEQ ID NOS: 66 to 130 |
|---|---|---|---|---|---|
| A1 | 652 | 1 | UCCCAGAACCAGGGAGGCAtt | 66 | UGCCUCCCUGGUUCUGGGAca |
| A10 | 635 | 2 | CUUUUGAGACCCUGCUGUCtt | 67 | GACAGCAGGGUCUCAAAAGgc |
| A11 | 649 | 3 | CUGUCCCAGAACCAGGGAGtt | 68 | CUCCCUGGUUCUGGGACAGca |
| A12 | 650 | 4 | UGUCCCAGAACCAGGGAGGtt | 69 | CCUCCCUGGUUCUGGGACAgc |
| A13 | 631 | 5 | AAGCCUUUUGAGACCCUGCtt | 70 | GCAGGGUCUCAAAAGGCUUca |
| A14 | 638 | 6 | UUGAGACCCUGCUGUCCCAtt | 71 | UGGGACAGCAGGGUCUCAAaa |
| A15 | 636 | 7 | UUUUGAGACCCUGCUGUCCtt | 72 | GGACAGCAGGGUCUCAAAAgg |
| A16 | 640 | 8 | GAGACCCUGCUGUCCCAGAtt | 73 | UCUGGGACAGCAGGGUCUCaa |
| A17 | 332 | 9 | GCUGGAAGGAGGAGGUGGUtt | 74 | ACCACCUCCUCCUUCCAGCtc |
| A18 | 333 | 10 | CUGGAAGGAGGAGGUGGUGtt | 75 | CACCACCUCCUCCUUCCAGct |
| A19 | 321 | 11 | UCAGGGCCAGAGCUGGAAGtt | 76 | CUUCCAGCUCUGGCCCUGAtc |
| A2 | 639 | 12 | UGAGACCCUGCUGUCCCAGtt | 77 | CUGGGACAGCAGGGUCUCAaa |
| A20 | 323 | 13 | AGGGCCAGAGCUGGAAGGAtt | 78 | UCCUUCCAGCUCUGGCCCUga |
| A21 | 331 | 14 | AGCUGGAAGGAGGAGGUGGtt | 79 | CCACCUCCUCCUUCCAGCUct |
| A22 | 641 | 15 | AGACCCUGCUGUCCCAGAAtt | 80 | UUCUGGGACAGCAGGGUCUca |
| A23 | 330 | 16 | GAGCUGGAAGGAGGAGGUGtt | 81 | CACCUCCUCCUUCCAGCUCtg |
| A25 | 647 | 17 | UGCUGUCCCAGAACCAGGGtt | 82 | CCCUGGUUCUGGGACAGCAgg |
| A26 | 653 | 18 | CCCAGAACCAGGGAGGCAAtt | 83 | UUGCCUCCCUGGUUCUGGGac |
| A3 | 654 | 19 | CCAGAACCAGGGAGGCAAGtt | 84 | CUUGCCUCCCUGGUUCUGGga |

TABLE 1-continued

RNAi molecule sequences for GST-π

| Ref ID | Pos | SEQ ID NO | SENSE STRAND (5'-->3') SEQ ID NOS: 1 to 65 | SEQ ID NO | ANTISENSE STRAND (5'-->3') SEQ ID NOS: 66 to 130 |
|---|---|---|---|---|---|
| A4 | 637 | 20 | UUUGAGACCCUGCUGUCCCtt | 85 | GGGACAGCAGGGUCUCAAAag |
| A5 | 642 | 21 | GACCCUGCUGUCCCAGAACtt | 86 | GUUCUGGGACAGCAGGGUCtc |
| A6 | 319 | 22 | GAUCAGGGCCAGAGCUGGAtt | 87 | UCCAGCUCUGGCCCUGAUCtg |
| A7 | 632 | 23 | AGCCUUUUGAGACCCUGCUtt | 88 | AGCAGGGUCUCAAAAGGCUtc |
| A8 | 633 | 24 | GCCUUUUGAGACCCUGCUGtt | 89 | CAGCAGGGUCUCAAAAGGCtt |
| A9 | 634 | 25 | CCUUUUGAGACCCUGCUGUtt | 90 | ACAGCAGGGUCUCAAAAGGct |
| AG7 | 632 | 26 | CGCCUUUUGAGACCCUGCAtt | 91 | UGCAGGGUCUCAAAAGGCGtc |
| AK1 | 257 | 27 | CCUACACCGUGGUCUAUUUtt | 92 | AAAUAGACCACGGUGUAGGgc |
| AK10 | 681 | 28 | UGUGGGAGACCAGAUCUCCtt | 93 | GGAGAUCUGGUCUCCCACAat |
| AK11 | 901 | 29 | GCGGGAGGCAGAGUUUGCCtt | 94 | GGCAAACUCUGCCUCCCGCtc |
| AK12 | 922 | 30 | CCUUUCUCCAGGACCAAUAtt | 95 | UAUUGGUCCUGGAGAAAGGaa |
| AK13/A24 | 643 | 31 | ACCCUGCUGUCCCAGAACCtt | 96 | GGUUCUGGGACAGCAGGGUct |
| AK2 | 267 | 32 | GGUCUAUUUCCCAGUUCGAtt | 97 | UCGAACUGGGAAAUAGACCac |
| AK3 | 512 | 33 | CCCUGGUGGACAUGGUGAAtt | 98 | UUCACCAUGUCCACCAGGGct |
| AK4 | 560 | 34 | ACAUCUCCCUCAUCUACACtt | 99 | GUGUAGAUGAGGGAGAUGUat |
| AK5 | 593 | 35 | GCAAGGAUGACUAUGUGAAtt | 100 | UUCACAUAGUCAUCCUUGCcc |
| AK6 | 698 | 36 | CCUUCGCUGACUACAACCUtt | 101 | AGGUUGUAGUCAGCGAAGGag |
| AK7 | 313 | 37 | CUGGCAGAUCAGGGCCAGAtt | 102 | UCUGGCCCUGAUCUGCCAGca |
| AK8 | 421 | 38 | GACGGAGACCUCACCCUGUtt | 103 | ACAGGGUGAGGUCUCCGUCct |
| AK9 | 590 | 39 | CGGGCAAGGAUGACUAUGUtt | 104 | ACAUAGUCAUCCUUGCCCGcc |
| AU10 | 635 | 40 | CUUUUGAGACCCUGCUGUAtt | 105 | UACAGCAGGGUCUCAAAAGgc |
| AU23 | 330 | 41 | GAGCUGGAAGGAGGAGGUAtt | 106 | UACCUCCUCCUUCCAGCUCtg |
| AU24 | 643 | 42 | ACCCUGCUGUCCCAGAACAtt | 107 | UGUUCUGGGACAGCAGGGUct |
| AU25 | 648 | 43 | UGCUGUCCCAGAACCAGGAtt | 108 | UCCUGGUUCUGGGACAGCAgg |
| AU7 | 632 | 44 | AGCCUUUUGAGACCCUGCAtt | 109 | UGCAGGGUCUCAAAAGGCUtc |
| AU9 | 634 | 45 | CCUUUUGAGACCCUGCUGAtt | 110 | UCAGCAGGGUCUCAAAAGGct |
| B1 | 629 | 46 | UGAAGCCUUUUGAGACCCUtt | 111 | AGGGUCUCAAAAGGCUUCAgt |
| B10 | 627 | 47 | ACUGAAGCCUUUUGAGACCtt | 112 | GGUCUCAAAAGGCUUCAGUtg |
| B11 | 596 | 48 | AGGAUGACUAUGUGAAGGCtt | 113 | GCCUUCACAUAGUCAUCCUtg |
| B12 | 597 | 49 | GGAUGACUAUGUGAAGGCAtt | 114 | UGCCUUCACAUAGUCAUCCtt |
| B13 | 598 | 50 | GAUGACUAUGUGAAGGCACtt | 115 | GUGCCUUCACAUAGUCAUCct |
| B14 | 564 | 51 | CUCCCUCAUCUACACCAACtt | 116 | GUUGGUGUAGAUGAGGGAGat |
| B2 | 630 | 52 | GAAGCCUUUUGAGACCCUGtt | 117 | CAGGGUCUCAAAAGGCUUCag |
| B3 | 563 | 53 | UCUCCCUCAUCUACACCAAtt | 118 | UUGGUGUAGAUGAGGGAGAtg |
| B4 | 567 | 54 | CCUCAUCUACACCAACUAUtt | 119 | AUAGUUGGUGUAGAUGAGGga |

TABLE 1-continued

RNAi molecule sequences for GST-π

| ID | Ref Pos | SEQ ID NO | SENSE STRAND (5'-->3') SEQ ID NOS: 1 to 65 | SEQ ID NO | ANTISENSE STRAND (5'-->3') SEQ ID NOS: 66 to 130 |
|---|---|---|---|---|---|
| B5 | 566 | 55 | CCCUCAUCUACACCAACUAtt | 120 | UAGUUGGUGUAGAUGAGGGAg |
| B6 | 625 | 56 | CAACUGAAGCCUUUUGAGAtt | 121 | UCUCAAAAGGCUUCAGUUGcc |
| B7 | 626 | 57 | AACUGAAGCCUUUUGAGACtt | 122 | GUCUCAAAAGGCUUCAGUUgc |
| B8 | 628 | 58 | CUGAAGCCUUUUGAGACCCtt | 123 | GGGUCUCAAAAGGCUUCAGtt |
| B9 | 565 | 59 | UCCCUCAUCUACACCAACUtt | 124 | AGUUGGUGUAGAUGAGGGAga |
| BG3 | 563 | 60 | GCUCCCUCAUCUACACCAAtt | 125 | UUGGUGUAGAUGAGGGAGCtg |
| BU2 | 630 | 61 | GAAGCCUUUUGAGACCCUAtt | 126 | UAGGGUCUCAAAAGGCUUCag |
| BU10 | 627 | 62 | ACUGAAGCCUUUUGAGACAtt | 127 | UGUCUCAAAAGGCUUCAGUtg |
| BU14 | 565 | 63 | CUCCCUCAUCUACACCAAAtt | 128 | UUUGGUGUAGAUGAGGGAGat |
| BU4 | 567 | 64 | CCUCAUCUACACCAACUAAtt | 129 | UUAGUUGGUGUAGAUGAGGga |
| C1-934 | 934 | 65 | ACCAAUAAAAUUUCUAAGAtt | 130 | UCUUAGAAAUUUUAUUGGUcc |

Key for Table 1: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine respectively.

Examples of RNAi molecules of this invention targeted to GST-π mRNA are shown in Table 2.

TABLE 2

RNAi molecule sequences for GST-π

| ID | SEQ ID NO | SENSE STRAND (5'-->3') SEQ ID NOS: 131 to 156 | SEQ ID NO | ANTISENSE STRAND (5'-->3') SEQ ID NOS: 157 to 182 |
|---|---|---|---|---|
| BU2' | 131 | GAAGCCUUUUGAGACCCUANN | 157 | UAGGGUCUCAAAAGGCUUCNN |
| 14 | 132 | GAAGCCUUUUGAGACCCUAUU | 158 | UAGGGUCUCAAAAGGCUUCUU |
| 15 | 133 | GAAGCCUUUUGAGACCCUAUU | 159 | uagggucuCAAAAGGCUUCUU |
| 16 | 134 | GAAGCCUUUUGAGACCCUAUU | 160 | UagggucuCAAAAGGCUUCUU |
| 17 | 135 | GAAGCCUUUUGAGACCCUAUU | 161 | UAgggucuCAAAAGGCUUCUU |
| 18 | 136 | GAAGCCUUUUGAGACCCUAUU | 162 | UAGggucuCAAAAGGCUUCUU |
| 19 | 137 | GAAGCCUUUUGAGACCCUAUU | 163 | UAGGgucuCAAAAGGCUUCUU |
| 20 | 138 | GAAGCCUUUUGAGACCCUAUU | 164 | uAgGgUcUCAAAAGGCUUCUU |
| 21 | 139 | GAAGCCUUUUGAGACCCUAUU | 165 | UAgGgUcUCAAAAGGCUUCUU |
| 22 | 140 | GAAGCCUUUUGAGACCCUAUU | 166 | UaGgGuCuCAAAAGGCUUCUU |
| 23 | 141 | GAAGCCUUUUGAGACCCUAUU | 167 | UAGgGuCuCAAAAGGCUUCUU |
| 24 | 142 | GAAGCCUUUUGAGACCCUAtt | 168 | UagggucuCAAAGGCUUCUU |
| 25 | 143 | GAAGCCUUUUGAGACCCUAUU | 169 | UAGGGUCUCAAAAGGCUUCUU |
| 26 | 144 | GAAGCCUUUUGAGACCCUAUU | 170 | fUAGGGUCUCAAAAGGCUUCUU |
| 27 | 145 | GAAGCCUUUUGAGACCCUAUU | 171 | uAGGGUCUCAAAAGGCUUCUU |
| 28 | 146 | GAAGCCUUUUGAGACCCUAUU | 172 | UsAGGGUCUCAAAAGGCUUCUU |

TABLE 2-continued

RNAi molecule sequences for GST-π

| SEQ ID | SEQ ID NO | SENSE STRAND (5'-->3') SEQ ID NOS: 131 to 156 | SEQ ID NO | ANTISENSE STRAND (5'-->3') SEQ ID NOS: 157 to 182 |
|---|---|---|---|---|
| 29 | 147 | GAAGCCUUUUGAGACCCUfAUU | 173 | fUAGGGUCUfCAAAAGGCfUUCUU |
| 30 | 148 | GAAGCCUUUUGAGfACCCUfAUU | 174 | fUAGGGUCUfCAfAfAAGGCfUUCUU |
| 31 | 149 | GAAGCCUUUUGAGACCCUAUU | 175 | UAGGGUCUCAAAAGGCUUCUU |
| 31' | 150 | GAAGCCUUUUGAGACCCUAUU | 176 | fUAGGGUCUCAAAAGGCUUCUU |
| 32 | 151 | GAAGCCUUUUGAGACCCUAUU | 177 | UAGGGUCUCAAAAGGCUUCUU |
| 39 | 152 | GAAGCCUUUUGAGACCCUAUU | 178 | UAGgGuCuCAAAAGGCUUCUU |
| 45 | 153 | GAAGCCUUUUGAGACCCUAUU | 179 | UAGgGuCuCAAAAGGCUUCUU |
| 46 | 154 | GAAGCCUUUUGAGACCCUAUU | 180 | UAGgGuCuCAAAAGGCUUCUU |
| 47 | 155 | GAAGCCUUUUGAGACCCUAUU | 181 | UAGgGuCuCAAAAGGCUUCUU |
| 48 | 156 | GAAGCCUUUUGAGACCCUAUU | 182 | fUAGgGuCuCAAAAGGCUUCUU |

Key for Table 2: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 3.

TABLE 3

RNAi molecule sequences for GST-π

| SEQ ID | SEQ ID NO | SENSE STRAND (5'-->3') SEQ ID NOS: 183 to 194 | SEQ ID NO | ANTISENSE STRAND (5'-->3') SEQ ID NOS: 195 to 206 |
|---|---|---|---|---|
| A9' | 183 | CCUUUUGAGACCCUGCUGUNN | 195 | ACAGCAGGGUCUCAAAAGGNN |
| 1 | 184 | CCUCAUCUACACCAACUAUUU | 196 | AUAGUUGGUGUAGAUGAGGUU |
| 2 | 185 | CCUCAUCUACACCAACUAUUU | 197 | auaguuggUGUAGAUGAGGUU |
| 3 | 186 | CCUCAUCUACACCAACUAUUU | 198 | AuaguuggUGUAGAUGAGGUU |
| 4 | 187 | CCUCAUCUACACCAACUAUUU | 199 | AUaguuggUGUAGAUGAGGUU |
| 5 | 188 | CCUCAUCUACACCAACUAUUU | 200 | AUAguuggUGUAGAUGAGGUU |
| 6 | 189 | CCUCAUCUACACCAACUAUUU | 201 | AUAGuuggUGUAGAUGAGGUU |
| 7 | 190 | CCUCAUCUACACCAACUAUUU | 202 | aUaGuUgGUGUAGAUGAGGUU |
| 8 | 191 | CCUCAUCUACACCAACUAUUU | 203 | AUaGuUgGUGUAGAUGAGGUU |
| 9 | 192 | CCUCAUCUACACCAACUAUUU | 204 | AuAgUuGgUGUAGAUGAGGUU |
| 10 | 193 | CCUCAUCUACACCAACUAUUU | 205 | AUAgUuGgUGUAGAUGAGGUU |
| 11 | 194 | CCUCAUCUACACCAACUAUUU | 206 | AuaguuggUGUAGAUGAGGUU |

Key for Table 3: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 4.

TABLE 4

RNAi molecule sequences for GST-π

| SEQ ID | SEQ ID NO SEQ ID NOS: 207 to 221 | SENSE STRAND (5'-->3') | SEQ ID NO SEQ ID NOS: 222 to 236 | ANTISENSE STRAND (5'-->3') |
|---|---|---|---|---|
| B13' | 207 | GAUGACUAUGUGAAGGCACNN | 222 | GUGCCUUCACAUAGUCAUCNN |
| 4 | 208 | GGAUGACUAUGUGAAGGCA<u>UU</u> | 223 | UGCCUUCACAUAGUCAUCC<u>UU</u> |
| 5 | 209 | GGAUGACUAUGUGAAGGCA<u>UU</u> | 224 | ugccuucaCAUAGUCAUCC<u>UU</u> |
| 6 | 210 | GGAUGACUAUGUGAAGGCA<u>UU</u> | 225 | UgccuucaCAUAGUCAUCC<u>UU</u> |
| 7 | 211 | GGAUGACUAUGUGAAGGCA<u>UU</u> | 226 | UGccuucaCAUAGUCAUCC<u>UU</u> |
| 8 | 212 | GGAUGACUAUGUGAAGGCA<u>UU</u> | 227 | UGCcuucaCAUAGUCAUCC<u>UU</u> |
| 9 | 213 | GGAUGACUAUGUGAAGGCA<u>UU</u> | 228 | UGCCuucaCAUAGUCAUCC<u>UU</u> |
| 10 | 214 | GGAUGACUAUGUGAAGGCA<u>UU</u> | 229 | uGcCuUcACAUAGUCAUCC<u>UU</u> |
| 11 | 215 | GGAUGACUAUGUGAAGGCA<u>UU</u> | 230 | UGcCuUcACAUAGUCAUCC<u>UU</u> |
| 12 | 216 | GGAUGACUAUGUGAAGGCA<u>UU</u> | 231 | UgCcUuCaCAUAGUCAUCC<u>UU</u> |
| 13 | 217 | GGAUGACUAUGUGAAGGCA<u>UU</u> | 232 | UGCcUuCaCAUAGUCAUCC<u>UU</u> |
| 14 | 218 | <u>GGAUGAC</u>UAUGUGAAGGCA<u>UU</u> | 233 | UgccuucaCAUAG<u>UC</u>A<u>UC</u>C<u>UU</u> |
| 15 | 219 | GGAUGACUAUfGUfGAAGGCA<u>UU</u> | 234 | UGCfCUUCACAUAGUCAUCC<u>UU</u> |
| 17 | 220 | <u>GG</u>AUGACUAUGUGAAGGCA<u>UU</u> | 235 | UGCCUUCA<u>CAUAGUCAUC</u>C<u>UU</u> |
| 18 | 221 | <u>GG</u>AUGACUAUGUGAAGGCA<u>UU</u> | 236 | UGCCUUCAC<u>AUAGUC</u>A<u>UC</u>C<u>UU</u> |

Key for Table 4: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, <u>U</u>, a, c, g, u, t, or a modified, inverted, or chemically modified nucleotide.

Examples of RNAi molecules of this invention targeted to GST-π mRNA are shown in Table 5.

TABLE 5

RNAi molecule sequences for GST-π

| SEQ ID | SEQ ID NO SEQ ID NOS: 237 to 248 | SENSE STRAND (5'-->3') | SEQ ID NO SEQ ID NOS: 249 to 260 | ANTISENSE STRAND (5'-->3') |
|---|---|---|---|---|
| B2' | 237 | GAAGCCUUUUGAGACCCUGNN | 249 | CAGGGUCUCAAAAGGCUUCNN |
| 1 | 238 | GAAGCCUUUUGAGACCCUG<u>UU</u> | 250 | CAGGGUCUCAAAAGGCUUC<u>UU</u> |
| 2 | 239 | GAAGCCUUUUGAGACCCUG<u>UU</u> | 251 | cagggucuCAAAAGGCUUC<u>UU</u> |
| 3 | 240 | GAAGCCUUUUGAGACCCUG<u>UU</u> | 252 | CagggucuCAAAAGGCUUC<u>UU</u> |
| 4 | 241 | GAAGCCUUUUGAGACCCUG<u>UU</u> | 253 | CAgggucuCAAAAGGCUUC<u>UU</u> |
| 5 | 242 | GAAGCCUUUUGAGACCCUG<u>UU</u> | 254 | CAGggucuCAAAAGGCUUC<u>UU</u> |
| 6 | 243 | GAAGCCUUUUGAGACCCUG<u>UU</u> | 255 | CAGGgucuCAAAAGGCUUC<u>UU</u> |
| 7 | 244 | GAAGCCUUUUGAGACCCUG<u>UU</u> | 256 | cAgGgUcUCAAAAGGCUUC<u>UU</u> |
| 8 | 245 | GAAGCCUUUUGAGACCCUG<u>UU</u> | 257 | CAgGgUcUCAAAAGGCUUC<u>UU</u> |
| 9 | 246 | GAAGCCUUUUGAGACCCUG<u>UU</u> | 258 | CaGgGuCuCAAAAGGCUUC<u>UU</u> |

TABLE 5-continued

RNAi molecule sequences for GST-π

| SEQ ID NO | SENSE STRAND (5'-->3') SEQ ID NOS: 237 to 248 | SEQ ID NO | ANTISENSE STRAND (5'-->3') SEQ ID NOS: 249 to 260 |
|---|---|---|---|
| 10 | 247 GAAGCCUUUUGAGACCCUGUU | 259 | CAGgGuCuCAAAAGGCUUCUU |
| 11 | 248 GAAGCCUUUUGAGACCCUGUU | 260 | CagggucuCAAAAGGCUUCUU |

Key for Table 5: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 6.

TABLE 6

RNAi molecule sequences for GST-π

| SEQ ID NO | SENSE STRAND (5'-->3') SEQ ID NOS: 261 to 272 | SEQ ID NO | ANTISENSE STRAND (5'-->3') SEQ ID NOS: 273 to 284 |
|---|---|---|---|
| B4' | 261 CCUCAUCUACACCAACUAUNN | 273 | AUAGUUGGUGUAGAUGAGGNN |
| 1 | 262 CCUCAUCUACACCAACUAUUU | 274 | AUAGUUGGUGUAGAUGAGGUU |
| 2 | 263 CCUCAUCUACACCAACUAUUU | 275 | auaguuggUGUAGAUGAGGUU |
| 3 | 264 CCUCAUCUACACCAACUAUUU | 276 | AuaguuggUGUAGAUGAGGUU |
| 4 | 265 CCUCAUCUACACCAACUAUUU | 277 | AUaguuggUGUAGAUGAGGUU |
| 5 | 266 CCUCAUCUACACCAACUAUUU | 278 | AUAguuggUGUAGAUGAGGUU |
| 6 | 267 CCUCAUCUACACCAACUAUUU | 279 | AUAguuggUGUAGAUGAGGUU |
| 7 | 268 CCUCAUCUACACCAACUAUUU | 280 | aUaGuUgGUGUAGAUGAGGUU |
| 8 | 269 CCUCAUCUACACCAACUAUUU | 281 | AUaGuUgGUGUAGAUGAGGUU |
| 9 | 270 CCUCAUCUACACCAACUAUUU | 282 | AuAgUuGgUGUAGAUGAGGUU |
| 10 | 271 CCUCAUCUACACCAACUAUUU | 283 | AUAgUuGgUGUAGAUGAGGUU |
| 11 | 272 CCUCAUCUACACCAACUAUUU | 284 | AuaguuggUGUAGAUGAGGUU |

Key for Table 6: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to p21 mRNA are shown in Table 7.

TABLE 7

RNAi molecule sequences for p21

| Ref Pos | SEQ ID NO | SENSE STRAND (5'-->3') SEQ ID NOS: 285 to 312 | SEQ ID NO | ANTISENSE STRAND (5'-->3') SEQ ID NOS: 313 to 340 |
|---|---|---|---|---|
| 2085 | 285 | CUUAGUGACUUUACUUGUAmUmU | 313 | UACAAGUAAAGUCACUAAGmUmU |
| 500 | 286 | CAGACCAGCAUGACAGAUUmUmU | 314 | AAUCUGUCAUGCUGGUCUGmUmU |
| 540 | 287 | UGAUCUUCUCCAAGAGGAAmUmU | 315 | UUCCUCUUGGAGAAGAUCAmUmU |
| 1706 | 288 | GUUCAUUGCACUUUGAUUAmUmU | 316 | UAAUCAAAGUGCAAUGAACmUmU |

TABLE 7-continued

RNAi molecule sequences for p21

| Ref Pos | SEQ ID NO SEQ ID NOS: 285 to 312 | SENSE STRAND (5'-->3') | SEQ ID NO SEQ ID NOS: 313 to 340 | ANTISENSE STRAND (5'-->3') |
|---|---|---|---|---|
| 1709 | 289 | CAUUGCACUUUGAUUAGCAmUmU | 317 | UGCUAAUCAAAGUGCAAUGmUmU |
| 210 | 290 | AGCGAUGGAACUUCGACUUmUmU | 318 | AAGUCGAAGUUCCAUCGCUmUmU |
| 211 | 291 | GCGAUGGAACUUCGACUUUmUmU | 319 | AAAGUCGAAGUUCCAUCGCmUmU |
| 1473 | 292 | GGGAAGGGACACACAAGAAmUmU | 320 | UUCUUGUGUGUCCCUUCCCmUmU |
| 1507 | 293 | UCUACCUCAGGCAGCUCAAmUmU | 321 | UUGAGCUGCCUGAGGUAGAmUmU |
| 2067 | 294 | GGUGCUCAAUAAAUGAUUCmUmU | 322 | GAAUCAUUUAUUGAGCACCmUmU |
| 1063 | 295 | CAUCAUCAAAAACUUUGGAmUmU | 323 | UCCAAAGUUUUUGAUGAUGmUmU |
| 1735 | 296 | AAGGAGUCAGACAUUUUAAmUmU | 324 | UUAAAAUGUCUGACUCCUUmUmU |
| 783 | 297 | GUGCUGGGCAUUUUUAUUUmUmU | 325 | AAAUAAAAAUGCCCAGCACmUmU |
| 869 | 298 | GCCGGCUUCAUGCCAGCUAmUmU | 326 | UAGCUGGCAUGAAGCCGGCmUmU |
| 1060 | 299 | GGGCAUCAUCAAAAACUUUmUmU | 327 | AAAGUUUUUGAUGAUGCCCmUmU |
| 1492 | 300 | GAAGGGCACCCUAGUUCUAmUmU | 328 | UAGAACUAGGGUGCCCUUCmUmU |
| 1704 | 301 | CAGUUCAUUGCACUUUGAUmUmU | 329 | AUCAAAGUGCAAUGAACUGmUmU |
| 1733 | 302 | ACAAGGAGUCAGACAUUUUmUmU | 330 | AAAAUGUCUGACUCCUUGUmUmU |
| 1847 | 303 | UGGAGGCACUGAAGUGCUUmUmU | 331 | AAGCACUUCAGUGCCUCCAmUmU |
| 2000 | 304 | GCAGGGACCACACCCUGUAmUmU | 332 | UACAGGGUGUGGUCCCUGCmUmU |
| 2014 | 305 | CUGUACUGUUCUGUGUCUUmUmU | 333 | AAGACACAGAACAGUACAGmUmU |
| 677 | 306 | UUAAACACCUCCUCAUGUAmUmU | 334 | UACAUGAGGAGGUGUUUAAmUmU |
| 475 | 307 | AGACUCUCAGGGUCGAAAAmUmU | 335 | UUUUCGACCCUGAGAGUCUmUmU |
| 508 | 308 | CAUGACAGAUUUCUACCACmUmU | 336 | GUGGUAGAAAUCUGUCAUGmUmU |
| 514 | 309 | AGAUUUCUACCACUCCAAAmUmU | 337 | UUUGGAGUGGUAGAAAUCUmUmU |
| 549 | 310 | CCAAGAGGAAGCCCUAAUCmUmU | 338 | GAUUAGGGCUUCCUCUUGGmUmU |
| 382 | 311 | GACAGCAGAGGAAGACCAUmUmU | 339 | AUGGUCUUCCUCUGCUGUCmUmU |
| 2042 | 312 | CUCCCACAAUGCUGAAUAUmUmU | 340 | AUAUUCAGCAUUGUGGGAGmUmU |

Key for Table 7: Upper case A, G, C and U referred to for ribo-A, ribo-G, ribo-C and ribo-U respectively. The lower case letters a, g, c, t represent 2'-deoxy-A, 2'-deoxy-G, 2'-deoxy-C and thymidine respectively. mU is 2'-methoxy-U.

Examples of RNAi molecules of this invention targeted to p21 mRNA are shown in Table 8.

TABLE 8

RNAi molecule sequences for p21

| Ref Pos | SEQ ID NO SEQ ID NOS: 341 to 354 | SENSE STRAND (5'-->3') | SEQ ID NO SEQ ID NOS: 355 to 368 | ANTISENSE STRAND (5'-->3') |
|---|---|---|---|---|
| 1735' | 341 | AAGGAGUCAGACAUUUUAANN | 355 | UUAAAAUGUCUGACUCCUUNN |
| 1 | 342 | AAGGAGUCAGACAUUUUAAUU | 356 | UUAaAaUgUCUGACUCCUUUU |
| 2 | 343 | AAGGAGUCAGACAUUUUAAUU | 357 | UUAaAaUgUCUGACUCCUUUU |
| 3 | 344 | AAGGAGUCAGACAUUUUAAUU | 358 | UUAaAaUgUCUGACUCCUUUU |
| 4 | 345 | AAGGAGUCAGACAUUUUAAUU | 359 | UUAaAaUgUCUGACUCCUUUU |

TABLE 8-continued

RNAi molecule sequences for p21

| Ref Pos | SEQ ID NO | SENSE STRAND (5'-->3') SEQ ID NOS: 341 to 354 | SEQ ID NO | ANTISENSE STRAND (5'-->3') SEQ ID NOS: 355 to 368 |
|---|---|---|---|---|
| 5 | 346 | AAGGAGUCAGACAUUUUAA<u>UU</u> | 360 | UUaaaaug<u>UCUGACUCCUUUU</u> |
| 6 | 347 | AAGGAGUCAGACAUUUUAA<u>UU</u> | 361 | UUAAaaug<u>UCUGACUCCUUUU</u> |
| 7 | 348 | AAGGAGUCAGACAUUUUAA<u>UU</u> | 362 | uUaAaAu<u>GUCUGACUCCUUUU</u> |
| 8 | 349 | AAGGAGUCAGACAUUUUAA<u>UU</u> | 363 | UUaAaAu<u>GUCUGACUCCUUUU</u> |
| 9 | 350 | AAGGAGUCAGACAUUUUAA<u>UU</u> | 364 | UUaAaAu<u>GUCUGACUCCUUUU</u> |
| 10 | 351 | AAGGAGUCAGACAUUUUAA<u>UU</u> | 365 | <u>UU</u>AAAA<u>U</u>GUC<u>U</u>GACUCCUU<u>UU</u> |
| 11 | 352 | AAGGAGU<u>C</u>AGA<u>C</u>AUUUUAA<u>UU</u> | 366 | <u>UU</u>AAAAUGUCUGACUCCUU<u>UU</u> |
| 12 | 353 | <u>AA</u>GGAGUCAGACAUUUUAA<u>UU</u> | 367 | <u>UU</u>AAAAUGUCUGACUCCUU<u>UU</u> |
| 13 | 354 | <u>AA</u>GGAGU<u>C</u>AGA<u>C</u>AUUUUAA<u>UU</u> | 368 | <u>UU</u>AAAAUGUCUGACUCCUU<u>UU</u> |

Key for Table 8: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT = T = t) respectively. Underlining refers to 2'-OMe-substituted, e.g., <u>U</u>. N is A, C, G, U, <u>U</u>, a, c, g, u, t, or a modified, inverted, or chemically modified nucleotide.

In some embodiments, this invention provides a range of nucleic acid molecules, where a) the molecule has a polynucleotide sense strand and a polynucleotide antisense strand; b) each strand of the molecule is from 15 to 30 nucleotides in length; c) a contiguous region of from 15 to 30 nucleotides of the antisense strand is complementary to a sequence of an mRNA encoding p21; and d) at least a portion of the sense strand is complementary to at least a portion of the antisense strand, and the molecule has a duplex region of from 15 to 30 nucleotides in length.

In some embodiments, the nucleic acid molecule can have a contiguous region of from 15 to 30 nucleotides of the antisense strand that is complementary to a sequence of an mRNA encoding p21, and is located in the duplex region of the molecule.

In additional embodiments, the nucleic acid molecule can have a contiguous region of from 15 to 30 nucleotides of the antisense strand that is complementary to a sequence of an mRNA encoding p21.

In further aspects, a nucleic acid molecule of this invention can have each strand of the molecule being from 18 to 22 nucleotides in length. A nucleic acid molecule can have a duplex region of 19 nucleotides in length.

In certain embodiments, a nucleic acid molecule can have a polynucleotide sense strand and the polynucleotide antisense strand that are connected as a single strand, and form a duplex region connected at one end by a loop.

The nucleic acid molecules of this invention can have a blunt end, and can have one or more 3' overhangs.

The nucleic acid molecules of this invention can be RNAi molecules that are active for gene silencing, for example, a dsRNA that is active for gene silencing, a siRNA, a microRNA, or a shRNA active for gene silencing, as well as a DNA-directed RNA (ddRNA), a Piwi-interacting RNA (piRNA), and a repeat associated siRNA (rasiRNA).

This invention provides a range of nucleic acid molecules that are active for inhibiting expression of p21. In some embodiments, the nucleic acid molecule can have an IC50 for knockdown of p21 of less than 100 pM.

In additional embodiments, the nucleic acid molecule can have an IC50 for knockdown of p21 of less than 50 pM.

This invention further contemplates compositions containing one or more inventive nucleic acid molecules and a pharmaceutically acceptable carrier. The carrier can be a lipid molecule or liposome.

The compounds and compositions of this invention are useful in methods for preventing or treating a p21 associated disease, by administering a compound or composition to a subject in need.

In further aspects, this invention includes methods for treating a disease associated with p21 expression, by administering to a subject in need a composition containing one or more inventive nucleic acid molecules. The disease can be malignant tumor, which may be presented in a disease such as cancers associated with p21 expression, among others.

In some embodiments, this invention provides a range of nucleic acid molecules, wherein: a) the molecule has a polynucleotide sense strand and a polynucleotide antisense strand; b) each strand of the molecule is from 15 to 30 nucleotides in length; c) a contiguous region of from 15 to 30 nucleotides of the antisense strand is complementary to a sequence of an mRNA encoding GST-π; d) at least a portion of the sense strand is complementary to at least a portion of the antisense strand, and the molecule has a duplex region of from 15 to 30 nucleotides in length.

In some embodiments, the nucleic acid molecule can have contiguous region of from 15 to 30 nucleotides of the antisense strand that is complementary to a sequence of an mRNA encoding GST-π is located in the duplex region of the molecule.

In additional embodiments, the nucleic acid molecule can have a contiguous region of from 15 to 30 nucleotides of the antisense strand that is complementary to a sequence of an mRNA encoding GST-π.

In certain embodiments, each strand of the nucleic acid molecule can be from 18 to 22 nucleotides in length. The duplex region of the nucleic acid molecule can be 19 nucleotides in length.

In alternative forms, the nucleic acid molecule can have a polynucleotide sense strand and a polynucleotide antisense strand that are connected as a single strand, and form a duplex region connected at one end by a loop.

Some embodiments of a nucleic acid molecule of this disclosure can have a blunt end. In certain embodiments, a nucleic acid molecule can have one or more 3' overhangs.

This invention provides a range of nucleic acid molecules that are RNAi molecules active for gene silencing. The inventive nucleic acid molecules can be a dsRNA, a siRNA, a micro-RNA, or a shRNA active for gene silencing, as well as a DNA-directed RNA (ddRNA), Piwi-interacting RNA (piRNA), or a repeat associated siRNA (rasiRNA). The nucleic acid molecules can be active for inhibiting expression of GST-π.

Embodiments of this invention further provide nucleic acid molecules having an IC50 for knockdown of GST-π of less than 100 pM.

Additional embodiments of this invention provide nucleic acid molecules having an IC50 for knockdown of GST-π of less than 50 pM.

This invention further contemplates compositions containing one or more of the inventive nucleic acid molecules, along with a pharmaceutically acceptable carrier. In certain embodiments, the carrier can be a lipid molecule or liposome.

The compounds and compositions of this invention are useful in methods for preventing or treating a GST-π associated disease, by administering a compound or composition to a subject in need.

As used herein, the RNAi molecule denotes any molecule that causes RNA interference, including a duplex RNA such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof. These RNAi molecules may be commercially available or may be designed and prepared based on known sequence information, etc. The antisense nucleic acid includes RNA, DNA, PNA, or a complex thereof. As used herein, the DNA/RNA chimera polynucleotide includes a double-strand polynucleotide composed of DNA and RNA that inhibits the expression of a target gene.

In one embodiment, the agents of this invention contain siRNA as a therapeutic agent. An siRNA molecule can have a length from about 10-50 or more nucleotides. An siRNA molecule can have a length from about 15-45 nucleotides. An siRNA molecule can have a length from about 19-40 nucleotides. An siRNA molecule can have a length of from 19-23 nucleotides. An siRNA molecule of this invention can mediate RNAi against a target mRNA. Commercially available design tools and kits, such as those available from Ambion, Inc. (Austin, Tex.), and the Whitehead Institute of Biomedical Research at MIT (Cambridge, Mass.) allow for the design and production of siRNA.

Methods for Treating Malignant Tumor

Embodiments of this invention can provide RNAi molecules that can be used to down regulate or inhibit the expression of GST-π and/or GST-π proteins, as well as RNAi molecules that can be used to down regulate or inhibit the expression of p21 and/or p21 proteins.

In some embodiments, a RNAi molecule of this invention can be used to down regulate or inhibit the expression of GST-π and/or GST-π proteins arising from GST-π haplotype polymorphisms that may be associated with a disease or condition such as malignant tumor. Embodiments of this invention further contemplate a RNAi molecule that can be used to down regulate or inhibit the expression of p21 and/or p21 proteins arising from p21 haplotype polymorphisms that may be associated with a disease or condition such as malignant tumor.

Monitoring of GST-π protein or mRNA levels, as well as p21 protein or mRNA levels can be used to characterize gene silencing, and to determine the efficacy of compounds and compositions of this invention.

The RNAi molecules of this disclosure can be used individually, or in combination with other siRNAs for modulating the expression of one or more genes.

The RNAi molecules of this disclosure can be used individually, or in combination, or in conjunction with other known drugs for preventing or treating diseases, or ameliorating symptoms of conditions or disorders associated with GST-π and p21, including malignant tumor.

The RNAi molecules of this invention can be used to modulate or inhibit the expression of GST-π in a sequence-specific manner. Also, RNAi molecules of this invention can be used to modulate or inhibit the expression of p21 in a sequence-specific manner.

The RNAi molecules of this disclosure can include a guide strand for which a series of contiguous nucleotides are at least partially complementary to a GST-π mRNA or a p21 mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by determining the level of GST-π mRNA or the level of GST-π protein in cells of affected tissue. Treatment of malignant tumor may also be characterized by determining the level of p21 mRNA or the level of p21 protein in cells of affected tissue.

Treatment of malignant tumor may be characterized by non-invasive medical scanning of an affected organ or tissue.

Embodiments of this invention may include methods for preventing, treating, or ameliorating the symptoms of a disease or condition associated with GST-π and/or p21 in a subject in need thereof.

In some embodiments, methods for preventing, treating, or ameliorating the symptoms of malignant tumor in a subject can include administering to the subject a RNAi molecule of this invention to modulate the expression of a GST-π gene, and/or of a p21 gene in the subject or organism.

In some embodiments, this invention contemplates methods for down regulating the expression of a GST-π gene in a cell or organism, by contacting the cell or organism with a RNAi molecule of this invention. This invention further contemplates methods for down regulating the expression of a p21 gene in a cell or organism, by contacting the cell or organism with a RNAi molecule of this invention.

GST-π and p21 inhibitory nucleic acid molecules can be nucleotide oligomers that may be employed as single-stranded or double-stranded nucleic acid molecule to decrease gene expression. In one approach, the inhibitory nucleic acid molecule is a double-stranded RNA used for RNA interference (RNAi)-mediated knockdown of gene expression. In one embodiment, a double-stranded RNA (dsRNA) molecule that is active in RNA interference is made that includes from eight to twenty-five (e.g., 8, 10, 12, 15, 16, 17, 18, 19, 20, 21, 22, 23, 24, 25) consecutive nucleotides of a nucleotide oligomer of the invention. The dsRNA can be two complementary strands of RNA that have duplexed, or a single RNA strand that has self-duplexed (small hairpin (sh)RNA).

In some embodiments, dsRNAs that are active in RNA interference are about 21 or 22 base pairs, but may be shorter or longer, up to about 29 nucleotides. Double stranded RNA can be made using standard techniques, e.g., chemical synthesis or in vitro transcription. Kits are available, for example, from Ambion (Austin, Tex.) and Epicentre (Madison, Wis.).

Methods for expressing dsRNA in mammalian cells are described in Brummelkamp et al. Science 296:550-553, 2002; Paddison et al. Genes & Devel. 16:948-958, 2002; Paul et al. Nature Biotechnol. 20:505-508, 2002; Sui et al., Proc. Natl. Acad. Sci. USA 99:5515-5520, 2002; Yu et al. Proc. Natl. Acad. Sci. USA 99:6047-6052, 2002; Miyagishi et al., Nature Biotechnol. 20:497-500, 2002; and Lee et al., Nature Biotechnol. 20:500-505 2002, each of which is hereby incorporated by reference.

An inhibitory nucleic acid molecule that "corresponds" to a GST-π gene comprises at least a fragment of the double-stranded gene, such that each strand of the double-stranded inhibitory nucleic acid molecule is capable of binding to the complementary strand of the target GST-π gene. The inhibitory nucleic acid molecule need not have perfect correspondence to the reference GST-π sequence.

An inhibitory nucleic acid molecule that "corresponds" to a p21 gene comprises at least a fragment of the double-stranded gene, such that each strand of the double-stranded inhibitory nucleic acid molecule is capable of binding to the complementary strand of the target p21 gene. The inhibitory nucleic acid molecule need not have perfect correspondence to the reference p21 sequence.

In one embodiment, a siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleotide sequence of the inhibitory nucleic acid molecule exhibits 1, 2, 3, 4, 5 or more mismatches.

The inhibitory nucleic acid molecules provided by the invention are not limited to siRNAs, but include any nucleic acid molecule sufficient to decrease the expression of a GST-π or p21 nucleic acid molecule or polypeptide. The DNA sequences provided herein may be used, for example, in the discovery and development of therapeutic antisense nucleic acid molecule to decrease the expression of the encoded protein. The invention further provides catalytic RNA molecules or ribozymes. Such catalytic RNA molecules can be used to inhibit expression of a target nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and US 2003/0003469 A1, each of which is incorporated by reference.

In various embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., Biochemistry, 28:4929, 1989, and Hampel et al., Nucleic Acids Research, 18: 299, 1990. Those skilled in the art will recognize that what is needed in an enzymatic nucleic acid molecule is a specific substrate binding site that is complementary to one or more of the target gene RNA regions, and that it have nucleotide sequences within or surrounding that substrate binding site which impart an RNA cleaving activity to the molecule.

Suppression of a target may be determined by the expression or activity of the corresponding protein in cells being suppressed, as compared to cells in which a suppressing agent is not utilized. Expression of protein may be evaluated by any known technique; examples thereof include an immunoprecipitation method utilizing an antibody, EIA, ELISA, IRA, IRMA, a western blot method, an immunohistochemical method, an immunocytochemical method, a flow cytometry method, various hybridization methods utilizing a nucleic acid that specifically hybridizes with a nucleic acid encoding the protein or a unique fragment thereof, or a transcription product (e.g., mRNA) or splicing product of said nucleic acid, a northern blot method, a Southern blot method, and various PCR methods.

The activity of the protein may be evaluated by analyzing a known activity of the protein including binding to a protein such as, for example, Raf-1 (in particular phosphorylated Raf-1) or EGFR (in particular phosphorylated EGFR) by means of any known method such as for example an immunoprecipitation method, a western blot method, amass analysis method, a pull-down method, or a surface plasmon resonance (SPR) method.

Examples of the mutated KRAS include, but are not limited to, those having a mutation that causes constant activation of KRAS, such as a mutation that inhibits endogenous GTPase or a mutation that increases the guanine nucleotide exchange rate. Specific examples of such mutation include, but are not limited to, for example, mutation in amino acids 12, 13 and/or 61 in human KRAS (inhibiting endogenous GTPase) and mutation in amino acids 116 and/or 119 in human KRAS (increasing guanine nucleotide exchange rate) (Bos, Cancer Res. 1989; 49 (17): 4682-9, Levi et al., Cancer Res. 1991; 51 (13): 3497-502).

In some embodiments of the present invention, the mutated KRAS can be a KRAS having a mutation in at least one of amino acids 12, 13, 61, 116, and 119 of human KRAS. In one embodiment of the present invention, the mutated KRAS has a mutation at amino acid 12 of human KRAS. In some embodiments, the mutated KRAS may be one that induces overexpression of GST-π. Cells having mutated KRAS may exhibit overexpression of GST-π.

Detection of mutated KRAS may be carried out using any known technique, e.g., selective hybridization by means of a nucleic acid probe specific to a known mutation sequence, an enzyme mismatch cleavage method, sequencing (Bos, Cancer Res. 1989; 49 (17): 4682-9), and a PCR-RFLP method (Miyanishi et al., Gastroenterology. 2001; 121 (4): 865-74).).

Detection of target expression may be carried out using any known technique. Whether or not the target is being overexpressed may be evaluated by for example comparing the degree of expression of the target in cells having mutated KRAS with the degree of expression of the target in the same type of cells having normal KRAS. In this situation, the target is being overexpressed if the degree of expression of the target in cells having mutated KRAS exceeds the degree of expression of the target in the same type of cells having normal KRAS.

In one aspect, the invention features a vector encoding an inhibitory nucleic acid molecule of any of the above aspects. In a particular embodiment, the vector is a retroviral, adeno-viral, adeno-associated viral, or lentiviral vector. In another embodiment, the vector contains a promoter suitable for expression in a mammalian cell.

The amount of active RNA interference inducing ingredient formulated in the composition of the present invention may be an amount that does not cause an adverse effect exceeding the benefit of administration. Such an amount may be determined by an in vitro test using cultured cells, or a test in a model animal or mammal such as a mouse, a rat, a dog, or a pig, etc., and such test methods are known to those skilled in the art. The methods of this invention can be applicable to any animal, including humans.

The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units.

This invention also relates to a process for producing an agent or composition for suppressing GST-π and p21, and the use of a composition that suppresses GST-π and p21 for reducing or shrinking malignant tumors.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797; Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A double stranded RNA (dsRNA) which is a Dicer substrate can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

Methods of Use of RNAi Molecules

The nucleic acid molecules and RNAi molecules of this invention may be delivered to a cell or tissue by direct application of the molecules, or with the molecules combined with a carrier or a diluent.

The nucleic acid molecules and RNAi molecules of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of this invention can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

A inhibitory nucleic acid molecule or composition of this invention may be administered within a pharmaceutically-acceptable diluents, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct, where the dsRNA is active in RNA interference.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

In one embodiment of the above method, the inhibitory nucleic acid molecule is administered at a dosage of about 5 to 500 mg/m$^2$/day, e.g., 5, 25, 50, 100, 125, 150, 175, 200, 225, 250, 275, or 300 mg/m$^2$/day.

In some embodiments, the inhibitory nucleic acid molecules of this invention are administered systemically in dosages from about 1 to 100 mg/kg, e.g., 1, 5, 10, 20, 25, 50, 75, or 100 mg/kg.

In further embodiments, the dosage can range from about 25 to 500 mg/m$^2$/day.

Methods known in the art for making formulations are found, for example, in "Remington: The Science and Practice of Pharmacy" Ed. A. R. Gennaro, Lippincourt Williams & Wilkins, Philadelphia, Pa., 2000.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleotide oligomer of the invention can depend on such variables as the type and extent of the disorder, the overall health status of the particular patient, the formulation of the compound excipients, and its route of administration.

All of the above methods for reducing malignant tumors may be either an in vitro method or an in vivo method. Dosage may be determined by an in vitro test using cultured cells, etc., as is known in the art. An effective amount may be an amount that reduces tumor size in KRAS associated tumors by at least 10%, at least 20%, or at least 30%, or at least 40%, or at least 50%, or at least 60%, or at least 70%, or at least 80%, or at least 90%, up to 100% of the tumor size.

A pharmaceutical composition of this invention can be effective in treating a KRAS associated disease. Examples of the diseases include a disease due to abnormal cell proliferation, a disease due to KRAS mutation, and a disease due to GST-π overexpression.

Examples of the disease due to abnormal cell proliferation include malignant tumors, hyperplasia, keloid, Cushing's syndrome, primary aldosteronism, erythroplakia, polycythemia vera, leukoplakia, hyperplastic scar, lichen planus, and lentiginosis.

Examples of the disease due to KRAS mutation include malignant tumor (also called a cancer or a malignant neoplasm).

Examples of the disease due to GST-π overexpression include malignant tumor.

Examples of cancer include sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, carcinomas such as brain tumor, head and neck carcinoma, breast carcinoma, lung carcinoma, esophageal carcinoma, gastric carcinoma, duodenal carcinoma, appendiceal carcinoma, colon carcinoma, rectal carcinoma, liver carcinoma, kidney carcinoma, pancreatic carcinoma, gall bladder carcinoma, bile duct carcinoma, renal carcinoma, ureteral carcinoma, bladder carcinoma, prostate carcinoma, testicular carcinoma, uterine carcinoma, ovarian carcinoma, skin carcinoma, leukemia, and malignant lymphoma.

Cancer includes epithelial malignancy and non-epithelial malignancy. A cancer can be present at any site of the body.

In one embodiment of the present invention, the cancer includes cancer cells having the mutated KRAS defined above. In another embodiment, the cancer includes cancer cells that exhibit hormone- or growth factor-independent proliferation. In further embodiments, a cancer includes cancer cells exhibiting GST-π overexpression.

Additional Active Agents or Drugs for Suppressing GST-π

Examples of additional active agents for inhibiting the activity of GST-pi include, but are not limited to, substances binding to GST-pi, for example, glutathione, glutathione analogs (e.g., those described in WO95/08563, WO96/40205, WO99/54346), ketoprofen, indomethacin (see, e.g., Hall et al., Cancer Res. 1989; 49 (22): 6265-8), ethacrynic acid, piriprost (see, e.g., Tew et al., Cancer Res. 1988; 48 (13): 3622-5), anti-GST-pi antibodies, and dominant negative mutants of GST-π. These agents are either commercially available or can be appropriately produced on the basis of publicly known techniques.

Formulations with Three Components for Delivery of Agents in Malignant Tumor

As used herein, a component of a formulation, such as a "lipid," can be a single compound, or can be a combination of one or more suitable lipid compounds. For example, "a stabilizer lipid" can refer to a single stabilizer lipid, or to a combination of one or more suitable stabilizer lipids. One skilled in the art can readily appreciate that certain combinations of the compounds described herein can be used without undue experimentation, and that various combinations of compounds are encompassed by the description of a component of a formulation.

This invention can provide a composition for use in distributing an active agent in cells, tissues or organs, organisms, and subjects, where the composition includes one or more ionizable lipid molecules of this invention.

Compositions of this invention may include one or more of the ionizable lipid molecules, along with a structural lipid, and one or more lipids for reducing immunogenicity of the nanoparticles.

An ionizable lipid molecule of this invention can be any mol % of a composition of this invention.

The ionizable lipid molecules of a composition of this invention can be from 50 mol % to 80 mol % of the lipid components of the composition. In certain embodiments, the ionizable lipid molecules of a composition can be from 55 mol % to 65 mol % of the lipid components of the composition. In further embodiments, the ionizable lipid molecules of a composition can be about 60 mol % of the lipid components of the composition.

The structural lipid of a composition of this invention can be from 20 mol % to 50 mol % of the lipid components of the composition. In certain embodiments, the structural lipid of a composition can be from 35 mol % to 45 mol % of the lipid components of the composition.

The one or more lipids for reducing immunogenicity of the nanoparticles can be from a total of 1 mol % to 8 mol % of the lipid components of the composition. In certain embodiments, the one or more lipids for reducing immunogenicity of the nanoparticles can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable lipid molecules of a composition of this invention can be from 5:80 to 25:50.

In compositions of this invention, the entirety of the lipid components may include one or more of the ionizable lipid molecular components, one or more structural lipids, and one or more lipids for reducing immunogenicity of the nanoparticles.

Formulations with Four Components for Delivery of Agents in Malignant Tumor

This invention can provide a composition for use in distributing an active agent in cells, tissues or organs, organisms, and subjects, where the composition includes one or more ionizable lipid molecules of this invention.

Compositions of this invention may include one or more of the ionizable lipid molecules, along with a structural lipid, one or more stabilizer lipids, and one or more lipids for reducing immunogenicity of the nanoparticles.

An ionizable lipid molecule of this invention can be any mol % of a composition of this invention.

The ionizable lipid molecules of a composition of this invention can be from 15 mol % to 40 mol % of the lipid components of the composition. In certain embodiments, the ionizable lipid molecules of a composition can be from 20 mol % to 35 mol % of the lipid components of the composition. In further embodiments, the ionizable lipid molecules of a composition can be from 25 mol % to 30 mol % of the lipid components of the composition.

The structural lipid of a composition of this invention can be from 25 mol % to 40 mol % of the lipid components of the composition. In certain embodiments, the structural lipid of a composition can be from 30 mol % to 35 mol % of the lipid components of the composition.

The sum of the stabilizer lipids of a composition of this invention can be from 25 mol % to 40% mol % of the lipid components of the composition. In certain embodiments, the sum of the stabilizer lipids of a composition can be from 30 mol % to 40 mol % of the lipid components of the composition.

In some embodiments, a composition of this invention can include two or more stabilizer lipids, where each of the stabilizer lipids individually can be from 5 mol % to 35 mol % of the lipid components of the composition. In certain embodiments, a composition of this invention can include two or more stabilizer lipids, where each of the stabilizer lipids individually can be from 10 mol % to 30 mol % of the lipid components of the composition.

In certain embodiments, the sum of the one or more stabilizer lipids can be from 25 mol % to 40 mol % of the lipids of the composition, wherein each of the stabilizer lipids individually can be from 5 mol % to 35% mol %.

In certain embodiments, the sum of the one or more stabilizer lipids can be from 30 mol % to 40 mol % of the lipids of the composition, wherein each of the stabilizer lipids individually can be from 10 mol % to 30% mol %.

The one or more lipids for reducing immunogenicity of the nanoparticles can be from a total of 1 mol % to 8 mol % of the lipid components of the composition. In certain embodiments, the one or more lipids for reducing immunogenicity of the nanoparticles can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable lipid molecules of a composition of this invention can be from 5:35 to 25:15.

In compositions of this invention, the entirety of the lipid components may include one or more of the ionizable lipid molecular components, one or more structural lipids, one or more stabilizer lipids, and one or more lipids for reducing immunogenicity of the nanoparticles.

Examples of Lipid Compositions

In some embodiments, three lipid-like components, i.e. one or more ionizable molecules, a structural lipid, and one or more lipids for reducing immunogenicity of the nanoparticles can be 100% of the lipid components of the composition. In certain embodiments, a cationic lipid can be included.

Examples of compositions of this invention are shown in Table 9.

TABLE 9

| Compositions of lipid components (each in mol % of total) | | | |
|---|---|---|---|
| Ionizable | Cationic | Structural | Reduce immun. |
| 60 | 0 | 32 | 8 |
| 60 | 0 | 35 | 5 |
| 55 | 0 | 44 | 1 |
| 65 | 0 | 32 | 3 |
| 60 | 0 | 36 | 4 |
| 65 | 0 | 32 | 3 |

TABLE 9-continued

Compositions of lipid components (each in mol % of total)

| Ionizable | Cationic | Structural | Reduce immun. |
|---|---|---|---|
| 70 | 0 | 25 | 5 |
| 74 | 0 | 20 | 6 |
| 78 | 0 | 20 | 2 |
| 50 | 10 | 35 | 5 |
| 55 | 15 | 25 | 5 |
| 55 | 20 | 20 | 5 |

In certain embodiments, the four lipid-like components, i.e. one or more ionizable lipid molecules, a structural lipid, one or more stabilizer lipids, and one or more lipids for reducing immunogenicity of the nanoparticles, can be 100% of the lipid components of the composition.

Examples of compositions of this invention are shown in Table 10.

TABLE 10

Compositions of lipid components (each in mol % of total)

| Ionizable | Cationic | Structural | Stabilizer | Reduce immun. |
|---|---|---|---|---|
| 17 | 0 | 35 | 40 | 8 |
| 20 | 0 | 35 | 40 | 5 |
| 25 | 0 | 35 | 39 | 1 |
| 25 | 0 | 35 | 35 | 5 |
| 25 | 0 | 30 | 40 | 5 |
| 25 | 0 | 40 | 30 | 5 |
| 30 | 0 | 25 | 40 | 5 |
| 35 | 0 | 25 | 35 | 5 |
| 40 | 0 | 30 | 25 | 5 |
| 25 | 5 | 30 | 35 | 5 |
| 25 | 10 | 30 | 30 | 5 |
| 25 | 15 | 25 | 30 | 5 |

Ionizable Lipid-Like Molecules

Examples of on ionizable lipid include compounds having the structure shown in Formula I

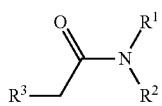

Formula I wherein $R^1$ and $R^2$ are $R^1 = CH_2(CH_2)_n OC(=O)R^4$ $R^2 = CH_2(CH_2)_m OC(=O)R^5$ wherein n and m are from 1 to 2; and $R^4$ and $R^5$ are independently for each occurrence a C(12-20) alkyl group, or a C(12-20) alkenyl group having from zero to two double bonds;

wherein $R^3$ is selected from

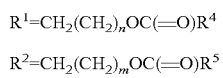

wherein $R^6$ is selected from H, alkyl, hydroxyalkyl, alkoxy, alkoxyalkoxy, aminoalkyl;

$R^7$ is selected from H, alkyl, hydroxyalkyl;

Q is O or $NR^7$;

p is from 1 to 4.

Examples of on ionizable lipid include the following compound:

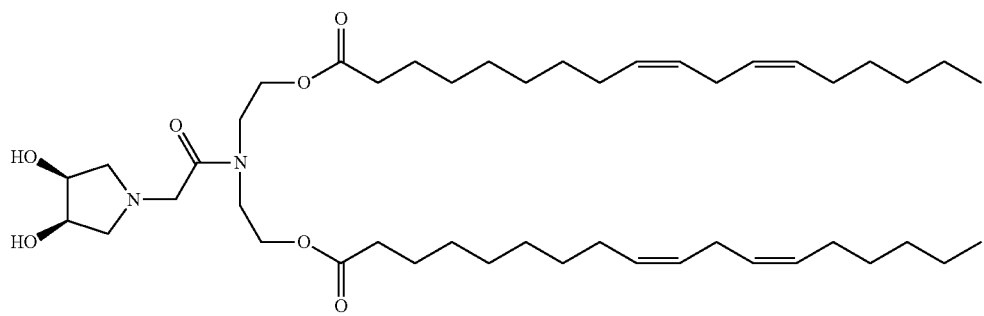

COMPOUND 81 which is ((2-((3S,4R)-3,4-dihydroxypyrrolidin-1-yl)acetyl)azanediyl)bis(ethane-2,1-diyl) (9Z,9'Z,12Z,12'Z)-bis(octadeca-9,12-dienoate).

Examples of on ionizable lipid include the following compound:

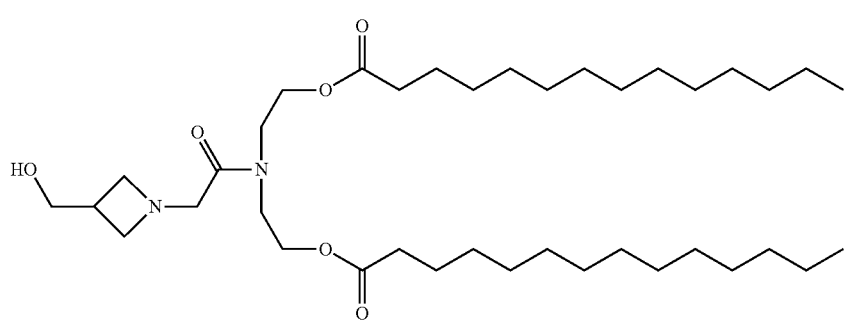

COMPOUND 71 which is ((2-(3-(hydroxymethyl)azetidin-1-yl)acetyl)azanediyl)bis(ethane-2,1-diyl) ditetradecanoate.

Examples of on ionizable lipid include the following compound:

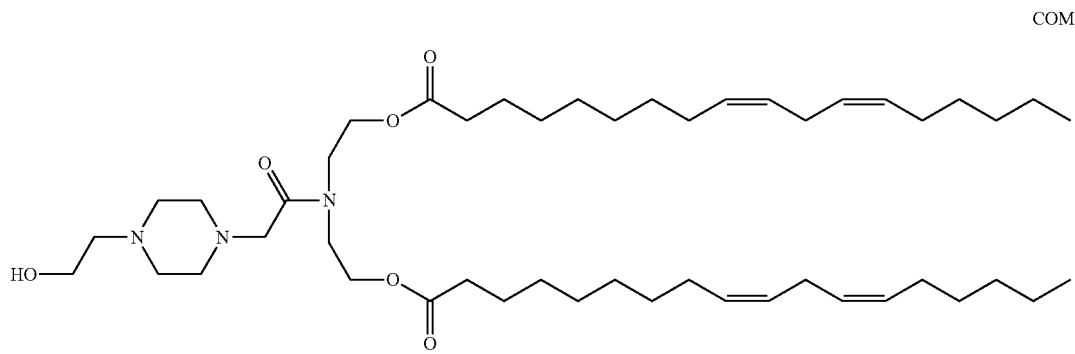

COMPOUND 57 which is ((2-(4-(2-hydroxyethyl)piperazin-1-yl)acetyl)azanediyl)bis(ethane-2,1-diyl) (9Z,9'Z,12Z,12'Z)-bis(octadeca-9,12-dienoate).

Examples of on ionizable lipid include the following compound:

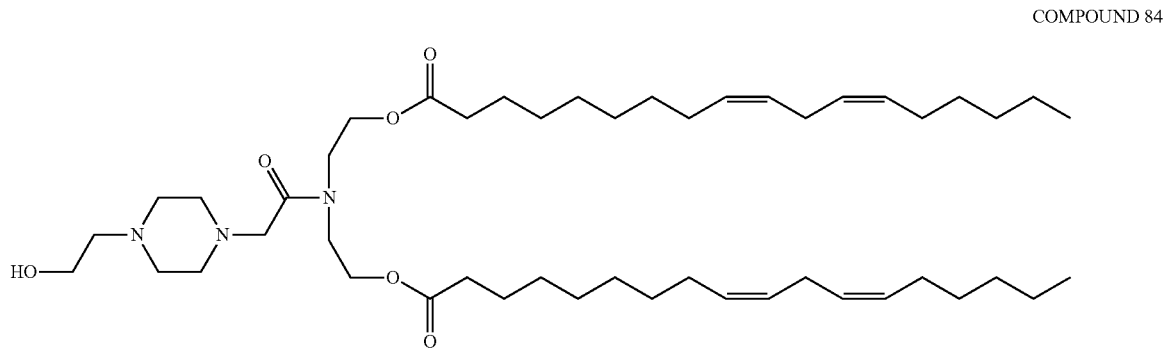 [SMILES: CCCCC/C=C\C/C=C\CCCCCCCC(=O)OCCN(CCOC(=O)CCCCCCC/C=C\C/C=C\CCCCC)C(=O)CN1CCN(CCO)CC1]

COMPOUND 84 which is ((2-(4-(2-hydroxyethyl)piperazin-1-yl)acetyl) azanediyl)bis(ethane-2,1-diyl) (9Z,9'Z,12Z,12'Z)-bis(octadeca-9,12-dienoate).

Examples of on ionizable lipid include compounds having the structure shown in Formula IV

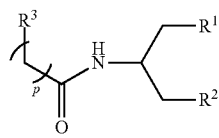

Formula IV wherein $R^1$ and $R^2$ are $R^1 = C(=O)OR^4$ $R^2 = C(=O)OR^5$ wherein $R^4$ and $R^5$ are independently for each occurrence a C(12-20) alkyl group, or a C(12-20) alkenyl group having from zero to two double bonds;

wherein $R^3$ is selected from

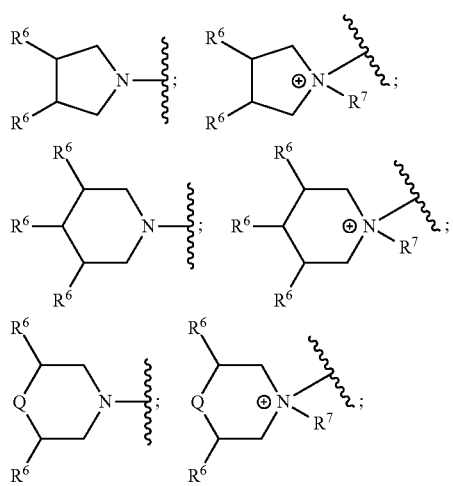

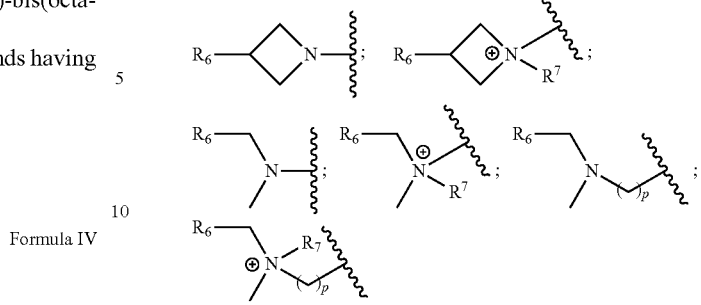

wherein $R^6$ is selected from H, alkyl, hydroxyalkyl, alkoxy, alkoxyalkoxy, aminoalkyl;

$R^7$ is selected from H, alkyl, hydroxyalkyl;

Q is O or $NR^7$;

p is from 1 to 4.

Examples of on ionizable lipid include the following compound:

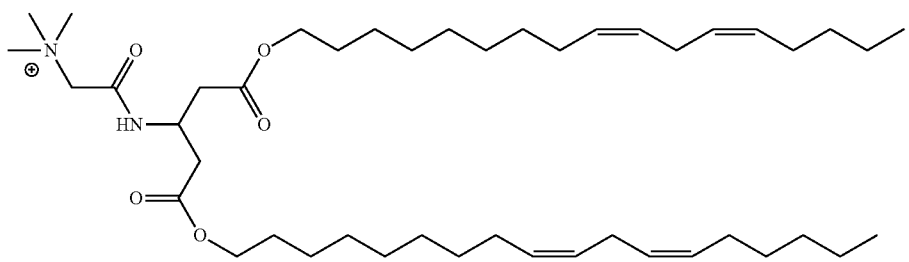

COMPOUND 49 which is 2-((1-(((9Z,12Z)-heptadeca-9,12-dien-1-yl)oxy)-5-(((9Z,12Z)-octadeca-9,12-dien-1-yl)oxy)-1,5-dioxopentan-3-yl)amino)-N,N,N-trimethyl-2-oxoethan-1-aminium.

Examples of on ionizable lipid include compounds having the structure shown in Formula VI

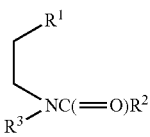

Formula VI wherein $R^1$ is $R^1 = OC(=O)R^4$ wherein $R^2$ and $R^4$ are independently for each occurrence a C(12-20) alkyl group, or a C(12-20) alkenyl group having from zero to two double bonds;

wherein $R^3$ is selected from aminoalkyl, quaternary aminoalkyl.

Examples of on ionizable lipid include the following compound:

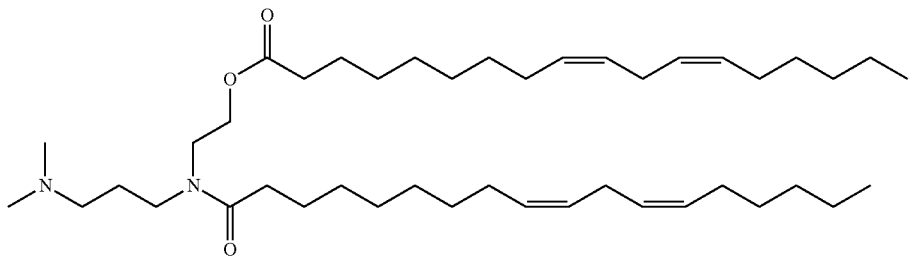

COMPOUND 76 which is 2-((9Z,12Z)—N-(3-(dimethylamino)propyl)octadeca-9,12-dienamido)ethyl (9Z,12Z)-octadeca-9,12-dienoate.

Examples of on ionizable lipid include the following compound:

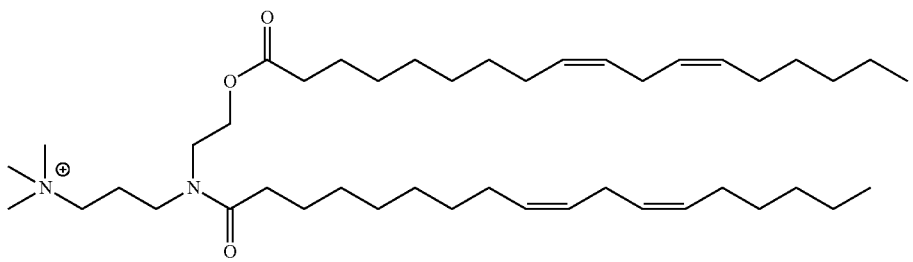

COMPOUND 78 which is N,N,N-trimethyl-3-((9Z,12Z)—N-(2-(((9Z,12Z)-octadeca-9,12-dienoyl)oxy)ethyl)octadeca-9,12-dienamido)propan-1-aminium.

Examples of on ionizable lipid include compounds having the structure shown in Formula IX Formula IX

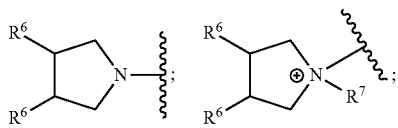

wherein $R^1$ and $R^2$ are $R^1=C(=O)OR^4$ $R^2=NHC(=O)R^5$ wherein $R^4$ and $R^5$ are independently for each occurrence a C(12-20) alkyl group, or a C(12-20) alkenyl group having from zero to two double bonds;

wherein r is from 1 to 4;

wherein $R^3$ is selected from wherein
$R^6$ is selected from H, alkyl, hydroxyalkyl, alkoxy, alkoxyalkoxy, aminoalkyl;
$R^7$ is selected from H, alkyl, hydroxyalkyl;
Q is O or $NR^7$.

Examples of on ionizable lipid include the following compound:

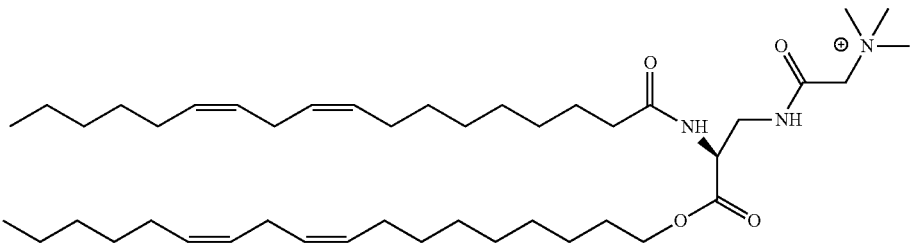

COMPOUND 102 which is N,N,N-trimethyl-2-(((S)-3-(((9Z,12Z)-octadeca-9,12-dien-1-yl)oxy)-2-((9Z,12Z)-octadeca-9,12-dienamido)-3-oxopropyl)amino)-2-oxoethan-1-aminium.

Examples of on ionizable lipid molecule include compounds having the structure shown in Formula III

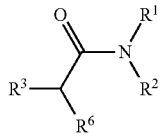

Formula III wherein $R^1$ and $R^2$ are

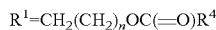

$R^1=CH_2(CH_2)_nOC(=O)R^4$

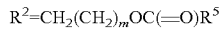

$R^2=CH_2(CH_2)_mOC(=O)R^5$ wherein n and m are from 1 to 2; and $R^4$ and $R^5$ are independently for each occurrence a C(12-20) alkyl group, or a C(12-20) alkenyl group;
wherein $R^3$ is selected from alkyl, hydroxyalkyl, alkoxyalkoxy, and carboxyalkyl;
wherein $R^6$ is selected from $NR^7_2$, $N^+HR^7_2$ and $N^+R^7_3$;
wherein $R^7$ is selected from H, alkyl, hydroxyalkyl.

Examples of on ionizable lipid molecule include compounds having the structure shown in Formula IV-B

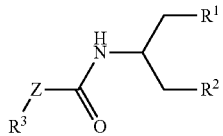

Formula IV-B wherein $R^1$ and $R^2$ are

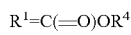

$R^1=C(=O)OR^4$

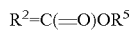

$R^2=C(=O)OR^5$ wherein $R^4$ and $R^5$ are independently for each occurrence a C(12-20) alkyl group, or a C(12-20) alkenyl group;
wherein Z is S or O;
wherein $R^3$ is selected from

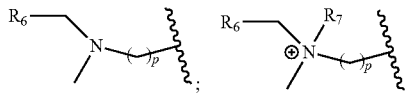

wherein
each $R^6$ is independently selected from H, alkyl, hydroxyalkyl, alkoxy, alkoxyalkoxy, aminoalkyl;
$R^7$ is selected from H, alkyl, hydroxyalkyl;
p is from 1 to 4.

Examples of on ionizable lipid molecule include compounds having the structure shown in Formula V

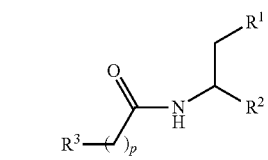

Formula V wherein $R^1$ and $R^2$ are

$R^1=NHC(=O)R^4$

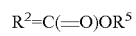

$R^2=C(=O)OR^5$ wherein $R^4$ and $R^5$ are independently for each occurrence a C(12-20) alkyl group, or a C(12-20) alkenyl group;
wherein p is from 1 to 4;
wherein $R^3$ is selected from

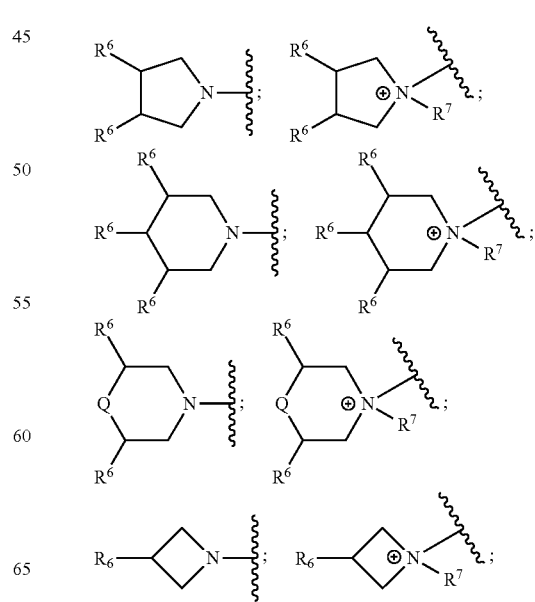

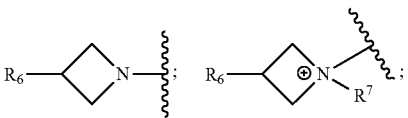

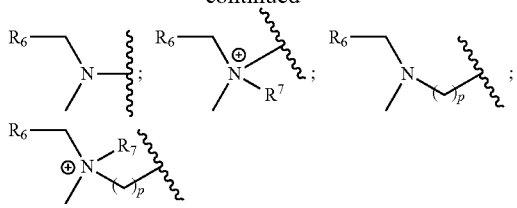

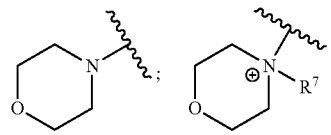

wherein each $R^6$ is independently selected from H, alkyl, hydroxyalkyl, alkoxy, alkoxyalkoxy, aminoalkyl;

$R^7$ is selected from H, alkyl, hydroxyalkyl;

Q is O or $NR^7$.

Examples of on ionizable lipid molecule include compounds having the structure shown in Formula VII

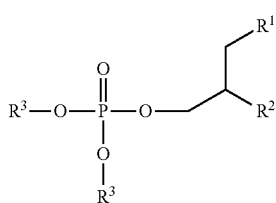

Formula VII wherein $R^1$ and $R^2$ are $R^1=CH_2(CH_2)_nOC(=O)R^4$ $R^2=CH_2(CH_2)_mOC(=O)R^5$ wherein n and m are from 1 to 2; and $R^4$ and $R^5$ are independently for each occurrence a C(12-20) alkyl group, or a C(12-20) alkenyl group;

wherein $R^3$ is selected from aminoalkyl, quaternary aminoalkyl, alkoxyalkyl, alkoxyalkoxyalkyl.

Examples of on ionizable lipid molecule include compounds having the structure shown in Formula VIII

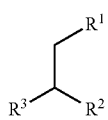

Formula VIII wherein $R^1$ and $R^2$ are $R^1=OC(=O)R^4$ $R^2=C(=O)ZR^5$ wherein Z is NH or O, wherein $R^4$ and $R^5$ are independently for each occurrence a C(12-20) alkyl group, or a C(12-20) alkenyl group;

wherein $R^3$ is selected from amino;

quaternary amino;

aminoalkyl;

quaternary aminoalkyl;

$NHC(=O)(CH_2)_pR^8$;

$NHC(=O)SR^9$;

wherein $R^8$ is selected from

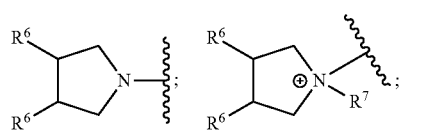

carboxyalkyl;

aminoalkyl;

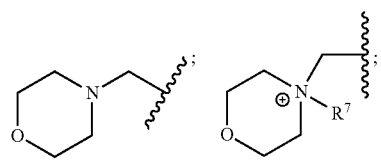

wherein $R^9$ is selected from aminoalkyl;

and wherein each $R^6$ is independently selected from H, alkyl, hydroxyalkyl, alkoxy, alkoxyalkoxy, aminoalkyl;

$R^7$ is selected from H, alkyl, hydroxyalkyl;

Q is O or $NR^7$.

Examples of on ionizable lipid molecule include compounds having the structure shown in Formula VIII-B

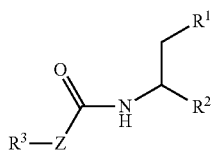

Formula VIII-B wherein $R^1$ and $R^2$ are

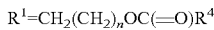
$R^1 = CH_2(CH_2)_n OC(=O)R^4$

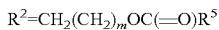
$R^2 = CH_2(CH_2)_m OC(=O)R^5$ wherein n and m are from 1 to 2;
$R^4$ and $R^5$ are independently for each occurrence a C(12-20) alkyl group, or a C(12-20) alkenyl group;
wherein Z is N, O;
wherein $R^3$ is selected from

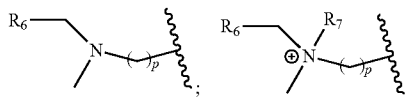

wherein
each $R^6$ is independently selected from H, alkyl, hydroxyalkyl, alkoxy, alkoxyalkoxy, aminoalkyl;
$R^7$ is selected from H, alkyl, hydroxyalkyl;
p is from 1 to 4.

Examples of on ionizable lipid molecule include compounds having the structure shown in Formula X

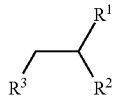

Formula X wherein $R^1$ and $R^2$ are

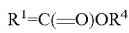
$R^1 = C(=O)OR^4$

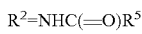
$R^2 = NHC(=O)R^5$ wherein $R^4$ and $R^5$ are independently for each occurrence a C(12-20) alkyl group, or a C(12-20) alkenyl group;
wherein $R^3$ is selected from
  amino;
  quaternary amino;
  aminoalkyl;
  quaternary aminoalkyl;
  hydroxyalkylamino;
  quaternary hydroxyalkylamino.

Examples of on ionizable lipid molecule include compounds having the structure shown in Formula XI

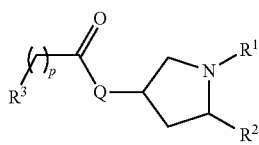

Formula XI wherein $R^1$ and $R^2$ are

$R^1 = C(=O)R^4$

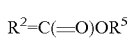
$R^2 = C(=O)OR^5$ wherein $R^4$ and $R^5$ are independently for each occurrence a C(12-20) alkyl group, or a C(12-20) alkenyl group;
wherein p is from 1 to 4;
wherein $R^3$ is selected from

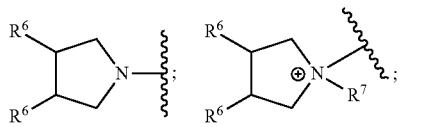

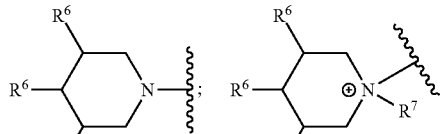

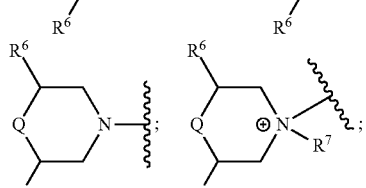

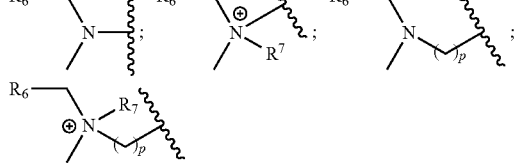

wherein
each $R^6$ is independently selected from H, alkyl, hydroxyalkyl, alkoxy, alkoxyalkoxy, aminoalkyl;
$R^7$ is selected from H, alkyl;
Q is O or $NR^7$.

Structural Lipids

Examples of structural lipids include cholesterols, sterols, and steroids.

Examples of structural lipids include cholanes, cholestanes, ergostanes, campestanes, poriferastanes, stigmastanes, gorgostanes, lanostanes, gonanes, estranes, androstanes, pregnanes, and cycloartanes.

Examples of structural lipids include sterols and zoosterols such as cholesterol, lanosterol, zymosterol, zymostenol, desmosterol, stigmastanol, dihydrolanosterol, and 7-dehydrocholesterol.

Examples of structural lipids include pegylated cholesterols, and cholestane 3-oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of structural lipids include sterols such as phytosterols, beta-sitosterol, campesterol, ergosterol, brassicasterol, delta-7-stigmasterol, and delta-7-avenasterol.

Stabilizer Lipids

Examples of stabilizer lipids include zwitterionic lipids.

Examples of stabilizer lipids include compounds such as phospholipids.

Examples of phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and ordilinoleoylphosphatidylcholine.

Examples of stabilizer lipids include phosphatidyl ethanolamine compounds and phosphatidyl choline compounds.

Examples of stabilizer lipids include 1,2-Dioleoyl-sn-Glycero-3-Phosphocholine (DOPC).

Examples of stabilizer lipids include diphytanoyl phosphatidyl ethanolamine (DPhPE) and 1,2-Diphytanoyl-sn-Glycero-3-Phosphocholine (DPhPC).

Examples of stabilizer lipids include 1,2-distearoyl-sn-glycero-3-phosphocholine (DSPC), 1,2-dipalmitoyl-sn-glycero-3-phosphocholine (DPPC), 1,2-dipalmitoyl-sn-glycero-3-phosphoethanolamine (DPPE), and 1,2-dioleoyl-sn-glycero-3-phosphoethanolamine (DOPE).

Examples of stabilizer lipids include 1,2-dilauroyl-sn-glycerol (DLG); 1,2-dimyristoyl-sn-glycerol (DMG); 1,2-dipalmitoyl-sn-glycerol (DPG); 1,2-distearoyl-sn-glycerol (DSG); 1,2-diarachidoyl-sn-glycero-3-phosphocholine (DAPC); 1,2-dilauroyl-sn-glycero-3-phosphocholine (DLPC); 1,2-dimyristoyl-sn-glycero-3-phosphocholine (DMPC); 1,2-dipalmitoyl-sn-glycero-O-ethyl-3-phosphocholine (DPePC); 1,2-dilauroyl-sn-glycero-3-phosphoethanolamine (DLPE); 1,2-dimyristoyl-sn-glycero-3-phosphoethanolamine (DMPE); 1,2-distearoyl-sn-glycero-3-phosphoethanolamine (DSPE); 1-palmitoyl-2-linoleoyl-sn-glycero-3-phosphocholine; 1-palmitoyl-2-oleoyl-sn-glycero-3-phosphocholine (POPC); 1-palmitoyl-2-lyso-sn-glycero-3-phosphocholine (P-Lyso-PC); and 1-Stearoyl-2-lyso-sn-glycero-3-phosphocholine (S-Lyso-PC).

Lipids for Reducing Immunogenicity

Examples of lipids for reducing immunogenicity include polymeric compounds and polymer-lipid conjugates.

Examples of lipids for reducing immunogenicity include pegylated lipids having polyethyleneglycol (PEG) regions. The PEG regions can be of any molecular mass. In some embodiments, a PEG region can have a molecular mass of 200, 300, 350, 400, 500, 550, 750, 1000, 1500, 2000, 3000, 3500, 4000 or 5000 Da.

Examples of lipids for reducing immunogenicity include compounds having a methoxypolyethyleneglycol region.

Examples of lipids for reducing immunogenicity include compounds having a carbonyl-methoxypolyethyleneglycol region.

Examples of lipids for reducing immunogenicity include compounds having a multi-branched PEG region.

Examples of lipids for reducing immunogenicity include compounds having a polyglycerine region.

Examples of lipids for reducing immunogenicity include polymeric lipids such as DSPE-mPEG, DMPE-mPEG, DPPE-mPEG, and DOPE-mPEG.

Examples of lipids for reducing immunogenicity include PEG-phospholipids and PEG-ceramides.

Cationic Lipids

Examples of cationic lipids include cationic HEDC compounds as described in US 2013/0330401 A1. Some examples of cationic lipids are given in US 2013/0115274 A1. Additional examples of cationic lipids are known in the art.

Lipid Compositions

In some embodiments, a composition can contain the ionizable lipid compound 81, the structural lipid cholesterol, the stabilizer lipids DOPC and DOPE, and the lipid for reducing immunogenicity DPPE-mPEG. In certain embodiments, compound 81 can be 15 to 25 mol % of the composition; the cholesterol, DOPC, and DOPE combined can be 75 to 85 mol % of the composition; and DPPE-mPEG can be 5 mol % of the composition.

In one embodiment, compound 81 can be 25 mol % of the composition; cholesterol can be 30 mol % of the composition, DOPC can be 20 mol % of the composition, DOPE can be 20 mol % of the composition; and DPPE-mPEG(2000) can be 5 mol % of the composition.

Nanoparticles

Embodiments of this invention can provide liposome nanoparticle compositions. The ionizable molecules of this invention can be used to form liposome compositions, which can have a bilayer of lipid-like molecules.

A nanoparticle composition can have one or more of the ionizable molecules of this invention in a liposomal structure, a bilayer structure, a micelle, a lamellar structure, or a mixture thereof.

In some embodiments, a composition can include one or more liquid vehicle components. A liquid vehicle suitable for delivery of active agents of this invention can be a pharmaceutically acceptable liquid vehicle. A liquid vehicle can include an organic solvent, or a combination of water and an organic solvent.

Embodiments of this invention can provide lipid nanoparticles having a size of from 10 to 1000 nm. In some embodiments, the liposome nanoparticles can have a size of from 10 to 150 nm.

In certain embodiments, the liposome nanoparticles of this invention can encapsulate the RNAi molecule and retain at least 80% of the encapsulated RNAi molecules after 1 hour exposure to human serum.

Pharmaceutical Compositions

This invention further contemplates methods for distributing an active agent to an organ of a subject for treating malignant tumor by administering to the subject a composition of this invention. Organs that can be treated include lung, liver, pancreas, kidney, colon, bone, skin, and intestine.

In some embodiments, this invention provides methods for treating a lung malignant tumor disease by administering to the subject a composition of this invention.

In further aspects, this invention provides a range of pharmaceutical formulations.

A pharmaceutical formulation herein can include an active agent, as well as a drug carrier, or a lipid of this invention, along with a pharmaceutically acceptable carrier or diluent. In general, active agents of this description include any active agents for malignant tumor, including any inhibitory nucleic acid molecules and any small molecular drugs. Examples of inhibitory nucleic acid molecules include ribozymes, anti-sense nucleic acids, and RNA interference molecules (RNAi molecules).

Examples of anti-malignant tumor and anti-cancer drugs include oncogenes-related factors, tumor angiogenesis factor, metastatic related factors, cytokines such as TGF-Beta, growth factor, proteinase such as MMP, caspase, and immunization suppression factor.

A drug carrier may target a composition to reach stellate cells. A drug carrier may include a drug in its interior, or be attached to the exterior of a drug-containing substance, or be mixed with a drug so long as a retinoid derivative and/or vitamin A analogue is included in the drug carrier, and is at least partially exposed on the exterior of the preparation. The composition or preparation may be covered with an appropriate material, such as, for example, an enteric coating or a material that disintegrates over time, or may be incorporated into an appropriate drug release system.

A pharmaceutical formulation of this invention may contain one or more of each of the following: a surface active agent, a diluent, an excipient, a preservative, a stabilizer, a dye, and a suspension agent.

Some pharmaceutical carriers, diluents and components for a pharmaceutical formulation, as well as methods for formulating and administering the compounds and compositions of this invention are described in Remington's Pharmaceutical Sciences, 18th Ed., Mack Publishing Co., Easton, Pa. (1990).

Examples of preservatives include sodium benzoate, ascorbic acid, and esters of p-hydroxybenzoic acid.

Examples of surface active agents include alcohols, esters, sulfated aliphatic alcohols.

Examples of excipients include sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, and calcium carboxymethyl cellulose.

Examples of suspension agents include coconut oil, olive oil, sesame oil, peanut oil, soya, cellulose acetate phthalate, methylacetate-methacrylate copolymer, and ester phthalates.

A therapeutic formulation of this invention for the delivery of one or more molecules active for gene silencing can be administered to a mammal in need thereof. A therapeutically effective amount of the formulation and active agent, which may be encapsulated in a liposome, can be administered to a mammal for preventing or treating malignant tumor.

The route of administration may be local or systemic.

A therapeutically-effective formulation of this invention can be administered by various routes, including intravenous, intraperitoneal, intramuscular, subcutaneous, and oral.

Routes of administration may include, for example, parenteral delivery, including intramuscular, subcutaneous, intravenous, intramedullary injections, as well as intrathecal, direct intraventricular, intraperitoneal, intranasal, or intraocular injections.

The formulation can also be administered in sustained or controlled release dosage forms, including depot injections, osmotic pumps, and the like, for prolonged and/or timed, pulsed administration at a predetermined rate.

The composition of the present invention may be administered via various routes including both oral and parenteral routes, and examples thereof include, but are not limited to, oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes, and it may be formulated into a dosage form suitable for each administration route. Such a dosage form and formulation method may be selected as appropriate from any known dosage forms and methods. See e.g. Hyojun Yakuzaigaku, Standard Pharmaceutics, Ed. by Yoshiteru Watanabe et al., Nankodo, 2003.

Examples of dosage forms suitable for oral administration include, but are not limited to, powder, granule, tablet, capsule, liquid, suspension, emulsion, gel, and syrup, and examples of the dosage form suitable for parenteral administration include injections such as an injectable solution, an injectable suspension, an injectable emulsion, and a ready-to-use injection. Formulations for parenteral administration may be a form such as an aqueous or nonaqueous isotonic sterile solution or suspension.

Pharmaceutical formulations for parenteral administration, e.g., by bolus injection or continuous infusion, include aqueous solutions of the active formulation in water-soluble form. Suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Formulations for injection may be presented in unit dosage form, e.g., in ampoules or in multi-dose containers, with an added preservative. The formulations may take such forms as suspensions, solutions or emulsions in oily or aqueous vehicles, and may contain formulary agents such as suspending, stabilizing and/or dispersing agents. Alternatively, the active ingredient may be in powder form for constitution with a suitable vehicle, e.g., sterile pyrogen-free water, before use.

In addition to the preparations described previously, the formulations may also be formulated as a depot preparation. Such long acting formulations may be administered by intramuscular injection. Thus, for example, the formulation may be formulated with suitable polymeric or hydrophobic materials, for example as an emulsion in an acceptable oil, or ion exchange resins, or as sparingly soluble derivatives, for example, as a sparingly soluble salt.

Compositions and formulations of this invention may also be formulated for topical delivery and may be applied to the subject's skin using any suitable process for application of topical delivery vehicle. For example, the formulation may be applied manually, using an applicator, or by a process that involves both. Following application, the formulation may be worked into the subject's skin, e.g., by rubbing. Application may be performed multiple times daily or on a once-daily basis. For example, the formulation may be applied to a subject's skin once a day, twice a day, or multiple times a day, or may be applied once every two days, once every three days, or about once every week, once every two weeks, or once every several weeks.

The formulations or pharmaceutical compositions described herein may be administered to the subject by any suitable means. Examples of methods of administration include, among others, (a) administration via injection, subcutaneously, intraperitoneally, intravenously, intramuscularly, intradermally, intraorbitally, intracapsularly, intraspinally, intrasternally, or the like, including infusion pump delivery; (b) administration locally such as by injection directly in the renal or cardiac area, e.g., by depot implantation; as well as deemed appropriate by those of skill in the art for bringing the active compound into contact with living tissue.

The exact formulation, route of administration and dosage for the pharmaceutical compositions can be chosen by the individual physician in view of the patient's condition. See, e.g., Goodman & Gilman's The Pharmacological Basis of Therapeutics, $12^{th}$ Ed., Sec. 1, 2011. Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from ED50 or ID50 values, or other appropriate values derived from in vitro or in vivo studies, as qualified by toxicity studies and efficacy studies in animals.

Methods for Preventing or Treating Malignant Tumor

The present invention further relates to a method for controlling the activity or growth of malignant tumors, the method including administering an effective amount of the composition to a subject in need thereof. The effective amount referred to here is, in a method for treating malignant tumor, alleviates its symptoms, or delays or stops its progression, and is preferably an amount that prevents the onset or recurrence of malignant tumor, or cures it. It is also preferably an amount that does not cause an adverse effect that exceeds the benefit from administration. Such an amount may be determined as appropriate by an in vitro test using cultured cells or by a test in a model animal or mammal such as a mouse, a rat, a dog, or a pig, and such test methods are well known to a person skilled in the art. Moreover, the dose of the active agents in the carrier and the dose of the active agents used in the method of the present invention are known to a person skilled in the art, or may be determined as appropriate by the above-mentioned tests.

The frequency of administration depends on the properties of the composition used and the above-mentioned conditions of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every other week, or every few weeks (that is, every 2, 3, 4 weeks, etc.).

In some embodiments, he present invention also relates to a method for delivering a drug to a malignant tumor cell, by utilizing the above carrier. This method includes a step of administering or adding the carrier having the substance to be delivered carried thereon to a living being or a medium, for example a culture medium, containing an extracellular matrix-producing cell in the lung. These steps may be achieved as appropriate in accordance with any known method or a method described in this invention. Moreover, the above method includes a mode carried out in vitro and a mode in which a malignant tumor cell in the lung inside the body is targeted.

A therapeutically-effective formulation of this invention can be administered by systemic delivery that can provide a broad biodistribution of the active agent.

Embodiments of this invention can provide a therapeutic formulation, which includes an inventive therapeutic molecule and a pharmaceutically-acceptable carrier.

An effective dose of a formulation of this invention may be administered from 1 to 12 times per day, or once per week. The duration of administration can be 1, 2, 3, 4, 5, 6 or 7 days, or can be 1, 2, 3, 4, 5, 6, 8, 10 or 12 weeks.

Additional Embodiments

A composition for use in distributing an active agent for a treating malignant tumor in a subject, the composition comprising an ionizable lipid, a structural lipid, and a lipid for reducing immunogenicity of the nanoparticles. The malignant tumor can be located in the lung, colon, kidney or pancreas. The malignant tumor can be located in the liver, bone, skin, or intestine. The ionizable lipid can be from 50 mol % to 80 mol % of the lipids of the composition, or from 55 mol % to 65 mol % of the lipids of the composition. The structural lipid can be from 20 mol % to 50 mol % of the lipids of the composition, or from 35 mol % to 55 mol % of the lipids of the composition. The structural lipid can be a cholesterol, sterol, or steroid. The lipid for reducing immunogenicity of the nanoparticles can be from 1 mol % to 8 mol % of the lipids of the composition. The lipid for reducing immunogenicity of the nanoparticles may have a polyethyleneglycol (PEG) region having a molecular mass from 200 to 5000 Da. The lipid for reducing immunogenicity of the nanoparticles can be DPPE-mPEG, DSPE-mPEG, DMPE-mPEG, or DOPE-mPEG.

This invention further contemplates a composition for use in distributing an active agent for a treating malignant tumor in a subject, the composition comprising an ionizable lipid, a structural lipid, one or more stabilizer lipids, and a lipid for reducing immunogenicity of the nanoparticles. The ionizable lipid can be from 15 mol % to 40 mol % of the lipids of the composition, or from 20 mol % to 35 mol % of the lipids of the composition. The structural lipid can be from 25 mol % to 40 mol % of the lipids of the composition, or from 30 mol % to 35 mol % of the lipids of the composition.

The sum of the one or more stabilizer lipids can be from 25 mol % to 40 mol % of the lipids of the composition, wherein each of the stabilizer lipids individually is from 5 mol % to 35% mol %. The one or more stabilizer lipids can be phosphatidyl ethanolamine compounds or phosphatidyl choline compounds.

The composition can be (compound 81/cholesterol/DOPC/DOPE/DPPE-PEG-2000) in one of the following combinations, wherein the numerals refer to the mol % concentration of the component: (25/30/30/10/5), (25/30/25/15/5), (25/30/20/20/5), (25/30/15/25/5), (25/30/10/30/5), (25/35/15/20/5), (25/35/20/15/5), (30/30/15/20/5), (30/30/20/15/5), (35/30/15/15/5). In some embodiments, the ionizable lipid can be compound 81, the structural lipid can be cholesterol, the stabilizer lipids can be DOPC and DOPE, and the lipid for reducing immunogenicity of the nanoparticles can be DSPE-mPEG-2000, wherein compound 81 comprises 15 to 25 mol % of the composition, wherein cholesterol, DOPC, and DOPE combined comprise 75 to 85 mol % of the composition, wherein the DSPE-mPEG-2000 comprises from 1 to 5 mol % of the composition, and wherein compound 81, cholesterol, DOPC, DOPE, and the DSPE-mPEG-2000 combined comprise substantially 100 mol % of the lipids of the composition.

The active agent can be RNAi molecules targeted to GST-π and RNAi molecules targeted to p21. In some embodiments, the active agent comprises RNAi molecules targeted to GST-π and RNAi molecules targeted to p21, and the composition comprises liposome nanoparticles that encapsulate the RNAi molecules. In certain embodiments, the active agent comprises RNAi molecules targeted to GST-π and RNAi molecules targeted to p21, and the composition comprises liposome nanoparticles that encapsulate the RNAi molecules and retain at least 80% of the encapsulated RNAi molecules after 1 hour exposure to human serum.

This invention also contemplates pharmaceutical compositions comprising a lipid composition and an active agent. The active agent can be one or more RNAi molecules. The RNAi molecules for treating malignant tumor can include RNAi molecules targeted to GST-π and RNAi molecules targeted to p21. The RNAi molecules for treating malignant tumor can be, for example, siRNAs, shRNAs, or microRNAs, as well as DNA-directed RNAs (ddRNA), Piwi-interacting RNAs (piRNA), and repeat associated siRNAs (rasiRNA).

In certain embodiments, this invention provides a pharmaceutical composition containing RNAi molecules for treating malignant tumor that are RNAi molecules targeted to only GST-π.

Embodiments of this invention further include methods for distributing an active agent to an organ of a subject for treating malignant, by administering to the subject a composition of this invention. The malignant tumor can be located in the lung, colon, kidney or pancreas. The malignant tumor can be located in the liver, bone, skin, or intestine. The malignant tumor can be located in an anatomical region selected from the group consisting of head and neck, brain, breast, esophagus, stomach, intestine, duodenum, liver, gallbladder, bile duct, kidney, urethra, bladder, prostate, testis, uterus, ovary, skin, bone, bone marrow, blood, skin, and epithelial layer.

The administration can be a dose of from 0.01 to 2 mg/kg of the RNAi molecules at least once per day for a period up to twelve weeks. The administration can provide a mean AUC(0-last) of from 1 to 1000 ug*min/mL and a mean $C_{max}$ of from 0.1 to 50 ug/mL for the GST-π RNAi molecule. The administration can provide a mean plasma AUC(0-last) of from 1 to 1000 ug*min/mL and a mean plasma $C_{max}$ of from 0.1 to 50 ug/mL for the p21 RNAi molecule.

This invention provides methods for preventing, treating or ameliorating one or more symptoms of a malignant tumor in a mammal in need thereof, or any animal, the method comprising administering to the mammal a therapeutically effective amount of a composition comprising RNAi molecules, wherein a portion of the RNAi molecules are active in reducing expression of GST-π and a portion of the RNAi molecules are active in reducing expression of p21. In some embodiments, the malignant tumor is associated with KRAS mutation in the mammal, the method further comprising identifying a tumor cell in the mammal, the tumor cell comprising at least one of: (i) a mutation of the KRAS gene, and (ii) an aberrant expression level of KRAS protein.

The methods of this invention can be applicable to any animal, including humans.

The mammal can be a human, the GST-π can be a human GST-π, and the p21 can be a human p21. In some embodiments, the malignant tumor overexpresses GST-π, and if the expression of GST-π is downregulated, then the level of p21 may be upregulated. The RNAi molecules can decrease expression of GST-π and p21 in the mammal. The administration can decrease expression of GST-π and p21 in the mammal by at least 5% for at least 5 days. The method can reduce one or more symptoms of the malignant tumor, or delays or terminates the progression of the malignant tumor, or reduce growth of malignant tumor cells in the subject. The tumor cells may comprise increased levels of expression of wild type KRAS protein as compared to that in a normal cell. The tumor cells may overexpress wild-type GST-π RNA or protein, and if expression of GST-π is suppressed, the level of p21 RNA or protein may be elevated.

In some embodiments, the tumor cells can comprise mutations in the KRAS protein at one or more of residues 12, 13 and 61. In certain embodiments, the tumor cells can comprise mutations in the KRAS protein and the tumor is a cancer selected from colon cancer, pancreatic cancer and lung cancer. The tumor can be a sarcoma selected from the group consisting of lung adenocarcinoma, mucinous adenoma, ductal carcinoma of the pancreas and colorectal carcinoma. The malignant tumor can be a sarcoma selected from the group of lung adenocarcinoma, mucinous adenoma, ductal carcinoma of the pancreas, colorectal carcinoma, breast cancer, and fibrosarcoma. The malignant tumor can be located in any anatomical region, which in some embodiments can be selected from the group of lung, liver, pancreas, colon, kidney, bone, skin, intestine, and any combination thereof.

In another aspect, this invention relates to the surprising discovery that malignant tumor size can be reduced in vivo by treatment with siRNA inhibitors of GST-π and p21. In addition, this invention provides the unexpectedly advantageous result that tumor cell apoptosis can be increased to a level of synthetic lethality to provide methods and compositions for preventing or treating malignant tumors.

This invention relates to methods and compositions incorporating nucleic acid based therapeutic compounds for use in delivery to various organs for preventing, treating, or ameliorating conditions and diseases of malignant tumor. In some embodiments, this invention provides compositions of RNA interference molecules (RNAi molecules) for gene silencing of various targets related to malignant tumors.

This invention can provide compositions for delivery of therapeutic molecules, as well as methods of use thereof. Various RNA-based and drug compositions of this invention can be used in methods for preventing or treating malignant tumors.

In some embodiments, malignant tumors containing a KRAS mutation or displaying aberrant KRAS expression levels can be reduced by treatment with siRNA agents that modulate expression of GST-π and p21 to a level that creates synthetic lethality for tumor cells.

This invention relates to methods and compositions for nucleic acid based therapeutic compounds against malignant tumors. In some embodiments, this invention provides RNAi molecules, structures and compositions that can silence expression of GST-π and p21. The structures and compositions of this disclosure can be used in preventing, treating or reducing the size of malignant tumors.

This invention provides compositions and methods that may be used for treating a neoplasia in a subject. In particular, this invention provides therapeutic compositions that can decrease the expression of a GST-π nucleic acid molecule or polypeptide, as well as a p21 nucleic acid molecule or polypeptide for treating a KRAS-associated neoplasia.

In some aspects, this invention includes an inhibitory nucleic acid molecule that corresponds to, or is complementary to at least a fragment of a GST-π nucleic acid molecule, and that decreases GST-π expression in a cell. In further aspects, this invention includes an inhibitory nucleic acid molecule that corresponds to, or is complementary to at least a fragment of a p21 nucleic acid molecule, and that decreases p21 expression in a cell.

In certain embodiments, this invention provides double-stranded nucleic acid molecules that are RNAi molecules such as siRNAs or shRNAs, as well as DNA-directed RNAs (ddRNA), Piwi-interacting RNAs (piRNA), and repeat associated siRNAs (rasiRNA) for suppressing GST-π and p21.

The methods of this invention can be applicable to any animal, including humans.

In some aspects, this invention includes one or more vectors encoding the inhibitory nucleic acid molecules described above. A vector can be a retroviral, adenoviral, adeno-associated viral, or lentiviral vector. In further embodiments, a vector can contain a promoter suitable for expression in a mammalian cell. Additional embodiments include cancer cells containing a KRAS mutation or displaying aberrant KRAS expression levels, which can also contain the vector, or an inhibitory nucleic acid molecule of any one of the above aspects. In further embodiments, the cells can be neoplastic cells in vivo.

In some embodiments, this invention includes methods for decreasing GST-π and p21 expression in a malignant tumor cell containing a KRAS mutation or displaying aberrant KRAS expression. Methods can include contacting the cell with an effective amount of the inhibitory nucleic acid molecules, where the inhibitory nucleic acid molecules inhibit expression of a GST-π polypeptide and a p21 polypeptide, thereby decreasing GST-π and p21 expression in the cell.

In additional embodiments, methods of this invention can decrease GST-π and p21 transcription or translation in malignant tumors.

In particular embodiments, this invention includes methods for decreasing GST-π and p21 expression in a malignant tumor cell, where the cell can be a human cell, a neoplastic cell, a cell in vivo, or a cell in vitro.

Embodiments of this invention can also provide methods for treating a subject having a neoplasm, where neoplasm cancer cells contain a KRAS mutation or display aberrant KRAS expression levels. Methods can involve administering to the subject an effective amount of two or more inhibitory nucleic acid molecules, where the inhibitory nucleic acid molecules reduce GST-π and p21 expression, thereby treating the neoplasm. In some embodiments, methods of this invention can decrease the size of a neoplasm, relative to the size of the neoplasm prior to treatment or without treatment.

In various embodiments, an inhibitory nucleic acid molecule can be delivered in a liposome, a polymer, a microsphere, a nanoparticle, a gene therapy vector, or a naked DNA vector.

In further aspects, this invention features methods for treating a subject, e.g. a human patient, having a neoplasm in which the neoplasm cancer cells contain a KRAS mutation or display aberrant KRAS expression levels. In certain embodiments, the methods can include administering to the subject an effective amount of inhibitory nucleic acid molecules, where the inhibitory nucleic acid molecules are antisense nucleic acid molecules, siRNAs, dsRNAs that are active for RNA interference, or a combination thereof, which inhibit expression of a GST-π polypeptide and a p21 polypeptide.

In particular embodiments, a cell of the neoplasm overexpresses GST-π, and if GST-π is suppressed, the level of p21 can be elevated.

In certain embodiments, the neoplasm can be a malignant tumor, or lung cancer, kidney cancer or pancreatic cancer.

Structures of Lipid Tails

A lipid-like compound of this invention may have one or more lipophilic tails that contain one or more alkyl or alkenyl groups. Examples of lipophilic tails include C(14:1(5))alkenyl, C(14:1(9))alkenyl, C(16:1(7))alkenyl, C(16:1(9))alkenyl, C(18:1(3))alkenyl, C(18:1(5))alkenyl, C(18:1(7))alkenyl, C(18:1(9))alkenyl, C(18:1(11))alkenyl, C(18:1(12))alkenyl, C(18:2(9,12))alkenyl, C(18:2(9,11))alkenyl, C(18:3(9,12,15))alkenyl, C(18:3(6,9,12))alkenyl, C(18:3(9,11,13))alkenyl, C(18:4(6,9,12,15))alkenyl, C(18:4(9,11,13,15))alkenyl, C(20:1(9))alkenyl, C(20:1(11))alkenyl, C(20:2(8,11))alkenyl, C(20:2(5,8))alkenyl, C(20:2(11,14))alkenyl, C(20:3(5,8,11))alkenyl, C(20:4(5,8,11,14))alkenyl, C(20:4(7,10,13,16))alkenyl, C(20:5(5,8,11,14,17))alkenyl, C(20:6(4,7,10,13,16,19))alkenyl, C(22:1(9))alkenyl, C(22:1(13))alkenyl, and C(24:1(9))alkenyl.

Chemical Definitions

The term "alkyl" as used herein refers to a hydrocarbyl radical of a saturated aliphatic group, which can be of any length. An alkyl group can be a branched or unbranched, substituted or unsubstituted aliphatic group containing from 1 to 22 carbon atoms. This definition also applies to the alkyl portion of other groups such as, for example, cycloalkyl, alkoxy, alkanoyl, and aralkyl, for example.

As used herein, a term such as "C(1-5)alkyl" includes C(1)alkyl, C(2)alkyl, C(3)alkyl, C(4)alkyl, and C(5)alkyl. Likewise, for example, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

As used herein, an alkyl group may be designated by a term such as Me (methyl), Et (ethyl), Pr (any propyl group), $^n$Pr (n-Pr, n-propyl), $^i$Pr (i-Pr, isopropyl), Bu (any butyl group), $^n$Bu (n-Bu, n-butyl), $^i$Bu (i-Bu, isobutyl), $^s$Bu (s-Bu, sec-butyl), and $^t$Bu (t-Bu, tert-butyl).

The term "alkenyl" as used herein refers to hydrocarbyl radical having at least one carbon-carbon double bond. An alkenyl group can be branched or unbranched, substituted or unsubstituted hydrocarbyl radical having 2 to 22 carbon atoms and at least one carbon-carbon double bond.

The term "substituted" as used herein refers to an atom having one or more substitutions or substituents which can be the same or different and may include a hydrogen substituent. Thus, the terms alkyl, cycloalkyl, alkenyl, alkoxy, alkanoyl, and aryl, for example, refer to groups which can include substituted variations. Substituted variations include linear, branched, and cyclic variations, and groups having a substituent or substituents replacing one or more hydrogens attached to any carbon atom of the group.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, March's Advanced Organic Chemistry, 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Example Protocol for In Vitro Knockdown

One day before the transfection, cells were plated in a 96-well plate at 2×10³ cells per well with 100 µl of DMEM (HyClone Cat. # SH30243.01) containing 10% FBS and culture in a 37° C. incubator containing a humidified atmosphere of 5% CO2 in air. Before transfection, medium was changed to 90 µl of Opti-MEM I Reduced Serum Medium (Life Technologies Cat. #31985-070) containing 2% FBS. Then, 0.2 µl of Lipofectamine RNAiMax (Life Technologies Cat. #13778-100) was mixed with 4.8 µl of Opti-MEM I for 5 minutes at room temperature. Next, 1 µl of siRNA was mixed with 4 µl of Opti-MEM I and combined with the LF2000 solution, and mixed gently, without vortex. After 5 minutes at room temperature, the mixture was incubated for an additional 10 minutes at room temperature to allow the RNA-RNAiMax complexes to form. Further, the 10 µl of RNA-RNAiMax complexes was added to a well, and the plate was shaken gently by hand. The cells were incubated in a 37° C. incubator containing a humidified atmosphere of 5% CO2 in air for 2 hours. The medium was changed to fresh Opti-MEM I Reduced Serum Medium containing 2% FBS. 24 hours after transfection, the cells were washed with ice-cold PBS once. The cells were lysed with 50 µl of Cell-to-Ct Lysis Buffer (Life Technologies Cat. #4391851 C) for 5-30 minutes at room temperature. 5 µl of Stop Solution was added, and it was incubated for 2 minutes at room temperature. The mRNA level was measured by RT-qPCR with TAQMAN immediately. Samples could be frozen at −80° C. and assayed at a later time.

Example Protocol for Serum Stability 0.2 mg/ml siRNA was incubated with 10% human serum at 37° C. At certain time points (0, 5, 15 and 30 min), 200 µl of sample was aliquoted and extracted with 200 µl extraction solvent (Chloroform:phenol:Isoamyl alcohol=24:25:1). The sample was vortexed and centrifuged at 13,000 rpm for 10 min at RT, then the top layer solution was transferred and filtered it with 0.45 µm filter. The filtrate was transferred into a 300 µl HPLC injection vial. For LCMS, the Mobile phase was MPA: 100 mM HFIP+7 mM TEA in H2O, MPB: 50% Methanol+50% Acetonitrile. The Column: Waters Acquity OST 2.1×50 mm, 1.7 µm.

EXAMPLES

Example 1

The formulation of GST-π and p21 siRNAs of this invention exhibited profound reduction of cancer xenograft tumors in vivo. The GST-π and p21 siRNAs provided gene knockdown potency in vivo when administered in a liposomal formulation to the cancer xenograft tumors.

FIG. 1 shows tumor inhibition efficacy for a liposomal formulation of GST-π (SEQ ID NOs:61 and 126) and p21 (SEQ ID NOs:341 and 355, N=U) siRNAs. A cancer xenograft model was utilized with a relatively low dose at 1.15 mg/kg for the GST-π siRNA and 0.74 mg/kg for the p21 siRNA.

The formulation of GST-π and p21 siRNAs showed significant and unexpectedly advantageous tumor inhibition efficacy within a few days after administration. After 30 days, the GST-π and p21 siRNAs showed markedly advantageous tumor inhibition efficacy, with tumor volume reduced by greater than 2-fold as compared to control.

The GST-π siRNA was administered in four injections (day 1, 8, 15 and 22) of a liposomal formulation having the composition (Ionizable lipid: Cholesterol: DOPE:DOPC:DPPE-PEG-2K) (25:30:20:20:5).

For the cancer xenograft model, an A549 cell line was obtained from ATCC. The cells were maintained in culture medium supplemented with 10% Fetal Bovine Serum and 100 U/ml penicillin and 100 µg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of $5×10^7$/ml in media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 7-8 mice per group.

For tumor model preparation, each mouse was inoculated subcutaneously in the right flank with 0.1 ml an inoculum of $2.5×10^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width/2. Once the established tumors reached approximately 120-175 mm³, average tumor volume was about 150 mm³, the mice were assigned into the various vehicle control and treatment groups such that the mean tumor volumes in the treated groups were within 10% of the mean tumor volume in the vehicle control group, ideally, the CV % of tumor volume was less than 25%. On the same day, test articles and control vehicle were administered according to the dosing regimen. Tumor volumes were monitored three times for week 1, twice for the rest of weeks, including the day of study termination.

For dosage administration, on the dosing day, the test articles were taken out from −80° C. freezer and thawed on ice. Before applied to syringes, the bottle containing formulation was reverted by hands for a few times. All test articles were dosed by IV, at 10 ml/kg.

For body weight, mice were weighed to the nearest 0.1 g. Body weights were monitored and recorded daily within 7 days post dosing for first dose. Body weights were monitored and recorded twice for weeks, for the rest of weeks, including the day of study termination.

For tumors collection, on 28 days post first dosing, tumor volume was measured, and tumor was dissected for weight measurement, and stored for PD biomarker study. Tumor weight was recorded.

Example 2

The formulation of GST-π and p21 siRNAs of this invention exhibited profound reduction of cancer xenograft tumors in vivo. The GST-π and p21 siRNAs provided gene knockdown potency in vivo when administered in a liposomal formulation to the cancer xenograft tumors.

Figure 2:
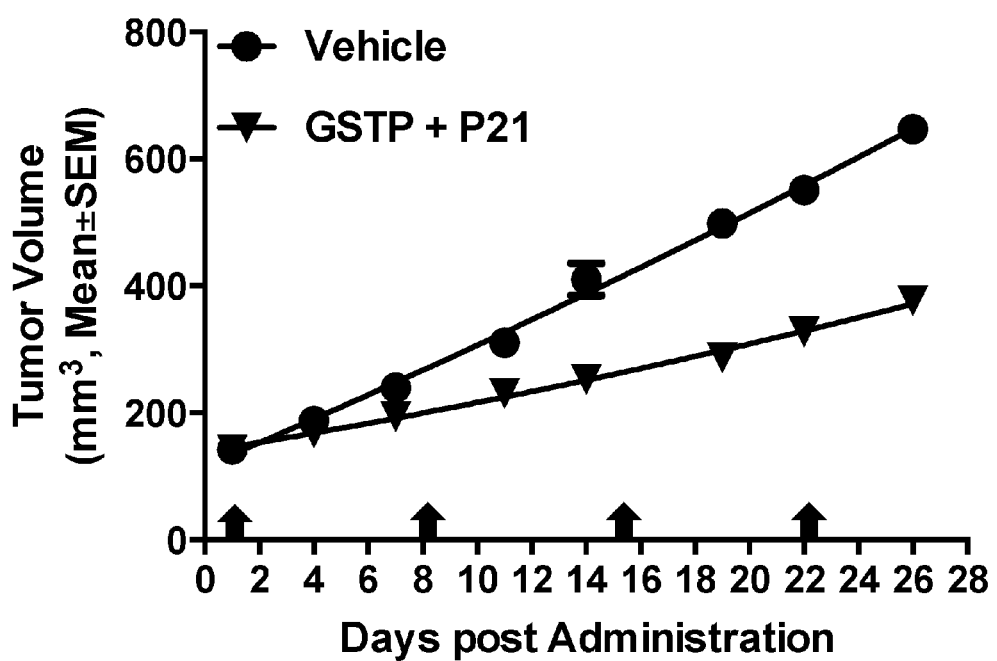
FIG. 2 shows profound reduction of cancer xenograft tumors in vivo using a formulation of GST-π and p21 siRNAs of this invention. The GST-π and p21 siRNAs provided gene knockdown potency in vivo when administered in a liposomal formulation to the cancer xenograft tumors. A cancer xenograft model was utilized with a relatively low dose at 0.75 mg/kg for each siRNA. The formulation of GST-π and p21 siRNAs showed significant tumor inhibition efficacy within a few days after administration. After 30 days, the GST-π and p21 siRNAs showed markedly advantageous tumor inhibition efficacy, with tumor volume reduced by 1.7-fold as compared to control.

FIG. 2 shows tumor inhibition efficacy for a liposomal formulation of GST-π (SEQ ID NOs:156 and 182) and p21 (SEQ ID NOs:341 and 355, N=U) siRNAs. A cancer xenograft model was utilized with a relatively low dose at 0.75 mg/kg for each siRNA.

The formulation of GST-π and p21 siRNAs showed significant and unexpectedly advantageous tumor inhibition efficacy within a few days after administration. After 30 days, the GST-π and p21 siRNAs showed markedly advantageous tumor inhibition efficacy, with tumor volume reduced by 1.7-fold as compared to control.

Example 3

The formulations of GST-π and p21 siRNAs of this invention demonstrated increased cancer cell death by apoptosis of cancer cells in vitro. Apoptosis of cancer cells in vitro was monitored by observing upregulation of PUMA, a biomarker for apoptosis, which is associated with loss in cell viability.

The formulations of GST-π and p21 siRNAs provided unexpectedly increased apoptosis of cancer cells.

Figure 3:
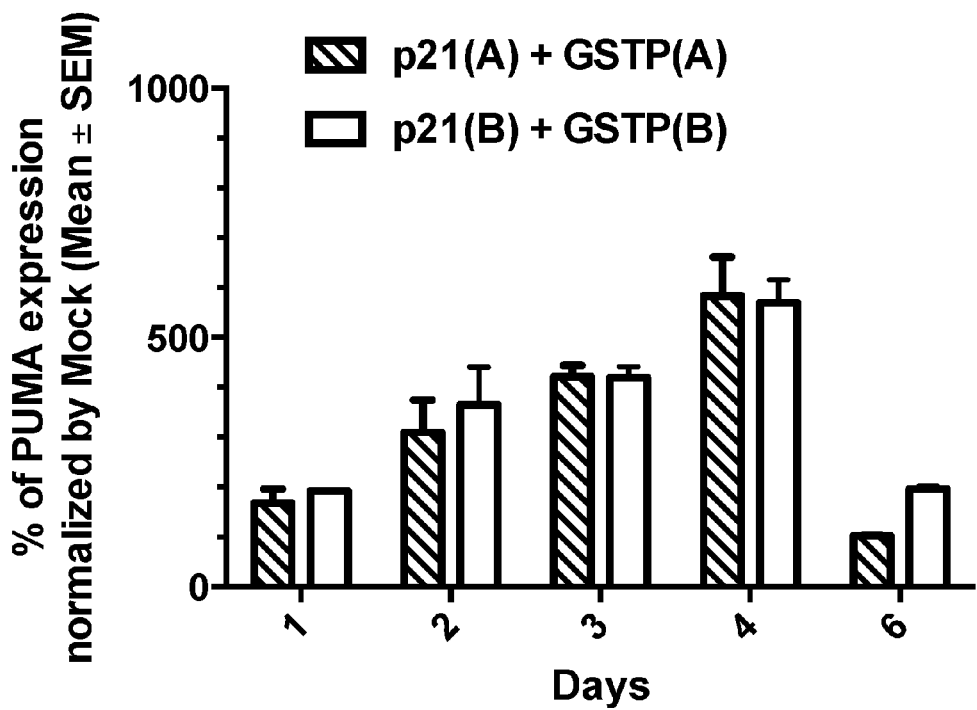
FIG. 3 shows that the formulations of GST-π and p21 siRNAs of this invention demonstrated increased cancer cell death by apoptosis of cancer cells in vitro. Apoptosis of cancer cells in vitro was monitored by observing upregulation of PUMA, a biomarker for apoptosis, which is associated with loss in cell viability.

As shown in FIG. 3, the level of expression of PUMA for a formulation of GST-π and p21 siRNAs (FIG. 3, p21(A)+GSTP(A), P21 SEQ ID NOs:341 and 355, N=U, GSTP SEQ ID NOs:156 and 182) was greatly increased from about 2-4 days after transfection of the GST-π and p21 siRNAs.

These data show that the formulations of GST-π and p21 siRNAs of this invention provided unexpectedly increased apoptosis of cancer cells.

The protocol for the PUMA biomarker was as follows. One day before transfection, cells were plated in a 96-well plate at $2 \times 10^3$ cells per well with 100 μl of DMEM (Hy-Clone Cat. # SH30243.01) containing 10% FBS and cultured in a 37° C. incubator containing a humidified atmosphere of 5% CO2 in air. Next day, before transfection the medium was replaced with 90 μl of Opti-MEM I Reduced Serum Medium (Life Technologies Cat. #31985-070) containing 2% FBS. Then, 0.2 μl of Lipofectamine RNAiMAX (Life Technologies Cat. #13778-100) were mixed with 4.8 μl of Opti-MEM I for 5 minutes at room temperature. 1 μl of the siRNAs (stock conc. 1 μM) was mixed with 4 μl of Opti-MEM I and combined with the RNAiMAX solution and then mixed gently. The mixture was incubated for 10 minutes at room temperature to allow the RNA-RNAiMAX complexes to form. 10 μl of RNA-RNAiMAX complexes were added per well, to final concentration of the siRNA 10 nM. The cells were incubated for 2 hours and medium changed to fresh Opti-MEM I Reduced Serum Medium containing 2% FBS. For 1, 2, 3, 4, and 6 days post transfection, the cells were washed with ice-cold PBS once and then lysed with 50 μl of Cell-to-Ct Lysis Buffer (Life Technologies Cat. #4391851 C) for 5-30 minutes at room temperature. 5 μl of Stop Solution was added and incubated for 2 minutes at room temperature. PUMA (BBC3, Cat# Hs00248075, Life Technologies) mRNA levels were measured by qPCR with TAQMAN.

Example 4

A double knockdown in vitro study of siRNAs targeted to GST-π and p21 showed that the combination was highly active for suppressing the mRNA levels of both proteins. As shown in Table 11, the knockdown level for each of GST-π and p21 was high for concentrations of 2, 10 and 50 nM.

TABLE 11

Double Knockdown in A549

| nM | P21 KD (%) SEQ ID NOs.: P21: 341/355 (N = U) GST-π: 156/182 | P21 KD (%) SEQ ID NOs.: P21: 312/340 (overhangs mUmU) GST-π: 156/182 | GST-π KD (%) SEQ ID NOs.: P21: 341/355 (N = U) GST-π: 156/182 | GST-π KD (%) SEQ ID NOs.: P21: 312/340 (overhangs mUmU) GST-π: 156/182 |
|---|---|---|---|---|
| 2 | 76.8 | 85.0 | 73.6 | 89.6 |
| 10 | 84.7 | 91.6 | 79.4 | 93.3 |
| 50 | 82.1 | 94.5 | 81.3 | 93.8 |

Protocol: Transfect with P21 siRNA at 2, 10, and 50 nM. After 1, 2, 3, or 4 days transfect with GST-π siRNA at 10 nM. 1 day later analyze by RT-PCR for P21 mRNA and GST-π mRNA levels.

Example 5

Orthotopic A549 Lung Cancer Mouse Model

The GST-π siRNAs of this invention can exhibit profound reduction of orthotopic lung cancer tumors in vivo. In this example, a GST-π siRNA provided gene knockdown potency in vivo when administered in a liposomal formulation to the orthotopic lung cancer tumors in athymic nude mice.

In general, an orthotopic tumor model can exhibit direct clinical relevance for drug efficacy and potency, as well as improved predictive ability. In the orthotopic tumor model, tumor cells are implanted directly into the same kind of organ from which the cells originated.

The anti-tumor efficacy of the siRNA formulation against human lung cancer A549 was evaluated by comparing the final primary tumor weights measured at necropsy for the treatment group and the vehicle control group.

Figure 4:
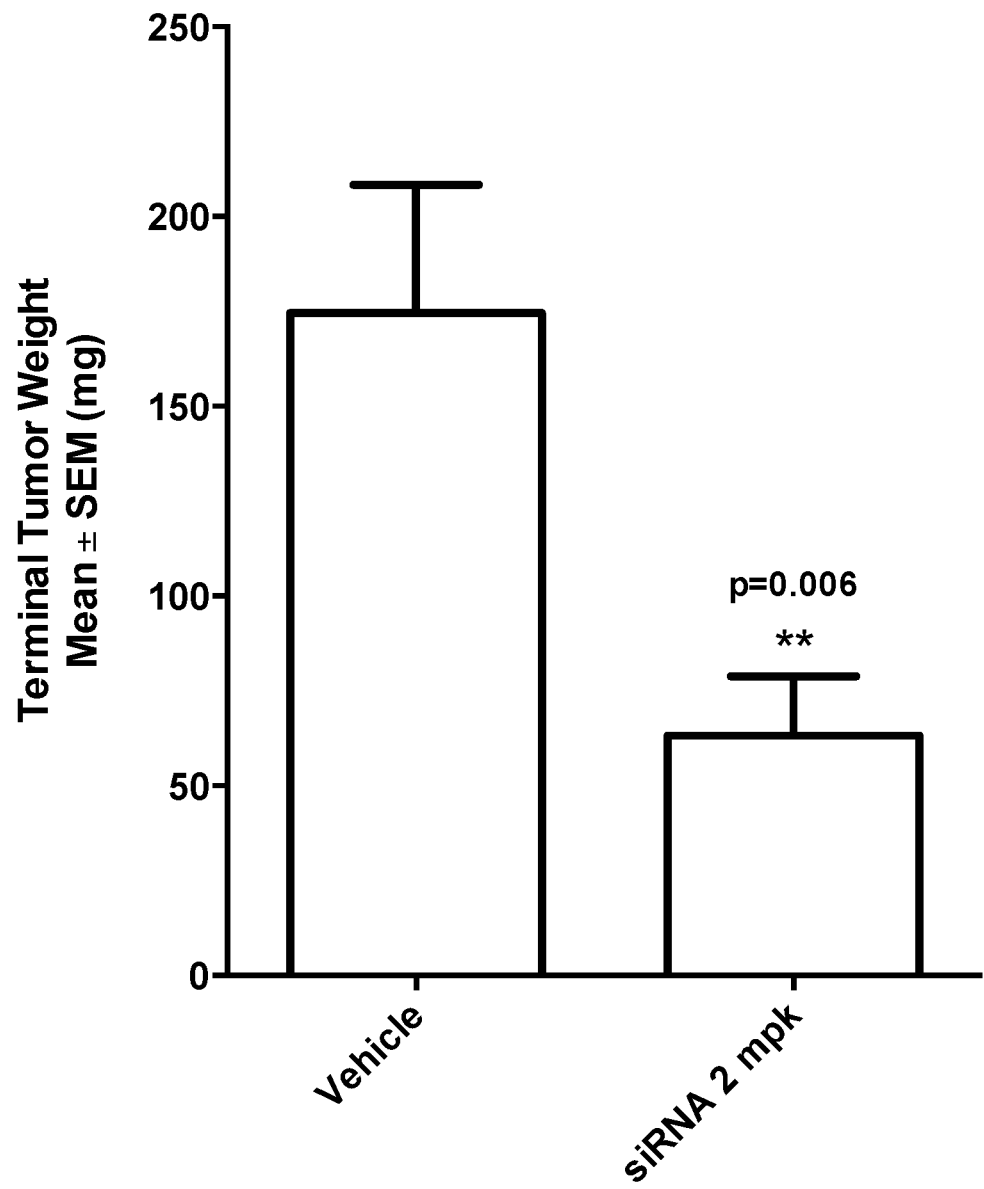
FIG. 4 shows the profound reduction of orthotopic lung cancer tumors in vivo by a siRNA of this invention targeted to GST-π. The GST-π siRNA was administered in a liposomal formulation at a dose of 2 mg/kg to athymic nude mice presenting A549 orthotopic lung cancer tumors. Final primary tumor weights were measured at necropsy for the treatment group and a vehicle control group. The GST-π siRNA showed significant efficacy for inhibition of lung cancer tumors in this six-week study.

FIG. 4 shows orthotopic lung cancer tumor inhibition in vivo for a GST-π siRNA based on structure BU2 (SEQ ID NOs:61 and 126). An orthotopic A549 lung cancer mouse model was utilized with a relatively low dose at 2 mg/kg of the siRNA targeted to GST-π.

The GST-π siRNA showed significant and unexpectedly advantageous lung tumor inhibition efficacy in this six-week study. As shown in FIG. 4, after 43 days, the GST-π siRNA showed markedly advantageous tumor inhibition efficacy, with final tumor average weights significantly reduced by 2.8-fold as compared to control.

For this study, male NCr nu/nu mice, 5-6 weeks old, were used. The experimental animals were maintained in a HEPA filtered environment during the experimental period. The siRNA formulations were stored at 4° C. before use, and warmed to room temperature 10 minutes prior to injection in mouse.

For this A549 human lung cancer orthotopic model, on the day of surgical orthotopic implantation (SOI), the stock tumors were harvested from the subcutaneous site of animals bearing A549 tumor xenograft and placed in RPMI-1640 medium. Necrotic tissues were removed and viable tissues were cut into 1.5-2 mm³ pieces. The animals were anesthetized with isoflurane inhalation and the surgical area was sterilized with iodine and alcohol. A transverse incision approximately 1.5 cm long was made in the left chest wall of the mouse using a pair of surgical scissors. An intercostal incision was made between the third and the fourth rib and the left lung was exposed. One A549 tumor fragment was transplanted to the surface of the lung with an 8-0 surgical suture (nylon). The chest wall was closed with a 6-0 surgical suture (silk). The lung was re-inflated by intrathoracic puncture using a 3 cc syringe with a 25 G×1½ needle to draw out the remaining air in the chest cavity. The chest wall was closed with a 6-0 surgical silk suture. All procedures of the operation described above were performed with a 7× magnification microscope under HEPA filtered laminar flow hoods.

Three days after tumor implantation, the model tumor-bearing mice were randomly divided into groups of ten mice per group. For the group of interest, treatment of the ten mice was initiated three days after tumor implantation.

For the group of interest, the formulation was (Ionizable lipid: cholesterol:DOPE:DOPC:DPPE-PEG-2K:DSPE-PEG-2K), a liposomal composition. The liposomes encapsulated the GST-π siRNA.

For the study endpoint, the experimental mice were sacrificed forty-two days after treatment initiation. Primary tumors were excised and weighed on an electronic balance for subsequent analysis.

For an estimation of compound toxicity, the mean body weight of the mice in the treated and control groups was maintained within the normal range during the entire experimental period. Other symptoms of toxicity were not observed in the mice.

Example 6

The GST-π siRNAs of this invention exhibited profound reduction of cancer xenograft tumors in vivo. The GST-π siRNAs provided gene knockdown potency in vivo when administered in a liposomal formulation to the cancer xenograft tumors.

Figure 5:
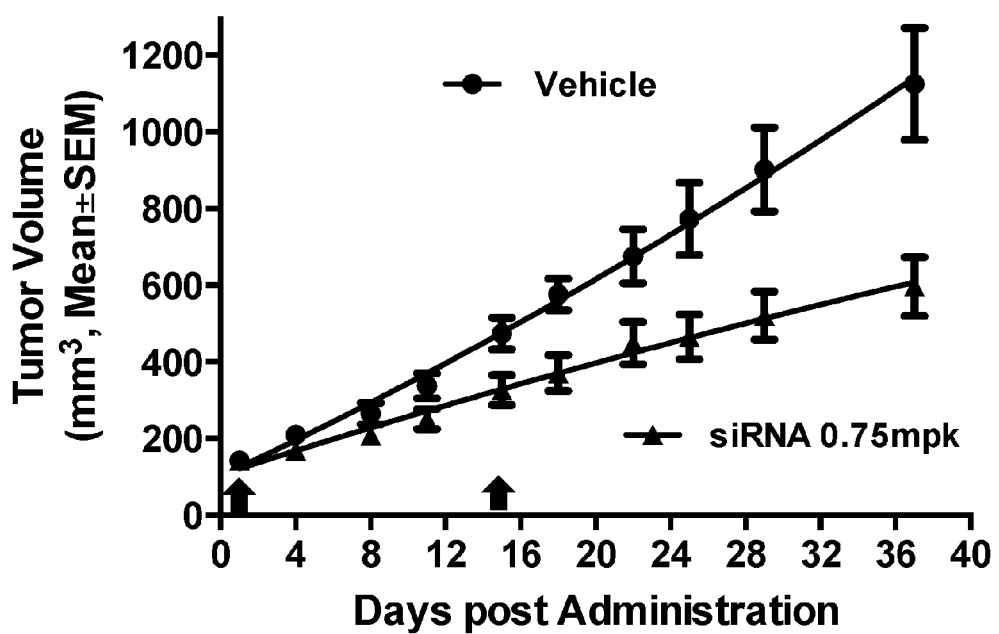
FIG. 5 shows tumor inhibition efficacy in vivo for a GST-π siRNA. A cancer xenograft model using A549 cells was utilized with a relatively low dose of siRNA at 0.75 mg/kg. The GST-π siRNA showed advantageous tumor inhibition within a few days. After 36 days, the GST-π siRNA showed markedly advantageous tumor inhibition, with final tumor average volumes significantly reduced by about 2-fold, as compared to control.

FIG. 5 shows tumor inhibition efficacy for a GST-π siRNA (SEQ ID Nos:156 and 182). A cancer xenograft model was utilized with a relatively low dose at 0.75 mg/kg of siRNA targeted to GST-π.

The GST-π siRNA showed significant and unexpectedly advantageous tumor inhibition efficacy within a few days after administration. After 36 days, the GST-π siRNA showed markedly advantageous tumor inhibition efficacy, with tumor volume reduced by 2-fold as compared to control.

As shown in FIG. 5, the GST-π siRNA demonstrated significant and unexpectedly advantageous tumor inhibition efficacy at the endpoint day. In particular, tumor weight was reduced by more than 2-fold.

The GST-π siRNA was administered in two injections (day 1 and 15) of a liposomal formulation having the composition (Ionizable lipid:Cholesterol:DOPE:DOPC: DPPE-PEG-2K) (25:30:20:20:5).

For the cancer xenograft model, an A549 cell line was obtained from ATCC. The cells were maintained in culture medium supplemented with 10% Fetal Bovine Serum and 100 U/ml penicillin and 100 µg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of $5 \times 10^7$/ml in media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 7-8 mice per group.

For tumor model preparation, each mouse was inoculated subcutaneously in the right flank with 0.1 ml an inoculum of $2.5 \times 10^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Once the established tumors reached approximately 120-175 mm$^3$, average tumor volume was about 150 mm$^3$, the mice were assigned into the various vehicle control and treatment groups such that the mean tumor volumes in the treated groups were within 10% of the mean tumor volume in the vehicle control group, ideally, the CV % of tumor volume was less than 25%. On the same day, test articles and control vehicle were administered according to the dosing regimen. Tumor volumes were monitored three times for week 1, twice for the rest of weeks, including the day of study termination.

For dosage administration, on the dosing day, the test articles were taken out from −80° C. freezer and thawed on ice. Before applied to syringes, the bottle containing formulation was reverted by hands for a few times. All test articles were dosed at 0.75 mg/kg by IV, q2w×2, at 10 ml/kg.

For body weight, mice were weighed to the nearest 0.1 g. Body weights were monitored and recorded daily within 7 days post dosing for first dose. Body weights were monitored and recorded twice for weeks, for the rest of weeks, including the day of study termination.

For tumors collection, on 28 days post first dosing, tumor volume was measured, and tumor was dissected for weight measurement, and stored for PD biomarker study. Tumor weight was recorded.

Example 7

The GST-π siRNAs of this invention demonstrated increased cancer cell death by apoptosis of cancer cells in vitro. The GST-π siRNAs provided GST-π knockdown, which resulted in upregulation of PUMA, a biomarker for apoptosis and associated with loss in cell viability.

GST-π siRNA SEQ ID NOs:156 and 182, which contained a combination of deoxynucleotides in the seed region, a 2'-F substituted deoxynucleotide, and 2'-OMe substituted ribonucleotides, provided unexpectedly increased apoptosis of cancer cells.

Figure 6:
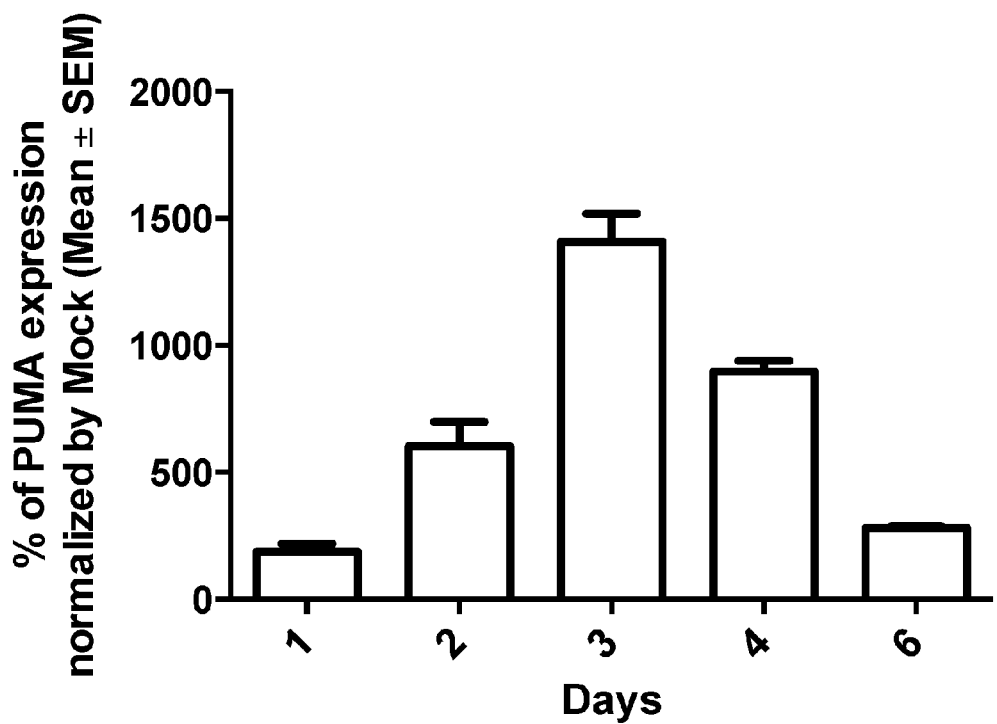
FIG. 6 shows that a GST-π siRNA of this invention greatly increased cancer cell death by apoptosis in vitro. The GST-π siRNA caused upregulation of PUMA, a biomarker for apoptosis, which is associated with loss in cell viability.

The level of expression of PUMA for GST-π siRNA SEQ ID NOs:156 and 182 was measured as shown in FIG. 6. In FIG. 6, the expression of PUMA was greatly increased from 2-4 days after transfection of the GST-π siRNA.

These data show that the structure of GST-π siRNAs containing a combination of deoxynucleotides in the seed region, a 2'-F substituted deoxynucleotide, and 2'-OMe substituted ribonucleotides provided unexpectedly increased apoptosis of cancer cells.

The protocol for the PUMA biomarker was as follows. One day before transfection, cells were plated in a 96-well plate at $2 \times 10^3$ cells per well with 100 µl of DMEM (Hy-Clone Cat. # SH30243.01) containing 10% FBS and cultured in a 37° C. incubator containing a humidified atmosphere of 5% CO2 in air. Next day, before transfection the medium was replaced with 90 µl of Opti-MEM I Reduced Serum Medium (Life Technologies Cat. #31985-070) containing 2% FBS. Then, 0.2 µl of Lipofectamine RNAiMAX (Life Technologies Cat. #13778-100) were mixed with 4.8 µl of Opti-MEM I for 5 minutes at room temperature. 1 µl of the GST-π siRNA (stock conc. 1 µM) was mixed with 4 µl of Opti-MEM I and combined with the RNAiMAX solution and then mixed gently. The mixture was incubated for 10 minutes at room temperature to allow the RNA-RNAiMAX complexes to form. 10 µl of RNA-RNAiMAX complexes were added per well, to final concentration of the siRNA 10 nM. The cells were incubated for 2 hours and medium changed to fresh Opti-MEM I Reduced Serum Medium containing 2% FBS. For 1, 2, 3, 4, and 6 days post transfection, the cells were washed with ice-cold PBS once and then lysed with 50 µl of Cell-to-Ct Lysis Buffer (Life Technologies Cat. #4391851 C) for 5-30 minutes at room temperature. 5 µl of Stop Solution was added and incubated for 2 minutes at room temperature. PUMA (BBC3, Cat#

Hs00248075, Life Technologies) mRNA levels were measured by qPCR with TAQMAN.

Example 8

The GST-π siRNAs of this invention can exhibit profound reduction of cancer xenograft tumors in vivo. The GST-π siRNAs can provide gene knockdown potency in vivo when administered in a liposomal formulation to the cancer xenograft tumors.

Figure 7:
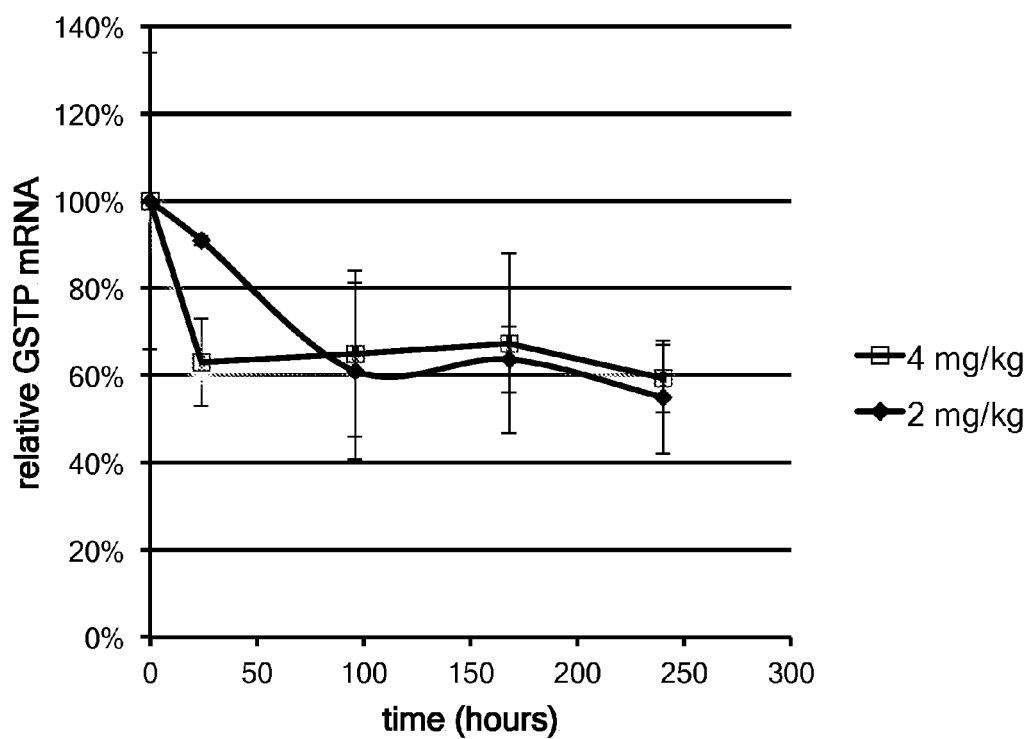
FIG. 7.

FIG. 7 shows tumor inhibition efficacy for a GST-π siRNA (SEQ ID NOs:61 and 126). Dose dependent knockdown of GST-π mRNA was observed in vivo with the siRNA targeted to GST-π. A cancer xenograft model was utilized with a siRNA targeted to GST-π.

The GST-π siRNA showed significant and unexpectedly advantageous tumor inhibition efficacy within a few days after administration. As shown in FIG. 7, treatment with a GST-π siRNA resulted in significant reduction of GST-π mRNA expression 4 days after injection in a lipid formulation. At the higher dose of 4 mg/kg, significant reduction of about 40% was detected 24 hours after injection.

The p21 siRNA was administered in a single injection of 10 mL/kg of a liposomal formulation having the composition (Ionizable lipid:Cholesterol:DOPE:DOPC:DPPE-PEG-2K) (25:30:20:20:5).

For the cancer xenograft model, an A549 cell line was obtained from ATCC. The cells were maintained in RPMI-1640 supplemented with 10% Fetal Bovine Serum and 100 U/ml penicillin and 100 μg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of $4 \times 10^7$/ml in RPMI media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 3 mice per group.

For tumor model preparation, each mouse was inoculated subcutaneously in the right flank with 0.1 ml an inoculum of $2 \times 10^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Tumor volumes were monitored twice a week. Once the established tumors reached approximately 350-600 mm$^3$, the mice were assigned into groups with varied time points. On the same day, test articles were administered according to the dosing regimen.

For dosage administration, on the day when the established tumors reached approximately 350-600 mm$^3$, the test articles were taken out from 4° C. fridge. Before being applied to syringes, the bottle containing formulation was reverted by hand for a few times to make a homogeneous solution.

For body weight, mice were weighed to the nearest 0.1 g. Body weights were monitored and recorded twice for weeks, for the rest of weeks, including the day of study termination.

For tumors collection, animals were sacrificed by overdosed $CO_2$ and tumors were dissected at 0, 24, 48, 72, 96 (optional), and 168 hours following the dosing. Tumors were first wet weighted, and then separated into three parts for KD, distribution and biomarker analysis. The samples were snap frozen in liquid nitrogen and stored at −80° C. until ready to be processed.

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A composition comprising RNAi molecules targeted to a human GST-π, RNAi molecules targeted to a human p21, and a pharmaceutically acceptable carrier, wherein each of the RNAi molecules targeted to GST-π has an antisense strand SEQ ID NOs:131 and a sense strand SEQ ID NOs:157.

2. The composition of claim 1, wherein each of the RNAi molecules targeted to p21 has an antisense strand SEQ ID NOs:341 and a sense strand SEQ ID NOs:355.

3. The composition of claim 1, wherein each of the RNAi molecules targeted to GST-π has an antisense strand SEQ ID NOs:156 and a sense strand SEQ ID NOs:182.

4. The composition of claim 2, wherein each of the RNAi molecules targeted to p21 has an antisense strand SEQ ID NOs:343 and a sense strand SEQ ID NOs:357.

5. The composition of claim 1, wherein one or more of the nucleotides in the antisense strand or sense strand of the RNAi molecules is modified or chemically-modified.

6. The composition of claim 5, wherein the modified or chemically-modified nucleotides are 2'-deoxy nucleotides, 2'-O-alkyl substituted nucleotides, 2'-deoxy-2'-fluoro substituted nucleotides, phosphorothioate nucleotides, locked nucleotides, or any combination thereof.

7. The composition of claim 1, wherein each of the RNAi molecules contains a 2'-deoxynucleotide in one or more of positions 2 to 8 from the 5' end of the antisense strand.

8. The composition of claim 1, wherein the antisense strand of each of the RNAi molecules has deoxynucleotides in a plurality of positions, the plurality of positions being one of the following:
   each of positions 4, 6 and 8, from the 5' end of the antisense strand;
   each of positions 3, 5 and 7, from the 5' end of the antisense strand;
   each of positions 1, 3, 5 and 7, from the 5' end of the antisense strand;
   each of positions 3-8, from the 5' end of the antisense strand; or
   each of positions 5-8, from the 5' end of the antisense strand.

9. The composition of claim 1, wherein the composition inhibits expression of GST-π mRNA with an IC50 of less than 50 pM, and inhibits expression of p21 mRNA with an IC50 of less than 50 pM.

10. The composition of claim 1, wherein a single administration of the composition inhibits expression of GST-π mRNA levels in vivo by at least 25%.

11. The composition of claim 1, wherein the carrier comprises liposome nanoparticles that encapsulate the RNAi molecules.

12. The composition of claim 1, wherein the carrier comprises liposome nanoparticles that encapsulate the RNAi molecules and retain at least 80% of the encapsulated RNAi molecules after 1 hour exposure to human serum.

13. The composition of claim 1, wherein the carrier comprises liposome nanoparticles having a size of 10 to 1000 nm, or 10 to 150 nm.

14. The composition of claim 1, wherein the composition is active for treating malignant tumor.

15. The composition of claim 14, wherein the malignant tumor is located in the lung, colon, kidney, pancreas, liver, bone, skin, or intestine.

16. The composition of claim 1, wherein the carrier comprises liposome nanoparticles comprising an ionizable lipid, a structural lipid, one or more stabilizer lipids, and a lipid for reducing immunogenicity of the nanoparticles.

17. The composition of claim 16, wherein the ionizable lipid is selected from the group of ((2-((3S,4R)-3,4-dihydroxypyrrolidin-1-yl)acetyl)azanediyl)bis(ethane-2,1-diyl) (9Z,9'Z,12Z,12'Z)-bis(octadeca-9,12-dienoate), ((2-(3-(hydroxymethyl)azetidin-1-yl)acetyl)azanediyl)bis(ethane-2,1-diyl) ditetradecanoate, ((2-(4-(2-hydroxyethyl)piperazin-1-yl)acetyl)azanediyl)bis(ethane-2,1-diyl) (9Z,9'Z,12Z,12'Z)-bis(octadeca-9,12-dienoate), ((2-(4-(2-hydroxyethyl)piperazin-1-yl)acetyl)azanediyl)bis(ethane-2,1-diyl) (9Z,9'Z,12Z,12'Z)-bis(octadeca-9,12-dienoate), 2-((1-(((9Z,12Z)-heptadeca-9,12-dien-1-yl)oxy)-5-(((9Z,12Z)-octadeca-9,12-dien-1-yl)oxy)-1,5-dioxopentan-3-yl)amino)-N,N,N-trimethyl-2-oxoethan-1-aminium, 2-((9Z,12Z)-N-(3-(dimethylamino)propyl)octadeca-9,12-dienamido)ethyl (9Z,12Z)-octadeca-9,12-dienoate, N,N,N-trimethyl-3-((9Z,12Z)-N-(2-(((9Z,12Z)-octadeca-9,12-dienoyl)oxy)ethyl)octadeca-9,12-dienamido)propan-1-aminium, and N,N,N-trimethyl-2-(((S)-3-(((9Z,12Z)-octadeca-9,12-dien-1-yl)oxy)-2-((9Z,12Z)-octadeca-9,12-dienamido)-3-oxopropyl)amino)-2-oxoethan-1-aminium.

18. A method for preventing, treating or ameliorating one or more symptoms of a malignant tumor in a subject in need, the method comprising administering to the subject an effective amount of a composition of claim 1.

19. The method of claim 18, wherein the malignant tumor is associated with KRAS mutation, the method further comprising identifying a tumor cell in the subject, the tumor cell comprising at least one of: (i) a mutation of the KRAS gene, and (ii) an aberrant expression level of KRAS protein.

20. The method of claim 18, wherein the malignant tumor overexpresses GST-π.

21. The method of claim 18, wherein the RNAi molecules decrease expression of GST-π and p21 in the subject.

22. The method of claim 18, wherein the administration decreases expression of GST-π and p21 in the subject by at least 5% for at least 5 days.

23. The method of claim 18, wherein the administration decreases the volume of the malignant tumor in the subject by at least 5%, or at least 10%, or at least 20%, or at least 30%, or at least 40%, or at least 50%.

24. The method of claim 18, wherein the method reduces one or more symptoms of the malignant tumor, or delays or terminates the progression of the malignant tumor.

25. The method of claim 18, wherein the administration reduces growth of malignant tumor cells in the subject.

26. The method of claim 18, wherein the administration reduces growth for at least 2%, or at least 5%, or at least 10%, or at least 15%, or at least 20% of the malignant tumor cells in the subject.

27. The method of claim 18, wherein the malignant tumor is colon cancer, pancreatic cancer, kidney cancer, lung cancer, breast cancer, or fibrosarcoma.

28. The method of claim 18, wherein the malignant tumor is lung adenocarcinoma, mucinous adenoma, ductal carcinoma of the pancreas, or colorectal carcinoma.

29. The method of claim 18, wherein the administration is performed from 1 to 12 times per day.

30. The method of claim 18, wherein the administration is performed for a duration of 1, 2, 3, 4, 5, 6 or 7 days.

31. The method of claim 18, wherein the administration is performed for a duration of 1, 2, 3, 4, 5, 6, 8, 10 or 12 weeks.

32. The method of claim 18, wherein the administration is a dose of from 0.01 to 2 mg/kg of the RNAi molecules at least once per day for a period up to twelve weeks.

33. The method of claim 18, wherein the administration provides a mean AUC(0-last) of from 1 to 1000 ug*min/mL and a mean $C_{max}$ of from 0.1 to 50 ug/mL for the GST-π RNAi molecule.

34. The method of claim 18, wherein the administration provides a mean AUC(0-last) of from 1 to 1000 ug*min/mL and a mean $C_{max}$ of from 0.1 to 50 ug/mL for the p21 RNAi molecule.

35. The method of claim 18, wherein the administration is intravenous injection, intradermal injection, subcutaneous injection, intramuscular injection, intraperitoneal injection, oral, topical, infusion, or inhalation.

* * * * *

SEQUENCE LISTING

<160> NUMBER OF SEQ ID NOS: 368

<210> SEQ ID NO 1
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ucccagaacc agggaggcat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
cuuuugagac ccugcuguct t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
cugucccaga accagggagt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ugucccagaa ccagggaggt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
aagccuuuug agacccugct t                                              21

<210> SEQ ID NO 6
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
uugagacccu gcugucccat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
uuuugagacc cugcugucct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gagacccugc ugucccagat t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
gcuggaagga ggagguggut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuggaaggag gagguggugt t                                              21
```

-continued

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ucagggccag agcuggaagt t                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
ugagacccug cugucccagt t                                             21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agggccagag cuggaaggat t                                             21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
agcuggaagg aggagguggt t                                             21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
agacccugcu gucccagaat t                                             21
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gagcuggaag gaggaggugt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ugcuguccca gaaccagggt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
cccagaacca gggaggcaat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ccagaaccag ggaggcaagt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
uuugagaccc ugcuguccct t                                              21

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
gacccugcug ucccagaact t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
gaucagggcc agagcuggat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
agccuuuuga gacccugcut t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
gccuuuugag acccugcugt t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
```
ccuuuugaga cccugcugut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cgccuuuuga gacccugcat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ccuacaccgu ggucuauuut t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
ugugggagac cagaucucct t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
gcgggaggca gaguuugcct t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30 ccuucucca ggaccaauat t                                            21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
acccugcugu cccagaacct t                                           21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
ggucuauuuc ccaguucgat t                                           21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
cccuggugga cauggugaat t                                           21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34 acaucuccu caucuacact t                                            21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 35
gcaaggauga cuaugugaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ccuucgcuga cuacaaccut t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
cuggcagauc agggccagat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
gacggagacc ucacccugut t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cgggcaagga ugacuaugut t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 40
cuuuugagac ccugcuguat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gagcuggaag gaggagguat t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
acccugcugu cccagaacat t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
ugcuguccca gaaccaggat t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
agccuuuuga gacccugcat t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 45
ccuuuugaga cccugcugat t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
ugaagccuuu ugagacccut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
acugaagccu uuugagacct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
aggaugacua ugugaaggct t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
ggaugacuau gugaaggcat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 50
gaugacuaug ugaaggcact t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cucccucauc uacaccaact t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
gaagccuuuu gagacccugt t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ucucccucau cuacaccaat t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ccucaucuac accaacuaut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 55
cccucaucua caccaacuat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
caacugaagc cuuugagatt                                                21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
aacugaagcc uuugagactt                                                21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
cugaagccuu uugagacccu t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
ucccucaucu acaccaacut t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 60
gcucccucau cuacaccaat t                                            21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
gaagccuuuu gagacccuat t                                            21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
acugaagccu uuugagacat t                                            21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
cucccucauc uacaccaaat t                                            21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
ccucaucuac accaacuaat t                                            21

<210> SEQ ID NO 65
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
accaauaaaa uuucuaagat t                                                   21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
ugccucccug guucugggac a                                                   21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
gacagcaggg ucucaaaagg c                                                   21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
cucccugguu cugggacagc a                                                   21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
ccucccuggu ucugggacag c                                                   21

<210> SEQ ID NO 70
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
gcagggucuc aaaaggcuuc a                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
ugggacagca gggucucaaa a                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
ggacagcagg gucucaaaag g                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ucugggacag cagggucuca a                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
accaccuccu ccuuccagct c                                              21

<210> SEQ ID NO 75
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
caccaccucc uccuuccagc t                                               21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
cuuccagcuc uggcccugat c                                               21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
cugggacagc aggucucaa a                                                21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
uccuuccagc ucuggcccug a                                               21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ccaccuccuc cuuccagcuc t                                               21

<210> SEQ ID NO 80
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
uucugggaca gcaggucuc a                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
caccuccucc uuccagcuct g                                             21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cccugguucu gggacagcag g                                             21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
uugccucccu gguucuggga c                                             21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
cuugccuccc ugguucuggg a                                             21

<210> SEQ ID NO 85
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
gggacagcag ggucucaaaa g                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
guucugggac agcaggguct c                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
uccagcucug gcccugauct g                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
agcagggucu caaaaggcut c                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89 cagcagqguc ucaaaaggct t                                              21
```

```
<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
acagcagggu cucaaaaggc t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
ugcagggucu caaaaggcgt c                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
aaauagacca cgguguaggg c                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
ggagaucugg ucucccacaa t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
ggcaaacucu gccucccgct c                                              21
```

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
uauugguccu ggagaaagga a                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
gguucuggga cagcaggguc t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ucgaacuggg aaauagacca c                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
uucaccaugu ccaccagggc t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
guguagauga gggagaugua t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
uucacauagu cauccuugcc c                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
agguuguagu cagcgaagga g                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
ucuggcccug aucugccagc a                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
acagggugag gucuccgucc t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
acauagucau ccuugcccgc c    21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
uacagcaggg ucucaaaagg c    21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
uaccuccucc uuccagcuct g    21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
uguucuggga cagcaggguc t    21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
uccugguucu gggacagcag g    21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
ugcagggucu caaaaggcut c                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
ucagcagggu cucaaaaggc t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
agggucucaa aaggcuucag t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ggucucaaaa ggcuucagut g                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
gccuucacau agucauccut g                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 114
ugccuucaca uagucaucct t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gugccuucac auagucaucc t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
guugguguag augagggaga t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cagggucuca aaaggcuuca g                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
uugguguaga ugagggagat g                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 119
auaguuggug uagaugaggg a                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
uaguuggugu agaugaggga g                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
ucucaaaagg cuucaguugc c                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gucucaaaag gcuucaguug c                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
gggucucaaa aggcuucagt t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 124
aguuggugua gaugagggag a                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
uugguguaga ugagggagct g                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
uagggucuca aaaggcuuca g                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
ugucucaaaa ggcuucagut g                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
uuugguguag augagggaga t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 129
uuaguuggug uagaugaggg a                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
ucuuagaaau uuuauugguc c                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 131
gaagccuuuu gagacccuan n                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 132
gaagccuuuu gagacccuau u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 133
gaagccuuuu gagacccuau u                                              21

<210> SEQ ID NO 134
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 134
gaagccuuuu gagacccuau u                                             21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 135
gaagccuuuu gagacccuau u                                             21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 136
gaagccuuuu gagacccuau u                                             21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 137
gaagccuuuu gagacccuau u                                             21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide
```

```
<400> SEQUENCE: 138
gaagccuuuu gagacccuau u                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 139
gaagccuuuu gagacccuau u                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 140
gaagccuuuu gagacccuau u                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 141
gaagccuuuu gagacccuau u                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
gaagccuuuu gagacccuat t                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (20)..(21)
<223> OTHER INFORMATION: 2'-OMe-nucleotide

<400> SEQUENCE: 143
gaagccuuuu gagacccuau u                                              21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 144
gaagccuuuu gagacccuau u                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 145
gaagccuuuu gagacccuau u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 146
gaagccuuuu gagacccuau u                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 147
```
gaagccuuuu gagacccuau u                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-deoxy-2'-fluoro-nucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 148
gaagccuuuu gagacccuau u                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 149
gaagccuuuu gagacccuau u                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 150
gaagccuuuu gagacccuau u                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 151
gaagccuuuu gagacccuau u                                         21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 152
gaagccuuuu gagacccuau u                                         21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 153
gaagccuuuu gagacccuau u                                         21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base -continued

```
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 154
gaagccuuuu gagacccuau u                                              21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 155
gaagccuuuu gagacccuau u                                              21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 156
gaagccuuuu gagacccuau u                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
       Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 157
uagggucuca aaaggcuucn n                                              21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 158
uagggucuca aaaggcuucu u                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 159
uagggucuca aaaggcuucu u                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
```

```
<221> NAME/KEY: modified_base
<222> LOCATION: (20)..(21)
<223> OTHER INFORMATION: 2'-OMe-nucleotide

<400> SEQUENCE: 160
uagggucuca aaaggcuucu u                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 161
uagggucuca aaaggcuucu u                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 162
uagggucuca aaaggcuucu u                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
```

```
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 163
uagggucuca aaaggcuucu u                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 164
uagggucuca aaaggcuucu u                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 165
uagggucuca aaaggcuucu u                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
```

<223> OTHER INFORMATION: 2'-OMe-nucleotide

<400> SEQUENCE: 166
uagggucuca aaaggcuucu u                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 167
uagggucuca aaaggcuucu u                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 168
uagggucuca aaaggcuucu u                                              21

<210> SEQ ID NO 169
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 169
uagggucuca aaaggcuucu u                                              21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 170
uagggucuca aaaggcuucu u                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 171
uagggucuca aaaggcuucu u                                              21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Phosphorothioate linkage
<220> FEATURE:
<221> NAME/KEY: modified_base
<222> LOCATION: (20)..(21)
<223> OTHER INFORMATION: 2'-OMe-nucleotide

<400> SEQUENCE: 172
```
uagggucuca aaaggcuucu u                                                 21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 173
uagggucuca aaaggcuucu u                                                 21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
<222> LOCATION: (11)..(12)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 174
uagggucuca aaaggcuucu u                                                 21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 175
uagggucuca aaaggcuucu u                                               21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 176
uagggucuca aaaggcuucu u                                               21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 177
uagggucuca aaaggcuucu u                                               21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)

```
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 178
uagggucuca aaaggcuucu u                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 179
uagggucuca aaaggcuucu u                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
```

```
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 180
uagggucuca aaaggcuucu u                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 181
uagggucuca aaaggcuucu u                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
```

```
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 182
uagggucuca aaaggcuucu u                                         21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 183
ccuuuugaga cccugcugun n                                         21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 184
ccucaucuac accaacuauu u                                         21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 185
```
ccucaucuac accaacuauu u                                                21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 186
ccucaucuac accaacuauu u                                                21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 187
ccucaucuac accaacuauu u                                                21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 188
ccucaucuac accaacuauu u                                                21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 189
ccucaucuac accaacuauu u                                                21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: 2'-OMe-nucleotide

<400> SEQUENCE: 190
ccucaucuac accaacuauu u                                              21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 191
ccucaucuac accaacuauu u                                              21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 192
ccucaucuac accaacuauu u                                              21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 193
ccucaucuac accaacuauu u                                              21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
```

```
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 194
ccucaucuac accaacuauu u                                        21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 195
acagcagggu cucaaaaggn n                                        21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 196
auaguuggug uagaugaggu u                                        21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide
```

```
<400> SEQUENCE: 197
auaguuggug uagaugaggu u                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 198
auaguuggug uagaugaggu u                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 199
auaguuggug uagaugaggu u                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 200
auaguuggug uagaugaggu u                                              21
```

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 201
auaguuggug uagaugaggu u                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 202
auaguuggug uagaugaggu u                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 203
auaguuggug uagaugaggu u                                              21

<210> SEQ ID NO 204
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 204
auaguuggug uagaugaggu u                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 205
auaguuggug uagaugaggu u                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 206
auaguuggug uagaugaggu u                                         21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 207
gaugacuaug ugaaggcacn n                                         21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 208
ggaugacuau gugaaggcau u                                         21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 209
ggaugacuau gugaaggcau u                                         21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 210
ggaugacuau gugaaggcau u                                         21
```

-continued

```
<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 211
ggaugacuau gugaaggcau u                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 212
ggaugacuau gugaaggcau u                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 213
ggaugacuau gugaaggcau u                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 214
ggaugacuau gugaaggcau u                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide
```

```
<400> SEQUENCE: 215
ggaugacuau gugaaggcau u                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 216
ggaugacuau gugaaggcau u                                              21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 217
ggaugacuau gugaaggcau u                                              21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 218
ggaugacuau gugaaggcau u                                              21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
           oligonucleotide
<220> FEATURE:
<221> NAME/KEY: modified_base
<222> LOCATION: (11)..(11)
<223> OTHER INFORMATION: 2'-deoxy-2'-fluoro-nucleotide
<220> FEATURE:
<221> NAME/KEY: modified_base
<222> LOCATION: (13)..(13)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 219
ggaugacuau gugaaggcau u                                      21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 220
ggaugacuau gugaaggcau u                                      21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 221
ggaugacuau gugaaggcau u                                      21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 222
gugccuucac auagucaucn n                                      21
```

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 223
ugccuucaca uagucauccu u                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 224
ugccuucaca uagucauccu u                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 225
ugccuucaca uagucauccu u                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 226
ugccuucaca uagucauccu u                                            21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 227
ugccuucaca uagucauccu u                                            21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 228
ugccuucaca uagucauccu u                                            21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
```

```
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 229
ugccuucaca uagucauccu u                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 230
ugccuucaca uagucauccu u                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 231
ugccuucaca uagucauccu u                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide
```

<400> SEQUENCE: 232
ugccuucaca uagucauccu u                                               21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 233
ugccuucaca uagucauccu u                                               21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 234
ugccuucaca uagucauccu u                                               21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:

```
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 235
ugccuucaca uagucauccu u                                            21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 236
ugccuucaca uagucauccu u                                            21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 237
gaagccuuuu gagacccugn n                                            21

<210> SEQ ID NO 238
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 238
gaagccuuuu gagacccugu u                                                21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 239
gaagccuuuu gagacccugu u                                                21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 240
gaagccuuuu gagacccugu u                                                21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 241
gaagccuuuu gagacccugu u                                                21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 242
gaagccuuuu gagacccugu u                                                21
```

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 243
gaagccuuuu gagacccugu u                                              21

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 244
gaagccuuuu gagacccugu u                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 245
gaagccuuuu gagacccugu u                                              21

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 246
gaagccuuuu gagacccugu u                                              21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: 2'-OMe-nucleotide

<400> SEQUENCE: 247
gaagccuuuu gagacccugu u                                      21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 248
gaagccuuuu gagacccugu u                                      21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 249
cagggucuca aaaggcuucn n                                      21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 250
cagggucuca aaaggcuucu u                                      21

```
<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 251
cagggucuca aaaggcuucu u                                            21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 252
cagggucuca aaaggcuucu u                                            21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
```

<223> OTHER INFORMATION: 2'-OMe-nucleotide

<400> SEQUENCE: 253
cagggucuca aaaggcuucu u                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 254
cagggucuca aaaggcuucu u                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 255
cagggucuca aaaggcuucu u                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 256
cagggucuca aaaggcuucu u                                            21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
cagggucuca aaaggcuucu u                                            21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 258
cagggucuca aaaggcuucu u                                            21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 259
cagggucuca aaaggcuucu u                                            21

<210> SEQ ID NO 260
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 260
cagggucuca aaaggcuucu u                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 261
ccucaucuac accaacuaun n                                              21

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 262
ccucaucuac accaacuauu u                                              21

<210> SEQ ID NO 263
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 263
ccucaucuac accaacuauu u                                                  21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 264
ccucaucuac accaacuauu u                                                  21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 265
ccucaucuac accaacuauu u                                                  21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 266
ccucaucuac accaacuauu u                                                  21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 267
ccucaucuac accaacuauu u                                                  21
```

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 268
ccucaucuac accaacuauu u                                        21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 269
ccucaucuac accaacuauu u                                        21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 270
ccucaucuac accaacuauu u                                        21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 271
ccucaucuac accaacuauu u                                        21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)

```
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 272
ccucaucuac accaacuauu u                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 273
auaguuggug uagaugaggn n                                              21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 274
auaguuggug uagaugaggu u                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
```

```
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 275
auaguuggug uagaugaggu u                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 276
auaguuggug uagaugaggu u                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 277
auaguuggug uagaugaggu u                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
```

```
<220> FEATURE:
<221> NAME/KEY: modified_base
<222> LOCATION: (20)..(21)
<223> OTHER INFORMATION: 2'-OMe-nucleotide

<400> SEQUENCE: 278
auaguuggug uagaugaggu u                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 279
auaguuggug uagaugaggu u                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 280
auaguuggug uagaugaggu u                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 281
```
auaguuggug uagaugaggu u         21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 282
auaguuggug uagaugaggu u         21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic
      oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 283
auaguuggug uagaugaggu u         21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:

```
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 284
auaguuggug uagaugaggu u                                              21

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 285
cuuagugacu uuacuuguau u                                              21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 286
cagaccagca ugacagauuu u                                              21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 287
ugaucuucuc caagaggaau u                                              21

<210> SEQ ID NO 288
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide
```

-continued

<400> SEQUENCE: 288
guucauugca cuugauuau u                                              21

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 289
cauugcacuu ugauuagcau u                                             21

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 290
agcgauggaa cuucgacuuu u                                             21

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 291
gcgauggaac uucgacuuuu u                                             21

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 292
gggaagggac acacaagaau u                                             21

<210> SEQ ID NO 293
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 293
ucuaccucag gcagcucaau u                                              21

<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 294
ggugcucaau aaaugauucu u                                              21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 295
caucaucaaa aacuuuggau u                                              21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 296
aaggagucag acauuuuaau u                                              21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 297
gugcugggca uuuuuauuuu u                                              21
```

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 298
gccggcuuca ugccagcuau u                                              21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 299
gggcaucauc aaaaacuuuu u                                              21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 300
gaagggcacc cuaguucuau u                                              21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 301
caguucauug cacuuugauu u                                              21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: 2'-methoxy-nucleotide

<400> SEQUENCE: 302
acaaggaguc agacauuuuu u                 21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 303
uggaggcacu gaagugcuuu u                 21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 304
gcagggacca cacccuguau u                 21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 305
cuguacuguu cugugucuuu u                 21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 306
uuaaacaccu ccucauguau u                 21

<210> SEQ ID NO 307
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 307
agacucucag ggucgaaaau u                                              21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 308
caugacagau uucuaccacu u                                              21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 309
agauuucuac cacuccaaau u                                              21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 310
ccaagaggaa gcccuaaucu u                                              21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 311
gacagcagag gaagaccauu u                                              21
```

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 312
cucccacaau gcugaauauu u                                              21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 313
uacaaguaaa gucacuaagu u                                              21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 314
aaucugucau gcuggucugu u                                              21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 315
uuccucuugg agaagaucau u                                              21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base

```
<222> LOCATION: (20)..(21)
<223> OTHER INFORMATION: 2'-methoxy-nucleotide

<400> SEQUENCE: 316
uaaucaaagu gcaaugaacu u                                          21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 317
ugcuaaucaa agugcaaugu u                                          21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 318
aagucgaagu uccaucgcuu u                                          21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 319
aaagucgaag uuccaucgcu u                                          21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 320
uucuugugug ucccuucccu u                                          21

<210> SEQ ID NO 321
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 321
uugagcugcc ugagguagau u                                               21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 322
gaaucauuua uugagcaccu u                                               21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 323
uccaaaguuu uugaugaugu u                                               21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 324
uuaaaauguc ugacuccuuu u                                               21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 325
```
aauauaaaau gcccagcacu u                                           21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 326
uagcuggcau gaagccggcu u                                           21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 327
aaaguuuuug augaugcccu u                                           21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 328
uagaacuagg gugcccuucu u                                           21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 329
aucaaagugc aaugaacugu u                                           21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (20)..(21)
<223> OTHER INFORMATION: 2'-methoxy-nucleotide

<400> SEQUENCE: 330
aaaaugucug acuccuuguu u                                              21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 331
aagcacuuca gugccuccau u                                              21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 332
uacagggugu ggucccugcu u                                              21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 333
aagacacaga acaguacagu u                                              21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 334
uacaugagga gguguuuaau u                                              21

<210> SEQ ID NO 335
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 335
uuuucgaccc ugagagucuu u                                              21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 336
gugguagaaa ucugucaugu u                                              21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 337
uuuggagugg uagaaaucuu u                                              21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 338
gauuagggcu uccucuuggu u                                              21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 339
```
auggucuucc ucugcugucu u                                              21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 340
auauucagca uugugggagu u                                              21

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 341
aaggagucag acauuuuaan n                                              21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 342
aaggagucag acauuuuaau u                                              21

<210> SEQ ID NO 343
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (14)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 343
aaggagucag acauuuuaau u                                              21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (14)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 344
aaggagucag acauuuuaau u                                              21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
```

```
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 345
aaggagucag acauuuuaau u                                       21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 346
aaggagucag acauuuuaau u                                       21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 347
aaggagucag acauuuuaau u                                       21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 348
aaggagucag acauuuuaau u                                       21

<210> SEQ ID NO 349
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 349
aaggagucag acauuuuaau u                                              21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 350
aaggagucag acauuuuaau u                                              21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 351
aaggagucag acauuuuaau u                                              21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 352
aaggagucag acauuuuaau u                                              21

<210> SEQ ID NO 353
<211> LENGTH: 21
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 353
aaggagucag acauuuuaau u                                              21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 354
aaggagucag acauuuuaau u                                              21

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 355
uuaaaauguc ugacuccuun n                                              21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
        Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 356
uuaaaauguc ugacuccuuu u                                            21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 357
uuaaaauguc ugacuccuuu u                                            21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 358
uuaaaauguc ugacuccuuu u                                            21
```

```
<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 359
uuaaaauguc ugacuccuuu u                                             21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 360
uuaaaauguc ugacuccuuu u                                             21

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 361
uuaaaauguc ugacuccuuu u                                             21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 362
uuaaaauguc ugacuccuuu u                                            21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 363
uuaaaauguc ugacuccuuu u                                            21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 364
uuaaaauguc ugacuccuuu u                                            21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
```

```
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 365
uuaaaauguc ugacuccuuu u                                        21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 366
uuaaaauguc ugacuccuuu u                                        21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 367
uuaaaauguc ugacuccuuu u                                        21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 368
uuaaaauguc ugacuccuuu u                                        21
```